US011369955B2

(12) United States Patent
Archibald et al.

(10) Patent No.: US 11,369,955 B2
(45) Date of Patent: Jun. 28, 2022

(54) METHOD AND APPARATUS FOR THE ANALYSIS OF COMPOUNDS

(71) Applicant: The University of Hull, Hull Humberside (GB)

(72) Inventors: Stephen James Archibald, Hull Humberside (GB); Ping He, Hull Humberside (GB); Stephen John Haswell, Hull Humberside (GB); Nicole Pamme, Hull Humberside (GB); Nathan Joel Brown, Hull Humberside (GB); Mark Duncan Tarn, Hull Humberside (GB); Richard Alexander, Hull Humberside (GB); Mohammad Mehdi Nasr Esfahani, Hull Humberside (GB)

(73) Assignee: The University of Hull, Hull (GB)

( * ) Notice: Subject to any disclaimer, the term of this patent is extended or adjusted under 35 U.S.C. 154(b) by 149 days.

(21) Appl. No.: 15/521,204

(22) PCT Filed: Oct. 22, 2015

(86) PCT No.: PCT/GB2015/053167
§ 371 (c)(1),
(2) Date: Apr. 21, 2017

(87) PCT Pub. No.: WO2016/063068
PCT Pub. Date: Apr. 28, 2016

(65) Prior Publication Data
US 2018/0169654 A1 Jun. 21, 2018

(30) Foreign Application Priority Data
Oct. 23, 2014 (GB) ...................... 1418897

(51) Int. Cl.
*G01N 33/15* (2006.01)
*B01L 3/00* (2006.01)
(Continued)

(52) U.S. Cl.
CPC .... *B01L 3/502715* (2013.01); *A61K 51/0491* (2013.01); *B01L 3/502738* (2013.01);
(Continued)

(58) Field of Classification Search
None
See application file for complete search history.

(56) References Cited

U.S. PATENT DOCUMENTS 5,757,482 A 5/1998 Fuchs et al.
5,770,030 A 6/1998 Hamacher et al.
(Continued)

FOREIGN PATENT DOCUMENTS

CN 101035602 A 9/2007
CN 101146609 B 3/2008
(Continued)

OTHER PUBLICATIONS

Carrara et al. Multiplexing pH and Temperature in a Molecular Biosensor; Conference Paper, 2010, 4 pages.
(Continued)

*Primary Examiner* — Paul S Hyun
(74) *Attorney, Agent, or Firm* — Sheridan Ross P.C.

(57) ABSTRACT

Embodiments of the present invention relate to microfluidic devices and systems comprising such devices for use in the determination of sample characteristics. Certain embodiments relate to methods for determining one or more characteristics of a sample comprising a compound for in vivo use. Aptly, certain embodiments of the present invention
(Continued)

relate to devices and methods for assessing radiopharmaceuticals and their suitability for administration to a patient in need thereof.

22 Claims, 34 Drawing Sheets

(51) Int. Cl.
*A61K 51/04* (2006.01)
*G01N 31/22* (2006.01)
*G01N 33/94* (2006.01)
*G01N 21/65* (2006.01)
*G01N 33/00* (2006.01)

(52) U.S. Cl.
CPC .......... *G01N 31/221* (2013.01); *G01N 33/15* (2013.01); *G01N 33/94* (2013.01); *B01L 3/502753* (2013.01); *B01L 2200/027* (2013.01); *B01L 2200/04* (2013.01); *B01L 2200/10* (2013.01); *B01L 2200/143* (2013.01); *B01L 2300/0809* (2013.01); *B01L 2300/0816* (2013.01); *B01L 2300/0864* (2013.01); *B01L 2300/0877* (2013.01); *B01L 2300/0883* (2013.01); *B01L 2300/0887* (2013.01); *B01L 2300/12* (2013.01); *B01L 2300/18* (2013.01); *B01L 2400/0622* (2013.01); *G01N 21/65* (2013.01); *G01N 2033/0093* (2013.01)

(56) References Cited

U.S. PATENT DOCUMENTS

| | | | |
|---|---|---|---|
| 6,030,552 A | 2/2000 | Ambras et al. | |
| 6,207,098 B1 | 3/2001 | Nakanishi et al. | |
| 6,827,095 B2 | 12/2004 | O'Connor et al. | |
| 7,670,559 B2 | 3/2010 | Chien et al. | |
| 8,077,311 B1 * | 12/2011 | Byrne | G01N 21/05 356/319 |
| 2004/0174657 A1 | 9/2004 | Andelman et al. | |
| 2005/0079409 A1 | 4/2005 | Andelman et al. | |
| 2005/0226776 A1 | 10/2005 | Brady et al. | |
| 2005/0232387 A1 | 10/2005 | Padgett et al. | |
| 2005/0232861 A1 | 10/2005 | Buchanan et al. | |
| 2006/0160209 A1 * | 7/2006 | Larson | B01L 3/502715 435/287.2 |
| 2006/0228812 A1 | 10/2006 | Higashino et al. | |
| 2007/0138076 A1 | 6/2007 | Daridon et al. | |
| 2007/0166199 A1 | 7/2007 | Zhou et al. | |
| 2008/0064110 A1 | 3/2008 | Elizarov et al. | |
| 2008/0093300 A1 | 4/2008 | Clarke et al. | |
| 2008/0153155 A1 * | 6/2008 | Kato | B01L 3/502707 435/303.1 |
| 2008/0224072 A1 | 9/2008 | Sonnenhol et al. | |
| 2009/0036668 A1 | 2/2009 | Elizarov et al. | |
| 2009/0079409 A1 | 3/2009 | Chang | |
| 2009/0095635 A1 | 4/2009 | Elizarov et al. | |
| 2010/0069600 A1 | 3/2010 | Morelle et al. | |
| 2010/0101943 A1 | 4/2010 | Iwata et al. | |
| 2010/0210458 A1 | 8/2010 | Katsuhara et al. | |
| 2011/0070160 A1 | 3/2011 | Nutt et al. | |
| 2011/0100840 A1 | 5/2011 | Nakanishi et al. | |
| 2011/0150714 A1 | 6/2011 | Elizarov et al. | |
| 2012/0142118 A1 | 6/2012 | Brenna et al. | |
| 2012/0301372 A1 | 11/2012 | Watanabe et al. | |
| 2013/0248366 A1 | 9/2013 | Haswell et al. | |
| 2013/0337493 A1 | 12/2013 | Hansteen et al. | |
| 2014/0030800 A1 * | 1/2014 | Moses | G01N 21/64 435/288.7 |
| 2014/0316130 A1 | 10/2014 | Brady et al. | |
| 2015/0152206 A1 | 6/2015 | Keng et al. | |
| 2017/0368534 A1 | 12/2017 | Archibald et al. | |
| 2018/0025801 A1 | 1/2018 | Archibald et al. | |
| 2018/0033510 A1 | 2/2018 | Archibald et al. | |

FOREIGN PATENT DOCUMENTS

| | | |
|---|---|---|
| CN | 102245305 B | 11/2011 |
| CN | 104039166 A | 9/2014 |
| EP | 1933330 A1 | 6/2008 |
| EP | 2650681 | 10/2013 |
| JP | 2005-257543 | 9/2005 |
| JP | 2010-190602 | 9/2010 |
| WO | 2003078358 A2 | 9/2003 |
| WO | 2004093652 A2 | 11/2004 |
| WO | 2006071470 A2 | 7/2006 |
| WO | WO 2007/122819 | 11/2007 |
| WO | 2008001098 A1 | 1/2008 |
| WO | 2008091694 A9 | 11/2008 |
| WO | 2008157801 A2 | 12/2008 |
| WO | 2009015048 A2 | 1/2009 |
| WO | 2011006166 A1 | 1/2011 |
| WO | 2012009666 A2 | 1/2012 |
| WO | 2013012798 A1 | 1/2013 |
| WO | 2013049577 A1 | 4/2013 |
| WO | 2013054129 A1 | 4/2013 |
| WO | 2013188446 A1 | 12/2013 |
| WO | 2014009379 A1 | 1/2014 |
| WO | 2015039170 A1 | 3/2015 |
| WO | 2016063068 A2 | 4/2016 |
| WO | 2016063069 A1 | 4/2016 |
| WO | 2016063070 A1 | 4/2016 |
| WO | 2016063072 A1 | 4/2016 |

OTHER PUBLICATIONS

Hamacher et al. Efficient Stereospecific Synthesis of No-Carrier-Added 2-[18F] Fluoro-2Deoxy-D-Glucose Using Aminopolyether Supported Nucleophilic Substitution; J-Nuclear Medicine and Biology vol. 27, 1986, pp. 235-238.
Kugler et al. Optimizing the Transfer of[18F]Fluoride From Aqueous to Organic Solvents by Electrodeposition Using Carbon Electrodes Applied Radiation and Isotopes vol. 91, 2014, pp. 1-7.
Pascal et al. Dose-On-Demand of Diverse [18F] Fluorocholine Derivatives Through a Two-Step Microfluidic Approach; Nuclear Medicine and Biology vol. 38, 2011, pp. 637-644.
International Search Report adn Written Opinion issued in PCT/GB2015/053167, dated May 23, 2016, 26 pages.
Alexoff et al. Recovery of [18F] Flouride From [18O] Water in an Electrochemical Cell Appl. Radiat. Isot. vol. 40 No. 1, pp. 1-6, 1989; Int. J. Radiat. Appl. Instrum Part 4.
Bruchet et al. Centrifugal Microfluidic Platform for Radiochemistry: Potentialities for the Chemical Analysis of Nuclear Spent Fuels; Talanta 116 (2013) pp. 488-494.
Elizarov et al. Design and Optimization of Coin-Shaped Microreactor Chips for Pet Radiopharmaceutical Synthesis; Journal of Nuclear Medicine (2010) pp. 282-287.
Hamacher et al. Electrochemical Cell for Separation of [18F] Flouride From Irradiated 18O-Water and Subsequent No Carrier Added Nucleophilic Fluorinaton; Applied Radiation and Isotopes 56 (2002) pp. 519-523.
Hamacher et al. No-Carrier-Added Nucleophilic 18F-Labelling in an Electrochemical Cell Exemplified By the Routine Prodcution of [18F] Altanserin; Applied Radiation and Isotopes 64 (2006) pp. 989-994.
International Preliminary Report on Paentability issued in PCT/GB2015/053171, dated Apr. 25, 2017, 6 pages.
International Preliminary Report on Patentability issued for PCT/GB2015/053170, dated Apr. 25, 2017, 6 pages.
International Preliminary Report on Patentability issued for PCT/GB2015/053173, dated Apr. 25, 2017, 5 pages.
International Preliminary Report on Patentability issued in PCT/GB2015/053167, dated Apr. 25, 2017, 17 pages.
International Search Report and Written Opinion issued in PCT/GB2015/053170, dated Feb. 4, 2016. 11 pages.
International Search Report and Written Opinion issued in PCT/GB2015/053171, dated Feb. 9, 2016, 11 pages.
International Search Report and Written Opinion issued in PCT/GB2015/053173, dated Feb. 2, 2016, 10 pages.

(56) References Cited

OTHER PUBLICATIONS

Ismail et al. Cationic Imidazolium Polymer Monoliths for Efficient Solvent Exchange, Activation and Fluorinaton on a Continuous Flow System; RSC Adv. (2014), 4, 25348-25356.
Saiki, H. et al. Electrochemical Concentration of No-Carrier-Added [18F] Flouride From [18O] Water in a Disposable Microfluidic Cell for Radiosynthesis of 18F-Labeled Radiopharmaceuticals; Applied Radiation and Isotopes 68 (2010) pp. 1703-1708.
UK Search Report Issued in Application No. GB1418893.2, dated Nov. 3, 2015, 5 pages.
UK Search Report Issued in Application No. GB1418895.7, dated Apr. 24, 2015, 5 pages.
UK Search Report Issued in Application No. GB1418897.3, dated Jul. 10, 2015, 6 pages.
UK Search Report issued in Application No. GB1418899.9, dated Apr. 24, 2015, 4 pages.
Fletcher, Paul D. I., et al. Permeability of silica monoliths containing micro- and nano-pores. J Porous Mater, 18:501-508, 2011.
Li, Z. and Conti, P.S. Radiopharmaceutical chemistry for positron emission tomography. Advanced Drug Delivery Reviews, 62:1031-1051, 2010.
Mewis, R.E. and Archibald, S.J. (2010). Biomedical applications of macrocyclic ligand complexes. Coordination Chemistry Reviews, Review, 254:1686-1712.
Phelps, M.E. (2000). Positron emission tomography provides molecular imaging of biological processes. PNAS, 97 (16):9226-9233.
Silversides, J. D., Smith, R., Archibald, S. J. Challenges in chelating positron emitting copper isotopes: Tailored synthesis of unsymmetric chelators to form ultra stable complexes. Dalton Transactions, "Radiopharmaceuticals for Imaging and Therapy," 40:6289-6297, 2011.
Wood, Laura D., et al. The Genomic Landscapes of Human Breast and Colorectal Cancers. Sciencexpress, Research Article, Oct. 11, 2007, pp. 1-8 paginated and accompanying images.
Haroun, S.; et al. (2013). Continuous-flow synthesis of [11C]raclopride, a positron emission tomography radiotracer, on a microfluidic chip. Can. J. Chem. 91:326-332.
Nakao, R. et al. "Improved radiometabolite analysis procedure for positron emission tomography (PET) radioligands using a monolithic column coupled with direct injection micellar/high submicellar liquid chromatography," Talanta 113 (2013) 130-134; available online Mar. 15, 2013. (Year: 2013).
Phenomenex. "Onyx—Monolithic Silica HPLC Columns" brochure, 6 pages, 2013; downloaded from <https://phenomenex.blob.core.windows.net/documents/2791ff52-0585-4146-9c00-fbb700e390f0.pdf>on Oct. 24, 2019 (Year: 2013).
Rensch, C.; et al. (2013). Microfluidics: A groundbreaking technology for PET tracer production? Molecules, 18:7930-7956.
Tarn, M.D. et al. "Purification of 2-[18F]fluoro-2-deoxy-d-glucose by on-chip solid-phase extraction," Journal of Chromatography A, 1280 (2013) 117-121; available online Jan. 15, 2013. (Year: 2013).
Grinias et al., "Advances in and prospects of microchip liquid chromatography," Trends in Analytical Chemistry, vol. 81, 2016, pp. 110-117.
He et al., "Monolith-based 68Ga processing: A new strategy for purification to facilitate direct radiolabelling methods," Reaction Chemistry and Engineering, vol. 1, 2016, pp. 361-365.
Meyer et al., "The stability of 2-[18F]fluoro-deoxy-D-glucose towards epimerisation under alkaline conditions," Applied Radiation and Isotopes, vol. 51, 1999, pp. 37-41.
Silversides et al., "Challenges in chelating positron emitting copper isotopes: Tailored synthesis of unsymmetric chelators to form ultra stable complexes," Dalton Transactions, vol. 40, 2011, pp. 6289-6297.
Tarn et al., "Positron detection in silica monoliths for miniaturised quality control of PET radiotracers," Chemical Communications, vol. 52, 2016, pp. 7221-7224.

Official Action for U.S. Appl. No. 15/521,198, dated May 15, 2019, 7 pages. Restriction Requirement.
Official Action for U.S. Appl. No. 15/521,198, dated Nov. 4, 2019, 21 pages.
Official Action for U.S. Appl. No. 15/521,198, dated May 29, 2020, 20 pages.
Official Action for U.S. Appl. No. 15/521,207, dated Oct. 11, 2019, 10 pages. Restriction Requirement.
Official Action for U.S. Appl. No. 15/521,207, dated Feb. 6, 2019, 9 pages.
Official Action for U.S. Appl. No. 15/521,207, dated Jun. 20, 2019, 10 pages.
Official Action for U.S. Appl. No. 15/521,207, dated Oct. 10. 2019, 9 pages.
Official Action for U.S. Appl. No. 15/521,207, dated Mar. 18, 2020, 8 pages.
Official Action for U.S. Appl. No. 15/521,207, dated Sep. 11, 2020, 9 pages.
Official Action for U.S. Appl. No. 15/521,205, dated Jul. 31, 2018, 28 pages.
Official Action for U.S. Appl. No. 15/521,205, dated Aug. 22, 2019, 36 pages.
Official Action for U.S. Appl. No. 15/521,205, dated Feb. 28, 2020, 32 pages.
Unger et al., "Chapter 3: Column Technology in Liquid Chromatography," in "Liquid Chromatography: Fundamentals And Instrumentation," (ed. Fanali et al.), Elsevier, Waltham, MA, 2013, 48 pages.
Official Action for U.S. Appl. No. 15/521,205, dated Nov. 20, 2020, 36 pages.
Arima et al., "Radiochemistry on chip: towards dose-on-demand synthesis of PET radiopharmaceuticals," Lab on a Chip, vol. 13, Mar. 25, 2013, pp. 2328-2336.
Kutter, "Liquid phase chromatography on microchips," Journal of Chromatography A., vol. 1221, Oct. 21, 2011, pp. 72-82.
Official Action for U.S. Appl. No. 15/521,198, dated Mar. 16, 2021, 20 pages.
Official Action for U.S. Appl. No. 15/521,207, dated Apr. 5, 2021, 10 pages.
Notice of Allowance for U.S. Appl. No. 15/521,205, dated Mar. 15, 2021, 6 pages.
Chiu et al. "Small but Perfectly Formed? Successes, Challenges, and Opportunities for Microfluidics in the Chemical and Biological Sciences," Chem, Feb. 2017, vol. 2, pp. 201-223.
Pereiro et al. "Nip the bubble in the bud: a guide to avoid gas nucleation in microfludics," Lab Chip, 2019, vol. 19, pp. 2296-2314.
Stone et al. "Engineering Flows in Small Devices," Annual Review of Fluid Mechanics, 2004, vol. 36, pp. 381-411.
Whitesides "The origins and the future of microfluidics," Nature, Jul. 2006, vol. 442, pp. 368-373.
Official Action with English Translation for Japan Patent Application No. 2017-541173, dated Jun. 14, 2021, 9 pages.
Sadeghi et al. "Reusable electrochemical cell for rapid separation of [18F]fluoride from [18O]water for flow-through synthesis of 18F-labeled tracers," Applied Radiation and Isotopes, 2013, vol. 75, pp. 85-94.
Wong et al. "Reactivity of electrochemically concentrated anhydrous [18F]fluoride for microfluidic radiosynthesis of 18F-labeled compounds," Applied Radiation and Isotopes, 2012, vol. 70, pp. 193-199.
Official Action for U.S. Appl. No. 15/521,198, dated Jan. 24, 2022 15 pages.
Official Action for U.S. Appl. No. 15/521,207, dated Feb. 3, 2022 11 pages.

* cited by examiner

| Characteristic/analyte | Threshold (European Pharmacopoeia) | Method of Detection |
|---|---|---|
| Appearance / clarity | Clear, colourless or slightly yellow | Absorption spectroscopy and Raman spectroscopy |
| pH | 4.5 - 8.5 | Colourimetric assay with universal pH indicator; absorption spectroscopy |
| Kryptofix 2.2.2 | 2.2 mg/V (or 50 ppm in USP) | Colourimetric assay with iodoplatinate; absorption spectroscopy |
| Residual solvents | Ethanol = 5000 ppm<br>Acetonitrile = 410 ppm | Raman spectroscopy |
| Bacterial endotoxins | 175 IU/V | Colourimetric endpoint LAL assay (three reagents added sequentially: (i) LAL reagent, (ii) chromogenic substrate, (iii) dilute acetic acid); absorption spectroscopy |
| FDG | 0.5 mg/V | Anion exchange liquid chromatography on a strong anion exchange (SAX) monolithic column; sodium hydroxide mobile phase; positron detection and pulsed amperometric detection (PAD) |
| ClDG | 0.5 mg/V | Anion exchange liquid chromatography on a strong anion exchange (SAX) monolithic column; sodium hydroxide mobile phase; positron detection and pulsed amperometric detection (PAD) |
| [$^{18}$F]FDM | Max. 10% of total activity | Anion exchange liquid chromatography on a strong anion exchange (SAX) monolithic column; sodium hydroxide mobile phase; positron detection and pulsed amperometric detection (PAD) |
| [$^{18}$F]fluoride+<br>[$^{18}$F]ACY-FDG+<br>[$^{18}$F]ACY-FDM | Max. 5% of total activity | Liquid chromatography on a silica or C18 monolithic column; mobile phase of acetonitrile/water mixture; positron detection |
| [$^{18}$F]FDG+<br>[$^{18}$F]FDM | Min. 95% of total activity | Liquid chromatography on a silica or C18 monolithic column; mobile phase of acetonitrile/water mixture; positron detection |

V = maximum recommended dose in millilitres

FIG. 1

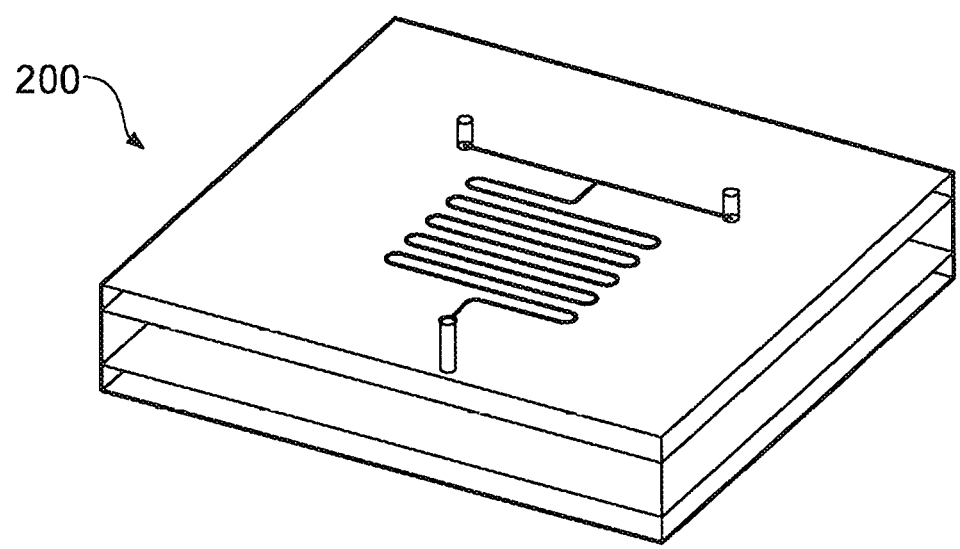
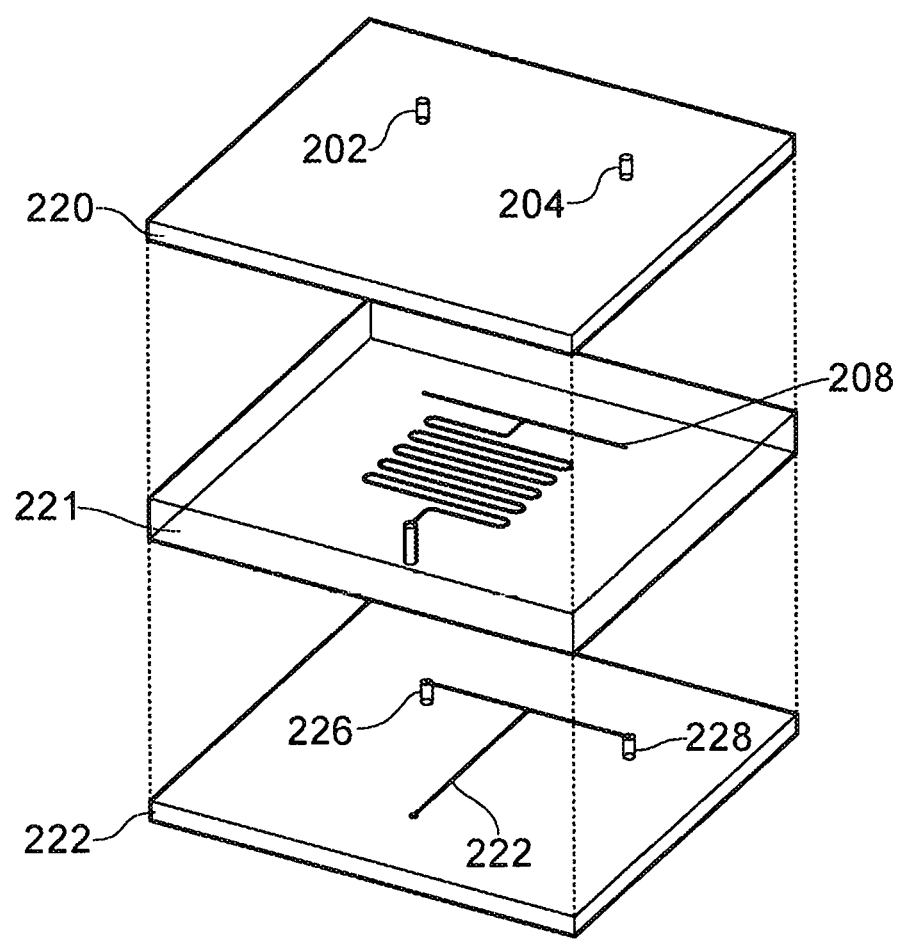
FIG. 6B

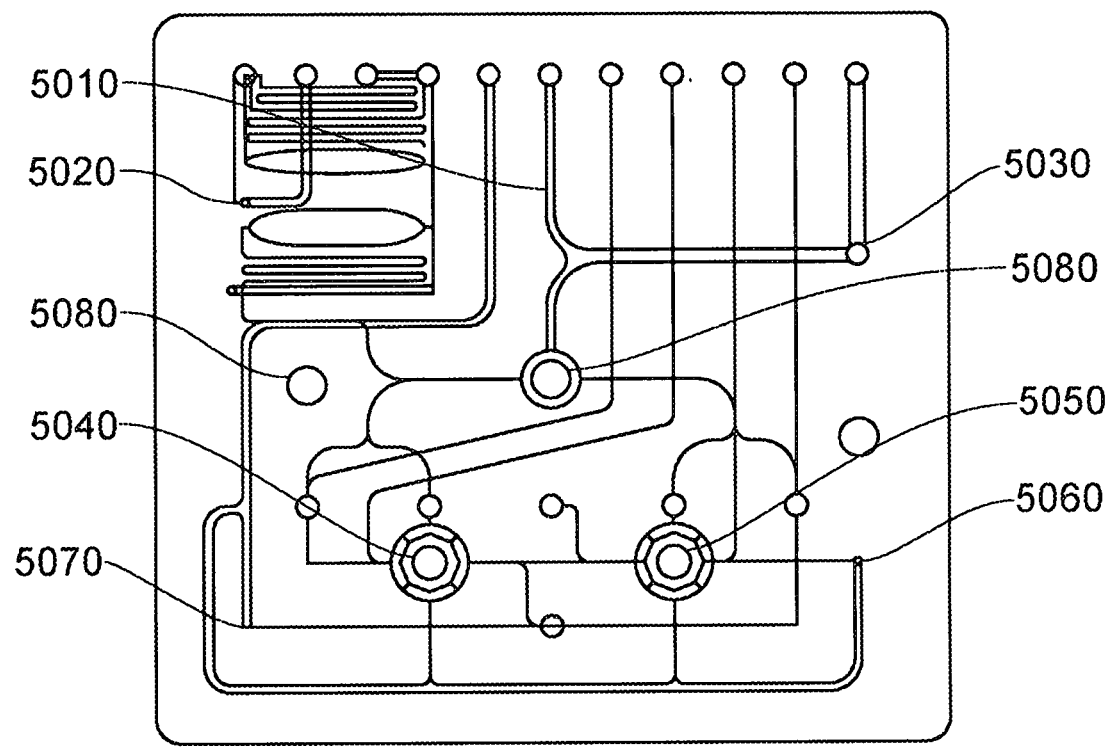
(a)
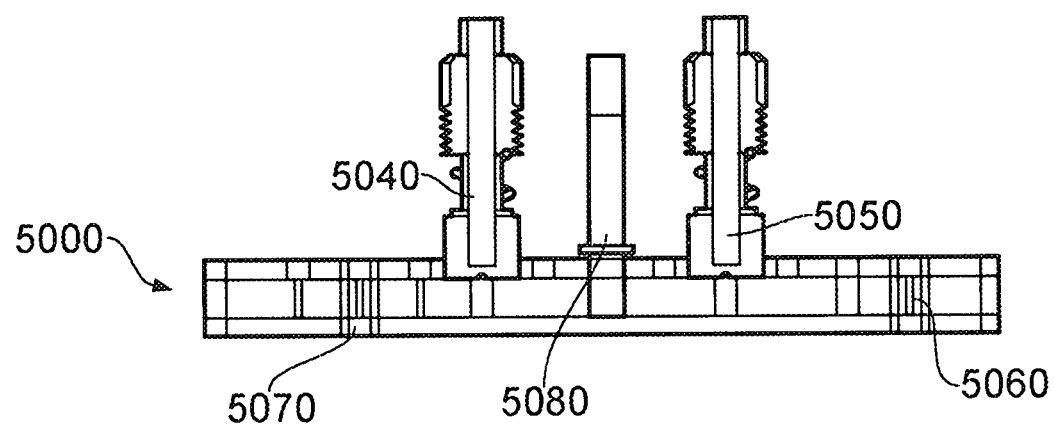
(b)
FIG. 34

METHOD AND APPARATUS FOR THE ANALYSIS OF COMPOUNDS

Cross-Reference to Related Applications

This application is a national stage application under 35 U.S.C. 371 of PCT Application No. PCT/GB2015/053167 having an international filing date of Oct. 22, 2015, which designated the United States, which PCT application claimed the benefit of Great Britain Patent Application No. 1418897.3 filed Oct. 23, 2014, all of which are incorporated herein by reference in their entirety.

FIELD OF THE INVENTION

Embodiments of the present invention relate to microfluidic devices and systems comprising such devices for use in the determination of sample characteristics. Certain embodiments relate to methods for determining one or more characteristics of a sample comprising a compound for in vivo use. Aptly, certain embodiments of the present invention relate to devices and methods for assessing radiopharmaceuticals and their suitability for administration to a patient in need thereof.

BACKGROUND TO THE INVENTION

Positron emission tomography (PET) has become a very powerful and widely used medical imaging modality for the diagnosis and monitoring of a variety of diseases and conditions. The technique relies on the (typically) intravenous injection of a radiotracer—a targeting molecule labelled with a short-lived radioisotope—into a patient, and the subsequent scanning of the patient in a PET scanner to image the biodistribution of the tracer. Clearly, the injection of a solution containing the radiotracer into a human patient necessitates that the injectable dose be sterile, at a physiological pH, be free of particulate matter, and not contain any potentially harmful starting materials or by-products that may be present as a result of the synthesis procedure. With this in mind, stringent quality control (QC) tests must be performed on injectable doses in order to ensure their suitability for human injection. The tests required for a specific radiotracer are listed in various pharmacopoeia monographs, which detail the techniques/instrumentation to be used and the limits allowed for the different molecules present in the dose.

The most commonly used PET radiotracer is a glucose derivative labelled with the $[^{18}F]$fluoride radioisotope: 2-$[^{18}F]$fluoro-2-deoxy-D-glucose (alternatively known as fludeoxyglucose, F-FDG, or $[^{18}F]$FDG. $[^{18}F]$FDG was first developed for PET in the mid-1970s by the group of Wolf et al., who prepared the tracer via electrophilic substitution. Nowadays, production typically takes place using the nucleophilic substitution method developed by Hamacher et al, Jour. Nucl. Med, 1986, 27, 235-238. Since its initial development, $[^{18}F]$FDG has become an important imaging tracer in oncology, neurology, and cardiology, being used to monitor glucose metabolism. Other PET radiotracers include for example $^{18}F$-FLT ($[^{18}F]$fluoro thymidine), $^{18}F$-FDDNP (2-(I-{6-[(2-$[^{18}F]$fluoroethyl)(methyl)amino]2-naphthyl}ethylidene)malononitrile), $^{18}F$-FHBG (9-[4-$[^{18}F]$fluoro-3-(hydroxymethyl)butyl]guanine or $[^{18}F]$-penciclovir), $^{18}F$-FESP ($[^{18}F]$-fluoroethylspiperone), $^{18}F$-p-MPPF (4-(2-methoxyphenyl)-I-[2-(N-2-pyridinyl)-p-$[^{18}F]$fluorobenzamido]ethylpiperazine), $^{18}F$-FDG ($[^{18}F]$-2-deoxy-2-fluoro-D-glucose), $^{18}F$-FMISO ($^{18}F$-fluoromisonidazole) and $^{18}F$-sodium fluoride.

Other radiotracers include e.g. $^{68}Ga$-NOTA-bis (phosphonate), $^{68}Ga$-DOTATOC and $^{68}Ga$-DOTATATE.

Due to its importance and widespread use, the QC requirements for $[^{18}F]$FDG as well as other radiotracer are well-documented in the various pharmacopoeia guidelines.

In recent years, paradigm shifts in the production of radiopharmaceuticals have started to come to the fore, in particular with regards to the concepts of "dose-on-demand" (DOD) and "decentralised production". Currently, PET Centres having a cyclotron will synthesise batches of $[^{18}F]$FDG and transport single or multi-doses to hospitals for PET imaging. However, this does not enable targeting of specific patients with specific conditions, but is more economical since it is easier to produce large volumes of $[^{18}F]$FDG rather than multiple smaller doses of other radiotracers. Dose-on-demand and decentralised production are intended to reverse this scenario by producing a radiotracer of choice as and when needed for a specific patient. There are two main methods by which these scenarios are being addressed.

Firstly, a recent technological advance of the "mini" PET cyclotron can be installed within a hospital to allow on-site generation of $[^{18}F]$fluoride. Mini-cyclotrons are designed to be smaller and far less costly than traditional PET cyclotrons, in addition to being self-shielded, which enables their simple installation within a facility without the need for bespoke infrastructure. This type of cyclotron allows only small volumes of $[^{18}F]$fluoride to be produced for the on-demand synthesis of a single dose of radiotracer. Currently, the BG-75 Biomarker Generator mini-cyclotron is available from Advanced Biomarker Technologies (ABT).

While the use of mini-cyclotron represents one type of radiotracer decentralised production, by locating the entire production process within a hospital site, another scenario is that $[^{18}F]$fluoride would actually continue to be generated by a traditional cyclotron at a PET Centre. However, rather than synthesising a batch of radiotracer at the PET Centre itself, the $[^{18}F]$fluoride would instead be transported directly to the imaging site where the radiotracer production would take place. This would allow more flexibility in terms of the type of radiotracer being produced, even if the imaging site did not have direct access to a cyclotron.

With changes in radiosynthesis technologies comes the need for quality control systems to monitor the radiotracers being produced. While the pharmacopoeia tests set the current standards, they require the use of a variety of different techniques and instrumentation, including thin-layer chromatography (TLC), high performance liquid chromatography (HPLC), and gas chromatography (GC), among others. Nonetheless, there are continuing efforts to lower the limits of detection, shorten the testing times, and reduce the sample volumes required. Recently, efforts have also been made to integrate multiple QC tests into a single technique in order to streamline the QC process, thus reducing the instrumentation required and the radiation exposure experienced by technicians.

More generally, streamlining of quality control processes of other compounds which are for in vivo use, e.g. pharmaceuticals, is also desired.

It is an aim of aspects of the present invention to at least partially mitigate the problems associated with the prior art.

It is an aim of certain embodiments of the present invention to provide a quality control system to test microfluidic quantities of a compound which is for in vivo use.

It is an aim of certain embodiments of the present invention to provide a microfluidic device on which one or more quality control tests may be carried out.

SUMMARY OF CERTAIN EMBODIMENTS OF THE INVENTION

In a broadest aspect, the present invention provides a method and apparatus for the quality control (QC) analysis of microfluidic quantities of a sample of a compound.

Aptly, the compound is for in vivo use. Aptly, certain embodiments of the present invention provide an integrated apparatus which is capable of performing a plurality of analytical techniques to assist in determining whether the compound is suitable for administration to a patient. Certain embodiments of the present invention provide the advantage that the majority of the sample supplied to the apparatus is then supplied to a patient in need thereof. Thus, certain embodiments reduce the requirement to make additional samples of the compound simply to use in quality control analysis.

In an aspect of the present invention, there is provided a method of determining at least one characteristic of a sample comprising a compound which is for in vivo use, the method comprising:

supplying the sample to a supply component of a microfluidic chip; wherein the sample supplied to the supply component has a volume of 1 ml or less;

directing the sample or a portion thereof from the supply component, via a fluid flow path which is in fluid communication with the supply component, to a detection zone provided by the microfluidic chip; and performing at least one analytical technique on the sample or the portion thereof when provided at the detection zone.

Aptly, the microfluidic chip comprises a plurality of detection zones, and wherein the method comprises performing an analytical technique at each detection zone. In certain embodiments, at least one analytical technique comprises absorption spectroscopy.

In one embodiment, the method comprises supplying the sample to the microfluidic chip in a volume of 500 µl or less, e.g. 200 µl or less e.g. 100 µl or less, e.g. 90 µl, 80 µl, 70 µl, 50 µl, 40 µl, 30 µl, 20 µl, 10 µl, 5 µl, 2 µl or less.

Aptly, the fluid flow path comprises a microchannel. Aptly, the fluid flow path comprises at least one further microchannel.

Aptly, the supply component comprises an inlet port. In one embodiment, the method comprises the step of obtaining a measurement value from the analytical technique and determining the at least one characteristic. In one embodiment, the method further comprises comparing the measurement value to a predetermined corresponding criterion value.

Aptly, the method is a method of quality control testing the sample. Aptly, the compound is a radiopharmaceutical. Aptly, the compound is a radiopharmaceutical comprising a radioisotope selected from $^{89}Zr$, $^{64}Cu$, $^{18}F$, $^{99m}Tc$, $^{11}C$, and $^{68}Ga$. Aptly, the radiopharmaceutical is selected from $^{18}F$-FLT ($[^{18}F]$fluoro thymidine), $^{18}F$-FDDNP (2-(I-{6-[(2-[$^{18}F$]fluoroethyl)(methyl)amino]2-naphthyl}ethylidene)malonitrile), $^{18}F$-FHBG (9-[4-[$^{18}F$]fluoro-3-(hydroxymethyl)butyl]guanine or [$^{18}F$]-penciclovir), $^{18}F$-FESP ([$^{18}F$]-fluoroethylspiperone), $^{18}F$-p-MPPF (4-(2-methoxyphenyl)-I-[2-(N-2-pyridinyl)-p-[$^{18}F$]fluorobenzamido]

ethylpiperazine), $^{18}F$-FDG ([$^{18}F$]-2-deoxy-2-fluoro-D-glucose), $^{18}F$-FMISO ($^{18}F$-fluoromisonidazole) and $^{18}F$-sodium fluoride.

In one embodiment, the radiopharmaceutical is selected from $^{68}Ga$-NOTA-bis (phosphonate), $^{68}Ga$-DOTATOC and $^{68}Ga$-DOTATATE.

In one embodiment, the method further comprises directing a portion of the sample from the inlet port to an outlet port for collection via the microchannel or a further microchannel. In one embodiment, the method comprises directing at least 70% e.g. 80%, 85%, 90%, 95% or more of the sample to the outlet port for collection, wherein optionally the sample directed to the outlet port for collection is a single unit dose of the compound.

Aptly, the portion of the sample directed to the outlet port is the same portion as that directed to the detection zone. In one embodiment, the portion of the sample directed to the outlet port is a different portion to the portion of the sample directed to the detection zone.

In one embodiment, the method further comprises, dependent on the determination of the at least one characteristic, supplying the compound for in vivo use.

Aptly, the at least one analytical technique comprises a spectroscopic technique. In one embodiment, the spectroscopic technique is UV-visible spectroscopy. In one embodiment, the spectroscopic technique is visible-near infrared spectroscopy.

In one embodiment, the method comprises determining pH of the sample. In one embodiment, the method comprises supplying a universal pH indicator solution to a further inlet port of the microfluidic chip and mixing the universal pH indicator solution with the sample or a portion thereof.

Aptly, the method comprises mixing the universal pH indicator solution with the sample or portion thereof in a serpentine channel provided in the fluid flow path.

Aptly, the method comprises directing a flow of a mixture of the universal pH indicator solution and the sample or portion to the detection zone and performing a spectroscopic technique e.g. UV-visible spectroscopy or visible-near infrared spectroscopy, on the mixture of the pH indicator solution and the sample or portion thereof. In one embodiment, the method further comprises plotting a radar plot and/or a V-shaped plot to determine the pH of the sample.

In an embodiment, the step of determining pH of the sample comprises performing an electrochemical detection technique. Aptly, the technique may be based on methods disclosed in Carrara et al, 2010 Biomedical Circuits and Systems Conference (BioCAS).

Aptly, the method further comprises determining presence and/or a concentration of an impurity in the sample. Aptly, the method comprises determining the presence and/or concentration of Kryptofix 2.2.2 in the sample. In one embodiment, the method comprises supplying an iodoplatinate reagent to a further supply component of the microfluidic chip and mixing the iodoplatinate reagent with the sample or a portion thereof. Aptly, the method comprises comparing a measurement value obtained with a predetermined corresponding criterion value.

Aptly, the method comprises mixing the iodoplatinate solution with the sample in a serpentine channel provided in the fluid flow path. Aptly, the serpentine channel is a further serpentine channel. In one embodiment, the method comprises mixing the iodoplatinate solution with the sample in a chamber provided in the fluid flow path.

In one embodiment, the method further comprises performing a spectroscopic technique on the mixture of the iodoplatinate reagent and the sample or portion thereof and obtaining a measurement value. Aptly, the measurement value represents the concentration of Kryptofix 2.2.2 in the sample. In one embodiment, the method comprises comparing the measurement values to a predetermined corresponding criterion value to determine whether the sample is suitable for in vivo use.

Aptly, the spectroscopic technique is UV-visible spectroscopy. In one embodiment, the spectroscopic technique is visible-near infrared spectroscopy.

In one embodiment, the method comprises determining the concentration of bacterial endotoxin in the sample. In one embodiment, the method comprises supplying a limulus amebocyte lystate (LAL) reagent solution to an inlet port of the microfluidic chip and mixing the LAL reagent with the sample or portion thereof. In one embodiment, the method comprises supplying a colourimetric reagent to an inlet port of the microfluidic chip and mixing the colourimetric reagent with the mixture of LAL reagent and sample or portion thereof. Aptly, the method further comprises supplying a stop reagent e.g. 25% acetic acid to the mixture of LAL reagent, colourimetric reagent and sample or portion thereof. Aptly, the method comprises performing a spectroscopic technique on the mixture and obtaining a measurement value. In one embodiment, the method comprises heating the mixture of LAL reagent and sample or portion thereof prior to performing the spectroscopic technique.

Aptly, the spectroscopic technique is UV-visible spectroscopy or visible-near infrared spectroscopy.

In one embodiment, the method comprises determining the clarity and/or appearance of the sample or a portion thereof. In one embodiment, the method comprises performing UV-visible spectroscopy and/or visible-near infrared spectroscopy and/or Raman spectroscopy on the sample or a portion thereof.

Aptly, the detection zone comprises a detection channel extending at least partially through a thickness of the microfluidic chip, wherein the detection zone provides a path length for light from the light source to be transmitted to the detector.

In one embodiment, the method comprises positioning a light source and a detector at opposing surfaces of the microfluidic chip such that the detection channel is provided between the light source and the detector and provides a pathlength for light emitted by the light source to be transmitted to the detector. Aptly, the microchip has a thickness, a width and a length and wherein the thickness is less than the width and less than the length.

In one embodiment, the method is for determining the concentration of one or more solvents in the sample. In an embodiment, the method comprises directing a flow of the sample or a portion thereof to the detection zone and performing a spectroscopic analytical technique thereon to obtain a measurement value. Aptly, the analytical technique is Raman spectroscopy. Aptly, the method comprises obtaining a measurement value from the spectroscopic technique and comparing the value to a predetermined corresponding criterion value to determine the characteristic.

In one embodiment, the method is for determining the concentration of ethanol and/or acetonitrile in the sample.

In one embodiment, the method is for determining a concentration of an impurity in the sample, wherein the method comprises: delivering the sample or a portion thereof to the detection zone, wherein the detection zone comprises a separation element; and directing a flow of the sample or portion thereof through the separation element, thereby separating the sample or portion thereof into one or more molecularly distinct constituents.

Aptly, the separation element is selected from a high performance liquid chromatography component and a chromatographic monolithic body. Aptly the monolithic body is as described herein.

Aptly, the microfluidic chip comprises a further separation element which is in fluid communication with an electrochemical cell and the method comprises delivering the sample or portion thereof to the further separation element and directing a flow of the sample or portion thereof through the separation element, thereby separating the sample or portion thereof into one or more molecularly distinct constituents. The separation element may be a monolithic body e.g. a monolithic module. In certain embodiments, the separation element is a strong anionic exchange (SAX) liquid chromatography column.

Aptly, the method comprises mixing the sample or portion thereof with a mobile phase having a pH of 11 or greater prior to delivering the sample to the detection zone comprising the further separation element. Aptly, the mobile phase comprises sodium hydroxide.

In certain embodiments, the method comprises performing a pulsed electrochemical detection method. Aptly, the pulsed electrochemical detection method is pulsed amperometric detection (PAD).

In one embodiment, the method comprises:
(a) directing a flow of the sample or portion thereof from the separation element to the electrochemical cell;
(b) passing the flow of the sample or portion thereof past a working electrode;
(c) applying at least three pulsed electrical potentials to said working electrode; and
(d) detecting the output from said working electrode during at least part of the time period of applying said second potential.

Aptly, the method comprises applying the at least three pulsed electrical signals with a potentiostat.

Aptly, the at least three pulsed electrical potentials comprises:
(1) a first potential, wherein the first potential is a measurement potential,
(2) a second potential, wherein the second potential is an oxidative cleaning potential; and
(3) a third potential, wherein the third potential is a regenerative potential, and wherein the second potential is higher than the first and third potentials and the first potential is higher than the third potential.

Aptly, the first potential serves to condition or activate the surface of the working electrodes for detection.

Aptly, the method comprises repeating step (c) one or more times.

Aptly, the electrochemical cell comprises a working electrode, a reference electrode and counter electrode.

In such embodiments, the method is for detecting impurities such as for example, [$^{18}$F]FDG, 2-[$^{18}$F]fluoro-2-deoxy-D-mannose ([$^{18}$F]FDM), 2-chloro-2-deoxy-D-glucose (CIDG), D-mannose and/or D-glucose. Aptly, the step of mixing the basic mobile phase with the sample or portion thereof renders one or more sugars in the sample e.g. [$^{18}$F]FDG, [$^{18}$F]FDM, CIDG, D-mannose and/or D-glucose negatively charged, which allows for separation and detection of the sugars.

In certain embodiments, the method comprises detecting the output from said working electrode during at least part of the time period of applying said second potential using a potentiostat.

In one embodiment, the method comprises determining a radiation level of the sample. Aptly, a positron detector is used to determine a radiation level of the sample. In certain embodiments, the method comprises:

directing a flow of the sample or portion thereof through the separation element, thereby separating the sample or portion thereof into one or more molecularly distinct constituents, wherein the separation element comprises a silica monolith e.g. a reverse phase silica monolith e.g. a octadecyltrimethoxysilane-functionalised silica monolith. Aptly, the method comprises mixing the sample or portion thereof with a mobile phase e.g. a mobile phase comprising acetonitrile and water. In certain embodiments, the method further comprises monitoring radiation level using a positron detector.

In one embodiment, the microfluidic chip comprises a plurality of detection zones, wherein one or more characteristics are determined at each detection zone. Aptly, the electrochemical cell is provided at a first detection zone and wherein the detection channel is provided at a second detection zone.

Aptly, the separation elements are provided at a further detection zone. In one embodiment, the microfluidic chip comprises a plurality of detection zones, each of which comprises a detection channel.

In one embodiment, the method comprises controlling the direction and/or timing of the flow of the sample or portion(s) thereof through the microfluidic chip by way of one or more valve elements. Aptly, the step of causing the fluid to enter and flow through the microfluidic channel via the inlet is performed under a hydraulic pressure, negative pressure or by a pump.

Aptly, the method comprises determining at least two characteristics of the sample, for example, at least three characteristics of the sample, e.g. at least four characteristics of the sample.

Aptly, the method is performed on a microfluidic device comprising the microfluidic chip and which comprises one or more further components.

In a further aspect of the present invention, there is provided a microfluidic chip for determining at least one characteristic of a sample comprising a compound which is for in vivo use, the microfluidic chip comprising:
a) a length (L1), a width (W1) and a thickness (T1) wherein T1<W1 (less than) and T1<L1 (less than);
b) a supply component for introducing the sample into the chip;
c) a fluid flow path in fluid communication with the supply component, and
c) a detection channel in the fluid flow path, wherein the detection channel extends at least partially through the thickness (T1) of the microfluidic chip and wherein the detection channel is configured to provide both a fluid flow path and a path length along a long axis thereof.

Thus, the chip comprises a detection channel which extends at least partially through the thickness of the chip. Aptly, in use the detection channel provides an optical path length between a detector and a source, such that absorbance spectrum of a fluid in the detection channel may be determined. In one embodiment, the source is capable of emitting electromagnetic radiation at a wavelength of between about 200 nm to about 2000 nm. Aptly, the source is a light source.

In an embodiment, the chip comprises a plurality of layers e.g. two or three or more.

In one embodiment, the path length and the fluid flow path are provided along the same axis of the detection channel. Aptly, the detection channel is approximately 2 mm to 4 mm in length e.g. between 3 mm to 4 mm in length.

In one embodiment, the detection channel is enclosed within the microfluidic chip. Aptly, the chip further comprises one or more valve elements for directing and/or controlling fluid flow in the fluid flow path. In one embodiment, the detection channel is axially aligned with the light source and the detector in use. In one embodiment, the detector and/or the light source each comprise a connecting element for connecting the chip to the detector and/or source and wherein the detection channel is axially aligned with the connecting element(s) in use.

Aptly, at least a portion of the chip is composed of a material which is capable of optical transmission. Aptly, each portion of the chip which is positioned adjacent to the light source and the detector in use is capable of optical transmission.

Aptly, the fluid flow path comprises a first microchannel. Aptly, the fluid flow path comprises at least one further microchannel. In certain embodiments, the first microchannel and/or the at least one further microchannel are provided in a different plane to the detection channel.

In one embodiment, the detection channel comprises an upper opening and a lower opening, and wherein the detection channel is configured to permit flow of a fluid along a long axis thereof. In one embodiment, a fluid is capable of exiting the detection channel via the lower opening. In one embodiment, the fluid is capable of exiting the detection channel via the upper opening. Aptly, an outlet is provided in fluid communication with the lower opening of the detection channel. Aptly, an outlet is provided in fluid communication with the upper opening of the detection channel.

In one embodiment, the microfluidic chip comprises a plurality of detection channels. In one embodiment, the detection channel is a detection zone. Aptly, the microfluidic chip further comprises one or more further detection zones, wherein the one or more further detection zones may comprise a detection channel and/or an alternative analysis element.

In a further aspect of the present invention, there is provided a microfluidic chip for determining one or more characteristics of a sample comprising a compound for in vivo use, wherein the chip comprises:
(a) a supply component for introducing the sample to the microfluidic chip;
(b) a fluid flow path in fluid communication with the supply component;
(c) at least two detection zones, each detection zone comprising an component for performing an analytical technique;
(d) a plurality of isolation valve elements provided in the fluid flow path to control and/or direct fluid flow in the fluid flow path;
wherein each isolation valve element is movable from an open position to a closed position such that a portion of the sample is isolated for direction to a detection zone of the microfluidic chip.

According to a yet further aspect of the present invention there is provided a microfluidic chip comprising a valve assembly comprising:
a valve member having a valve axis, a first end region and a further end region; and a valve housing engagable with a microfluidic chip to locate the further end region of the valve member in a fluid flow path of the microfluidic chip;

wherein the further end region of the valve member comprises at least one through conduit and the valve member is rotatable about the valve axis with respect to the valve housing to selectively move the at least one through conduit between an open position and a closed position relative to the fluid flow path of the microfluidic chip.

Aptly, the microfluidic chip comprises a plurality of valve assemblies.

Aptly, the microfluidic chip comprises any of the features described above. For example, aptly, the microfluidic chip further comprises:

a) a length (L1), a width (W1) and a thickness (T1) wherein T1<W1 (less than) and T1<L1 (less than); and
b) a detection channel provided in the fluid flow path, wherein the detection channel extends at least partially through the thickness (T1) of the microfluidic chip and wherein the detection channel is configured to provide both a fluid flow path and a path length along a long axis thereof.

Aptly, the detection channel is as described above.

Aptly, the portion of the sample is isolated between pairs of isolation valve elements. Aptly, the isolation valve element comprises a plurality of valve components. Aptly, the isolation valve element is a valve assembly as described herein below.

According to a yet further aspect of the present invention, there is provided a valve assembly for a microfluidic chip, comprising:

a valve member having a valve axis, a first end region and a further end region; and
a valve housing engagable with a microfluidic chip to locate the further end region of the valve member in a fluid flow path of the microfluidic chip;
wherein the further end region of the valve member comprises at least one through conduit and the valve member is rotatable about the valve axis with respect to the valve housing to selectively move the at least one through conduit between an open position and a closed position relative to the fluid flow path of the microfluidic chip.

Aptly, the valve member is translatable in a direction along the valve axis with respect to the valve housing.

In certain embodiments, the valve assembly further comprises a biasing element to bias the further end region of the valve member away from the valve housing in a direction along the valve axis.

Aptly, the valve member is substantially elongate and comprises an annular shoulder portion disposed between the first end region and the further end region for engagement with the biasing element.

Aptly, the valve housing comprises an annular wall portion and an upper portion having a central aperture to receive the valve member and to locate the biasing element between the upper portion and the annular shoulder of the valve member.

In certain embodiments, the annular wall portion comprises a first screw thread for engagement with a further screw thread of the microfluidic chip.

Aptly, the biasing element comprises a compression spring. Aptly, the compression spring has a spring force associated with a predetermined threshold pressure of fluid transportable in the fluid flow path of the microfluidic chip.

Aptly, the valve assembly further comprises an adjuster for adjusting a length of the compression spring.

Aptly, the valve member comprises a valve shaft extending from a valve head portion comprising the at least one through conduit. In certain embodiments, the valve shaft is received in a central bore of the valve head portion. Aptly, the valve shaft and the valve head portion are connected by at least one of an adhesive, a friction fit, and a screw thread.

Aptly, the valve shaft comprises the annular shoulder portion and an upper surface of the valve head portion abuts a lower surface of the annular shoulder portion. In certain embodiments, the valve head portion comprises a substantially resilient material. Aptly, the substantially resilient material comprises a biomedical grade elastomer. In certain embodiments, the biomedical grade elastomer comprises a silicone rubber.

Aptly, the valve shaft and valve housing each comprise a metal or polymer material. In certain embodiments, the at least one through conduit comprises at least one channel disposed in a lower surface of the further end region of the valve member.

Aptly, the channel comprises a width of about 100 μm to about 200 μm e.g. about 150 μm and a depth of for example about 50 μm deep.

Aptly, the first end region of the valve member comprises a spline for engagement with an actuator to drive the valve member relative to the valve axis.

The microfluidic chip of aspects of the present invention may further comprise any one or more of the following features:

In one embodiment, the fluid flow path comprises a first microchannel which comprises a plurality of isolation valve elements e.g. a plurality of valve assemblies.

In one embodiment, the fluid flow path of the microfluidic chip comprises at least one further microchannel, wherein each further microchannel is in fluid communication with a different portion of the first microchannel provided between a pair of isolation valve elements.

Aptly, each of the at least one further microchannel is in fluid communication with a detection zone. Aptly, a plurality of further microchannels is in fluid communication with a single detection zone.

In one embodiment, the at least one further microchannel comprises a valve element to control and/or direct flow of a fluid from the plurality of further microchannels to the detection zone.

Aptly, the detection zone comprises one or more of the analytical components selected from:
a) an electrochemical cell;
b) a radiation detector;
c) a separation element; and
d) a detection channel.

Aptly, the chip comprises a plurality of detection zones, each detection zone comprising at least one analytical component.

Aptly, the analytical component is an electrochemical cell which comprises a working electrode, a counter electrode and a reference electrode.

In one embodiment, the working electrode is a gold electrode. Alternatively, the working electrode is formed from ITO (indium tin oxide) or carbon. Aptly, the counter electrode (also referred to as an "auxiliary electrode") is formed from silver, carbon or platinum. Aptly, the reference electrode is formed from silver.

Aptly, the electrochemical cell is a screen-printed electrode assembly.

In one embodiment, the detection zone further comprises one or more inlets for supplying a reagent or a mobile phase. Aptly, the chip further comprises one or more outlets.

The separation element as described herein may comprise a chromatographic monolithic body, for example a monolithic column. A "monolithic body" or "monolith" is a single solid structure comprising open macropores and mesopores which pores together form an interconnected network of channels. In one embodiment, the monolithic body comprises a silica-based composition, for example silica, for example functionalised silica. Typically the monolithic body of the invention is highly porous. Typically the monolithic body has a high surface area, for example at least 100 $m^2/g$, in particular at least 150 $m^2/g$ used and more particularly 100 to 300, e.g. 100 to 250 $m^2/g$, for example 150 to 200 $m^2/g$.

As described herein, the separation element is comprised in a component which is separable from the chip, for example the component may be a monolithic module.

A "monolithic module" comprises one or more monolithic body/bodies in a hermetically sealed unit comprising at least one inlet and at least one outlet. The monolithic module is adapted for incorporation into a monolithic flow system. The monolithic module may be prepared by an injection moulding process. Aptly the monolithic body is inorganic. In certain embodiments, the separable component comprises a plurality of monolithic bodies, which may be the same or different. Aptly, the separable component comprises two monolithic bodies.

A monolithic body may be prepared using a sol-gel procedure. For example, a silica monolith may be prepared by adding a polymer such as PEO (polyethylene oxide) to an aqueous solution of acid, with cooling and stirring. Silicon alkoxide, (for example TEOS—tetraethyl orthsilicate) is then added with stirring to form a transparent solution. This solution is poured into a mould and heated (40° C., 3 days) to form a wet semi-solid gel monolith. The gel is removed from the mould, washed with water and then added to ammonium hydroxide for further heating (80° C., 24 hours). The monoliths are washed and dried (60° C., 2 days). A monolithic body may have a length of e.g. 10 to 35 mm and a diameter of 4 mm or width of 4 mm and a depth of 1.5 mm. For further details on the preparation of silica monoliths please see P. D. I. Fletcher, S. J. Haswell, P. He, S. M. Kelly, A. Mansfield, J Porous Mater. 2011, 18, 501.

A process for the manufacture of a monolithic body may comprise the steps of:
  i) supplying a mould for injection moulding containing an inorganic monolithic body;
  ii) injecting liquid polymer (for example COC or PMMA) into the mould wherein the liquid polymer flows between a surface of the mould and a surface of the monolithic body and surrounds the monolithic body, except for the area of contact between the mould and monolithic body;
  iii) setting the polymer to form a partial monolithic module;
  iv) inserting the partial monolithic mould into a second mould for injection moulding;
  v) injecting liquid polymer into the mould wherein the liquid polymer flows between a surface of the mould and an exposed surface of the monolithic body to further surround the monolithic body;
  vi) setting the polymer to form the monolithic module.
  vii) optionally, where necessary annealing the monolithic unit;
  viii) optionally where necessary, providing an inlet and/or outlet from the surface of the monolithic body to the outer surface of the monolithic module, for example by machining, for example by drilling.

A monolithic module may comprise a monolithic body, a layer of first polymer and a layer of second polymer. In one embodiment, a monolithic body is substantially surrounded by a layer of first polymer and the layer of first polymer is substantially or partially surrounded by a layer of second polymer. The monolithic body may be described as having a double coating. The monolithic module may be provided with and inlet and/or outlet.

For example the first polymer is an elastomer, e.g. silicone. Aptly, the liquid polymer is a biomedical grade silicone. Aptly, the liquid polymer is MDX4-4210 biomedical grade silicone. MDX4-4210 biomedical grade silicone is a biomedical grade elastomer (as known as SILASTIC® MDX4-4210). Silicone is commercially available, for example SILASTIC® MDX4-4210 is commercially available from Dow Corning.

For example the second polymer is a plastic, for example the second polymer is selected from polycarbonate (PC), polymethylacrylate (PMMA), cyclic olefin copolymer (COC) and polyethylene (PE).

A process for the manufacture of a monolithic body having a double coating may comprise the steps of:
  i) supplying a mould for injection moulding containing an inorganic monolithic body;
  ii) injecting a liquid polymer (e.g. silicone as described herein) into the mould wherein the liquid polymer flows between a surface of the mould and a surface of the monolithic body and surrounds the monolithic body, except for the area of contact between the mould and monolithic body;
  iii) setting the polymer to form a monolithic module;
  iv) optionally, where necessary annealing the monolithic module;

The mould of step i) forms part of the monolithic module. There is thus formed a monolithic body comprising a double coated monolithic body.

In step i) the mould may be in the form of a plastic holder for example prepared by machining e.g. CNC (computer numerical control) machining. Alternatively the mould may be itself prepared by an injection moulding process, for example comprising a polymer selected from polycarbonate (PC), polymethylacrylate (PMMA), cyclic olefin copolymer (COC) and polyethylene (PE). Thus the process may further comprise (prior to step i)) the step of preparing a mould by machining or preparing a mould by injection moulding for example using a polymer selected from polycarbonate (PC), polymethylacrylate (PMMA), cyclic olefin copolymer (COC) and polyethylene (PE).

Another process for the manufacture of a monolithic body having a double coating may comprise the steps of:
  i) supplying a mould for injection moulding containing an inorganic monolithic body;
  ii) injecting a first polymer (e.g. silicone as described herein) into the mould to substantially surround a surface of the monolithic body;
  iii) setting the polymer to form a partial monolithic module;
  iv) inserting the partial monolithic module into a second mould for injection moulding;
  v) injecting a second polymer (e.g. a plastic for example selected from polycarbonate (PC), polymethylacrylate (PMMA), cyclic olefin copolymer (COC) and polyethylene (PE)) into the mould to substantially surround a surface of the first polymer;

vi) setting the second polymer.

There is thus formed a monolithic body comprising a double coated monolithic body.

The process for the manufacture of a monolithic module may further comprise the step of providing the double coated monolithic module with an inlet and outlet. The inlet and outlet extend between the surface of the monolithic body and the outer surface of the monolithic module. The inlet and/or outlet may be provided by machining the monolithic module, for example by drilling or milling. The monolithic module may be machined after setting the polymer(s) and, if present, before or after the annealing step. In one embodiment, the inlet and/or outlet may be provided during the injection step(s) by using a mould adapted to provide an inlet and/or outlet.

A monolithic body may be chemically functionalised by soaking the monolithic body in an appropriate reaction mixture prior to inclusion in a monolithic module or the monolithic body may be functionalised as part of the monolithic module by passing functionalization reagents through the monolithic module. For further details on the functionalization of silica monoliths please see C. S. Gill, B. A. Price, C. W. Jones, J Catal. 2007, 251, 145 or C. R. Silva, C. Airoldi, K. E. Collins, C. H. Collins, LCGL North America 2004, 22, 632.

Aptly, the supply component is an inlet port. In one embodiment, the electrochemical cell, the radiation detector and/or the separation element is comprised in a component which is separable from the chip and which is positioned in use in fluid communication with the fluid flow path. In one embodiment, the fluid flow path comprises at least one passive mixing element in at least a portion thereof.

Aptly, the passive mixing element is selected from a straight ridge, an angled ridge, a chevron canal, a dome, a cone, a pit, a post and a combination thereof. Aptly, the passive mixing element comprises a plurality of ridges in a staggered herringbone pattern.

In one embodiment, the microfluidic chip is formed from a material selected from the group consisting of polydimethyl-siloxane (PDMS), Polyethylene (PE), Polycarbonate (PC), Polystyrene (PS), Polymethyl methacrylate (PMMA), Cyclic Olefin Copolymer (COC), Cyclic olefin polymer (COP), silicon, quartz, glass, thermoplastic materials and combinations thereof.

Aptly, the chip is for determining one or more of the following characteristics:
a) pH of the sample;
b) appearance/clarity of the sample;
c) presence and/or concentration of bacterial endotoxin in the sample;
d) presence and/or concentration of an impurity in the sample;
e) radiation level of the sample; and/or
f) Kryptofix 2.2.2 detection.

Aptly, the compound is a radiopharmaceutical. Details of exemplary radiopharmaceuticals are provided herein. In one embodiment, the compound is a pharmaceutical.

Aptly, the microfluidic chip comprises one or more analysis components. Aptly, the one or more analysis components are provided at a detection zone of the chip. Aptly, the fluid flow path is provided in both a generally horizontal plane and a generally vertical plane.

Aptly, the microfluidic chip is provided as a component of a microfluidic device. Aptly, the supply component is configured to receive the sample from a component of the microfluidic device. In an embodiment, the supply component is in fluid communication with a channel of the device wherein the sample flows from the channel to the inlet port.

In a further aspect of the present invention, there is provided a system for determining at least one characteristic of a sample comprising a compound which is for in vivo use, the system comprising a microfluidic chip as described herein and one or more further components. Aptly, the one or more further component are selected from one or more of the following:
a) a source;
b) a detector; and
c) a computer.

In one embodiment, the source is a light source. Aptly, the detector is a spectrometer, for example a visible-near infrared (vis-NIR) spectrometer, UV-visible (UV-Vis) light spectrometer and/or a Raman spectrometer. Aptly, the system further comprises one or more elements for aligning the detector and/or the source to the microfluidic chip. Aptly, the source and the detector and/or the connecting element(s) are aligned such they are orthogonal to the chip and aligned with a long axis of the detection channel such that the detection channel provides a path length between the source and the detector.

In certain embodiments, the detector and/or the source is a potentiostat.

In certain embodiments, the system comprises a plurality of sources, for example, a potentiostat and one or more light sources.

In an embodiment, the system comprises a plurality of detectors, for example, a visible-near infrared spectrometer, UV-visible light spectrometer, a radiation detector, a Raman spectrometer and/or a potentiostat.

In one embodiment, the system further comprises a first connecting element configured to connect the source to the chip. Aptly, the first connecting element is provided in close proximity to the chip and is a first optical fibre having a first end and a second end. Aptly, the system further comprises a second connecting element which is connected to the detector and is provided adjacent to the chip, wherein the second connecting element is a second optical fibre having a first end and a second end.

In one embodiment, the system further comprises a third connecting element, wherein the third connecting element is configured to connect a potentiostat adjacent to a detection zone of the chip which comprises an electrochemical cell. Aptly, the third connecting element is a wire element.

In certain embodiments, the system further comprises a holder device for holding the chip. The holder device may comprise a holder body having a cavity configured to retain the chip. Aptly, the holder body comprises an upper layer and a lower layer. Aptly, the upper layer comprises an upper surface which comprises one or more through holes configured to accommodate one or more connecting elements. Aptly, at least one of the one or more through holes is configured to accommodate an optical fibre and/or a wire element. Aptly, each through hole is configured to enable the connecting element to connect a detector and/or a source to a detection zone of the chip.

Aptly, the holder device comprises at least one fixed locator and at least one locator moveable against a resilient bias, wherein the locators contact the chip and the at least one biased locator urges the chip against the at least one fixed locator so as to locate the chip in a predetermined position relative to the holder device and wherein when the chip is so held the source and at least one detection zone are mutually positioned for operation of the source on the detection zone.

In one embodiment, the holder body comprises a supporting surface for supporting a base surface of the chip.

Aptly, the chip comprises four side edges arranged in a rectangle and wherein the holder device comprises at least two fixed locators and at least two resiliently biased locators and wherein when the chip is hold in the holder device, the at least two fixed locators contact two adjacent ones of the side edges and the at least two resiliently biased locators contact a different two adjacent ones of the four side edges.

Aptly, the source emits a beam which comprises a width, and wherein the detection channel comprises a width, wherein the width of the beam is greater than the width of the detection channel, such that when the chip is held by the holder body adjacent to the source, the variation in position of the chip relative to the source is sufficiently small in relation to relative widths of the beam and the detection channel so that said position variation does not affect the detection of the sample in the detection channel.

In an alternative embodiment, the width of the beam is smaller than the detection channel width.

In a further aspect of the present invention there is provided a method of determining at least one characteristic of a sample comprising a compound for in vivo use, the method comprising:
a) introducing the sample to a microfluidic chip via a supply component, wherein the microfluidic chip comprises:
  i) a length (L1), a width (W1) and a thickness (T1) wherein T1<W1 and T1<L1;
  ii) a supply component for introducing the sample into the chip;
  iii) a fluid flow path which is in fluid communication with the supply component, and
  iv) a detection channel provided in the fluid flow path, wherein the detection channel extends at least partially through the thickness (T1) of the microfluidic chip and wherein the detection channel is configured to provide both a fluid flow path and a path length along a long axis thereof;
b) arranging a source and a detector such that the detection channel provides a path length therebetween;
c) flowing a fluid comprising the sample or a portion thereof along the detection channel;
d) transmitting electromagnetic radiation from the source along the path length whilst the fluid is provided in the detection channel; and
e) obtaining a measurement value from the detector.

In one embodiment, the method comprises performing a spectroscopic analytical technique to obtain the measurement value. Aptly, the method comprises transmitting light having a wavelength of between about 180 nm to about 2400 nm from the source. Aptly, the wavelength is between 340 to about 1020 nm. Aptly, the wavelength is between about 350 nm to about 500 nm.

In one embodiment, the measurement value is compared to one or more measurements values of a standard to determine the characteristic.

In one embodiment, the method further comprises mixing the sample or a portion thereof with a reagent to form the fluid prior to flowing the fluid into the detection channel. Aptly, the analytical technique is a colourimetric assay. In one embodiment, the method further comprises mixing the sample or a portion thereof with a pH indicator, wherein the method is for the determination of pH of the sample. In one embodiment, the method further comprises plotting a radar plot and/or a V-shaped plot to determine the pH of the sample.

In a further aspect of the present invention, there is provided a method of determining pH of a radiopharmaceutical, comprising:
a) introducing the sample to an inlet of a microfluidic chip, wherein the microfluidic chip comprises:
  i) a length (L1), a width (W1) and a thickness (T1) wherein T1<W1 and T1<L1;
  ii) a supply component for introducing the sample to the chip;
  iii) a fluid flow path which is in fluid communication with the supply component, and
  iv) a detection channel in the fluid flow path, wherein the detection channel extends at least partially through the thickness (T1) of the microfluidic chip and wherein the detection channel is configured to provide both a fluid flow path and a path length along a long axis thereof;
b) arranging a source and a detector such that the detection channel provides a path length therebetween;
c) mixing the sample or a portion thereof with a pH indicator solution to form a fluid;
d) flowing a fluid comprising the sample or a portion thereof along the detection channel;
e) transmitting electromagnetic radiation from the source along the path length whilst the fluid is provided in the detection channel; and
f) obtaining a measurement value from the detector.

Certain embodiments of the present invention utilise a spectroscopic technique for the determination of pH. Certain embodiments of the present invention avoid the disadvantage of electrode fouling, which can occur when electrodes are used to measure pH. In addition, certain embodiments of the present invention avoid the need for complex microfabrication of electrodes. Furthermore, the use of a spectroscopic technique can avoid the subjectivity associated with the use of pH paper. The use of spectroscopic techniques in certain embodiments of the present invention may also require a smaller volume of sample in order to determine pH.

In a further aspect of the present invention, there is provided a method of determining one or more characteristics of a sample comprising compound for in vivo use, the method comprising:
supplying the sample to a microfluidic chip, wherein the microfluidic chip comprises a fluid flow path;
providing a directional force to flow the sample through the fluid flow path;
selectively moving one or more isolation valve elements provided in the fluid flow path from an open position to a closed position to isolate a portion of the sample;
flowing an isolated portion of the sample towards a detection zone; and;
performing an analytical technique on the isolated portion of the sample at the detection zone.

In one embodiment, a portion of the sample is directed towards an outlet and the method comprises collecting the portion for use in vivo. Aptly, the microfluidic chip is as described herein. In one embodiment, the method further comprises one or more steps as described herein.

In one embodiment, the method comprises performing a spectroscopic analytical technique on an isolated portion of the sample. Aptly, the fluid flow path between each pair of valve elements is in fluid communication with an inlet for supplying a driving solution which entrains the isolated portion towards a detection zone. Aptly, the method is for determining at least two characteristics of the sample, e.g. three, four, five, six or more.

According to a yet further aspect of the present invention there is provided a method of isolating at least a portion of a sample comprising a compound for in vivo use for delivery to a detection zone of a microfluidic chip, the method comprising the steps of:

rotating a valve member about a valve axis to selectively move at least one through conduit disposed in an end region of the valve member between an open position and a closed position relative to a fluid flow path of a microfluidic chip.

Aptly, the method further comprises, when in the open position, aligning the at least one through conduit with a first input channel of the at least one fluid flow path to receive the at least a portion of a sample in the at least one through conduit.

Aptly, the method further comprises, when in the open position, aligning the at least one through conduit with a first output channel of the at least one fluid flow path to allow the at least a portion of the sample to flow from the first inlet channel to the first outlet channel.

Aptly, the method further comprises, when in the closed position, closing the first inlet channel with the valve member and aligning the at least one through conduit with a further output channel of the at least one fluid flow path to allow the at least a portion of the sample to flow from the at least one through conduit to the further outlet channel.

Certain embodiments of the present invention provide the advantage of providing a detection channel which can provide both a fluid flow path for an analyte and a path length for transmission e.g. optical transmission. Aptly, the detection channel is provided at least partially through the thickness of the microfluidic chip, thus taking up less space than a detection channel which is provided along the width or length of the chip. The provision of the detection channel of certain embodiments described herein therefore allows the chip to accommodate more than one detection channel and/or other analytical zones on the same microfluidic chip.

Aptly, the microfluidic chip is a microfluidic chip as described herein. Further details of embodiments of the invention are provided below.

DETAILED DESCRIPTION OF EMBODIMENTS OF THE INVENTION

Embodiments of the present invention will now be described hereinafter, by way of example only, with reference to the accompanying drawings in which:

FIG. 1 is a table showing a plurality of characteristics which can be determined using the apparatus and methods of certain embodiments of the present invention;

FIG. 6b is an exploded side view of a microfluidic chip in accordance with certain embodiments of the present invention;

Figure 8:
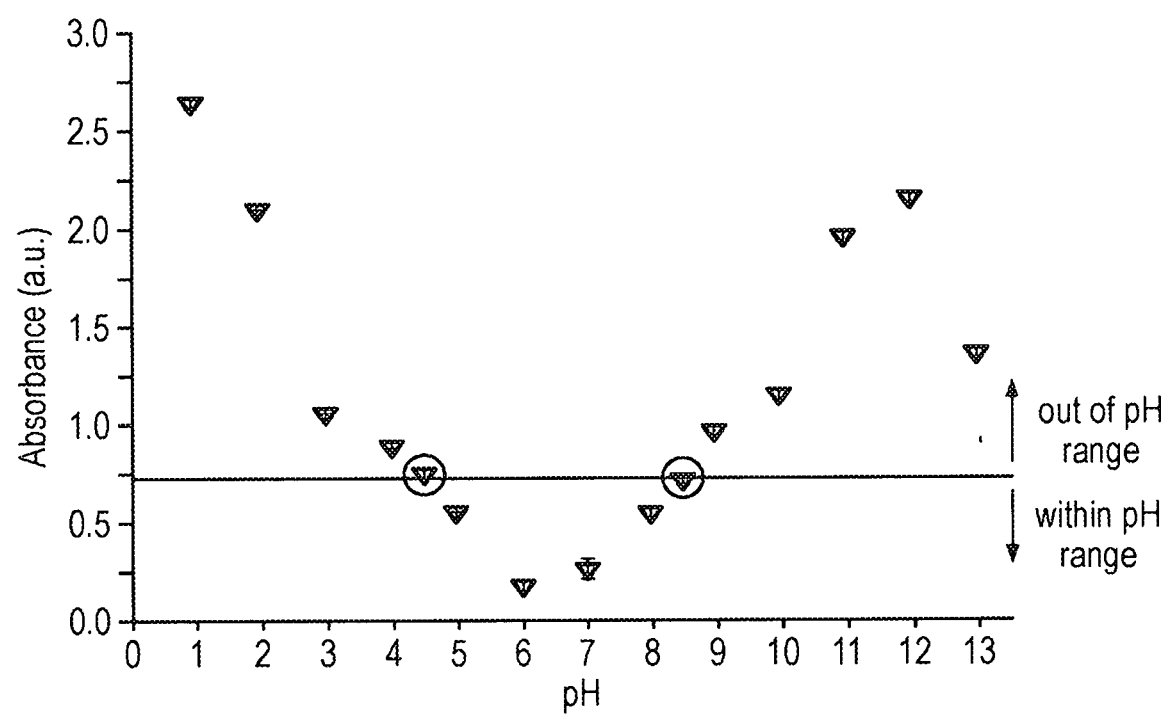
Figures 9, 10:
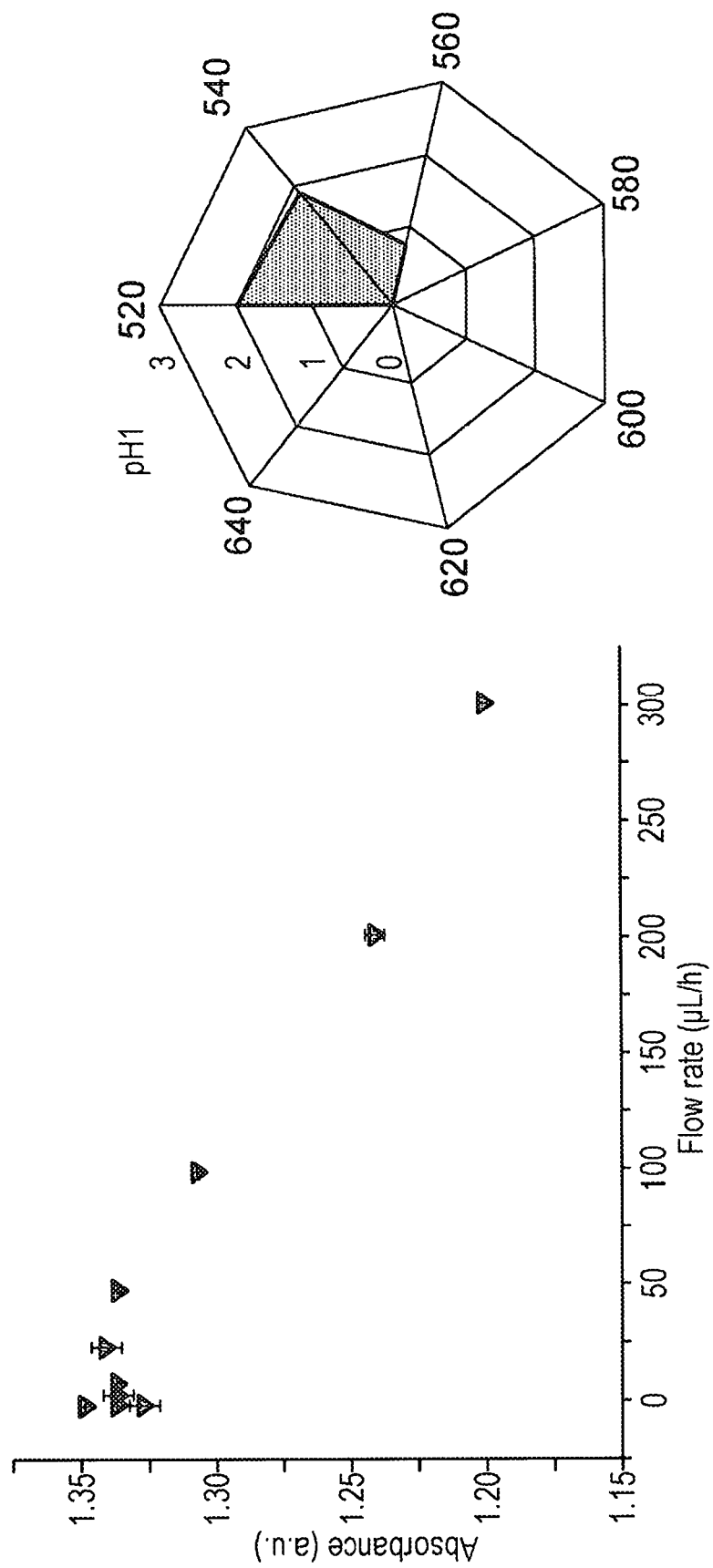

FIG. 8 is a graph indicating the plotting of absorbance values at a wavelength of from about 545 to 600 nm for a range of pH standards (pH 1 to 13) forming a V-shaped plot. A straight line is then drawn across the absorbance values of pH 4.5 and 8.5 (the accepted range for in vivo use). Every absorbance value from a sample that is below this line is then within the acceptable pH 4.5-8.5 range, while absorbance above this line are unacceptable and the sample would be rejected. This method gives a "yes/no" answer as to whether the sample is within the acceptable pH range;

FIG. 9 is a graph illustrating the effect of flow rate on the colourimetric reaction between a pH 10 standard solution and Universal indicator solution being pumped into the chip and mixed (by diffusion only, i.e. without the presence of herringbone structures). At higher flow rates the reagents are less likely to mix properly before passing through the detection channel, hence the reduced signal intensities. At lower flow rates the reagents have sufficient time to mix properly, hence the larger signal intensities.

Figure 11:
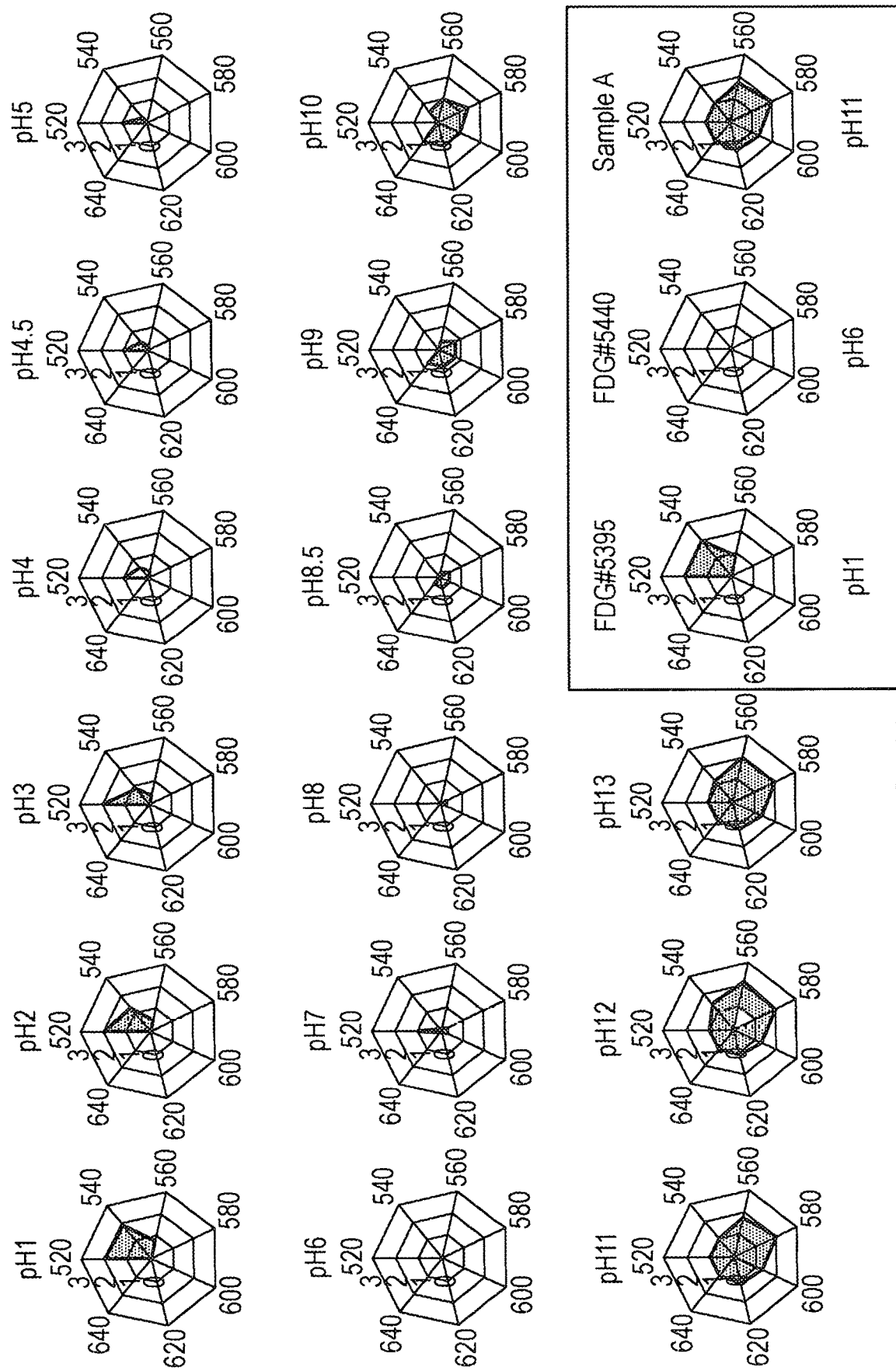
Figure 12:
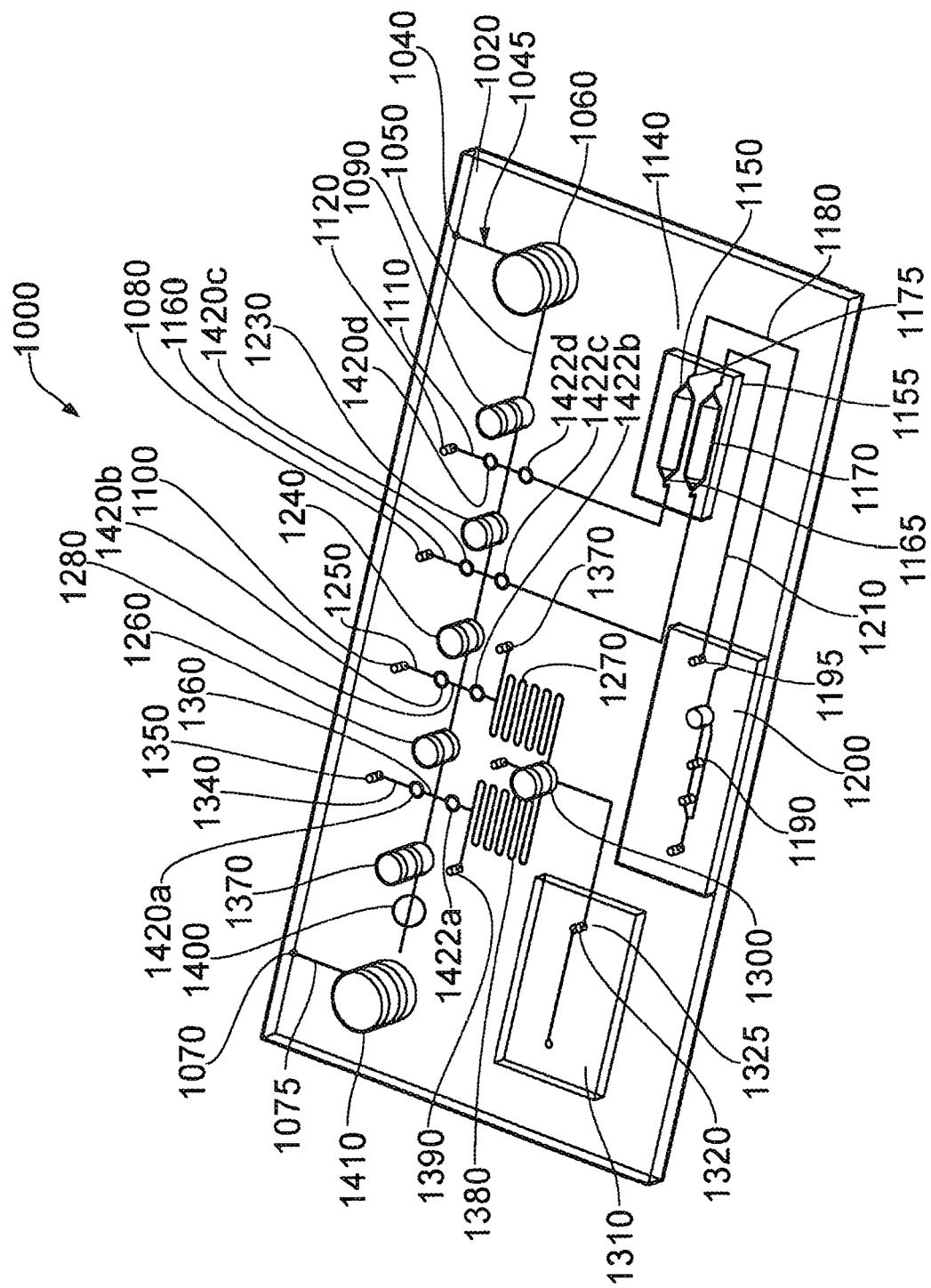
Figure 13:
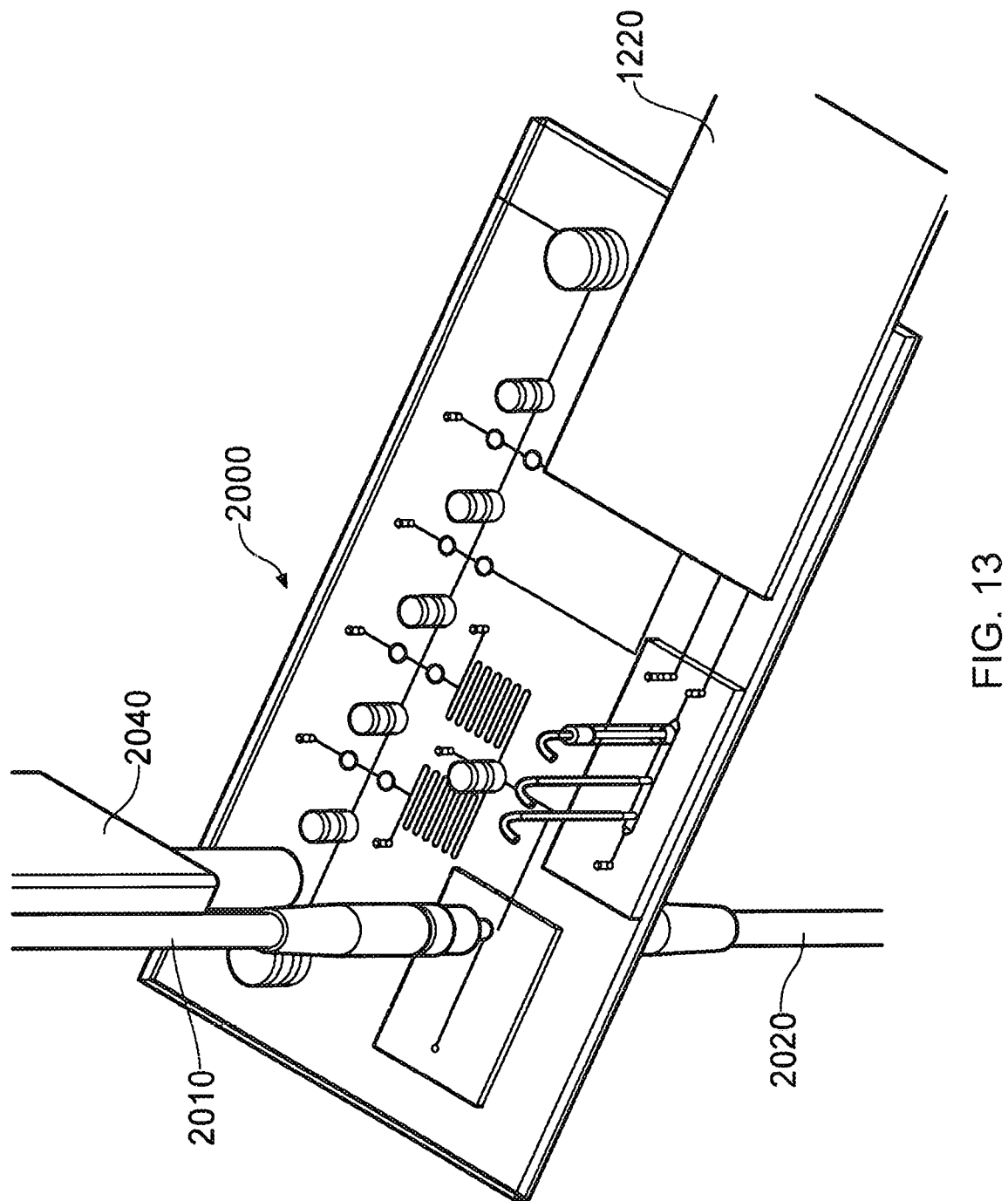
Figure 14:
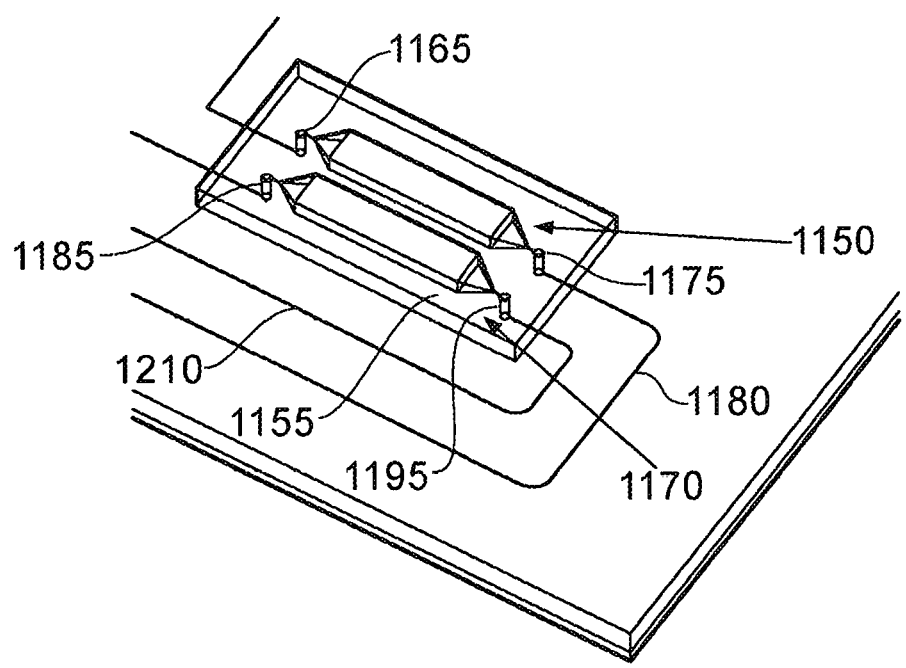
Figure 15:
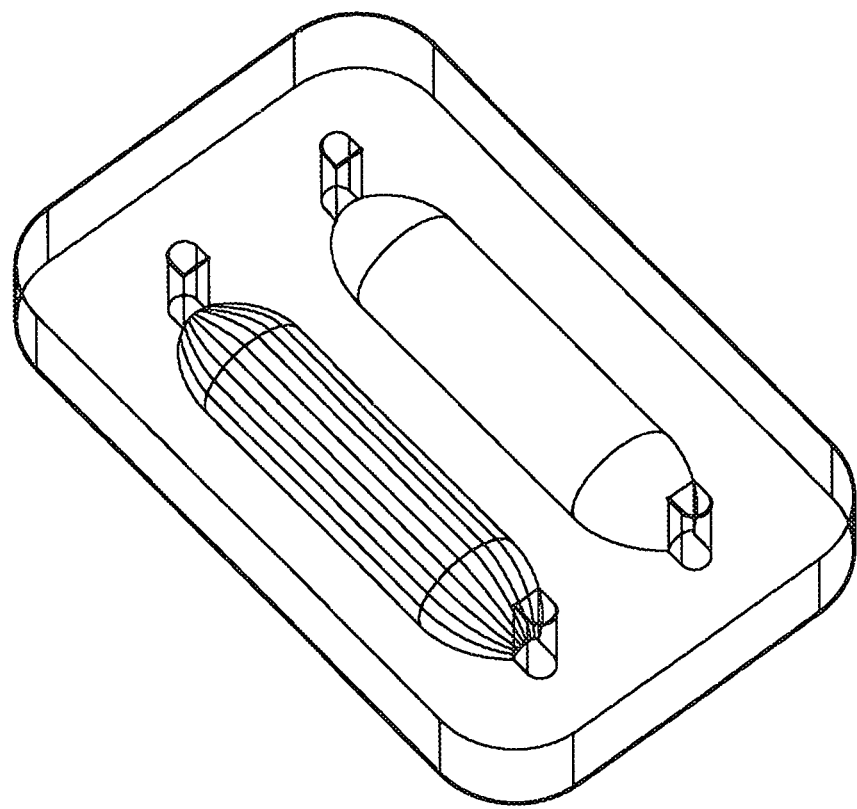
Figure 16:
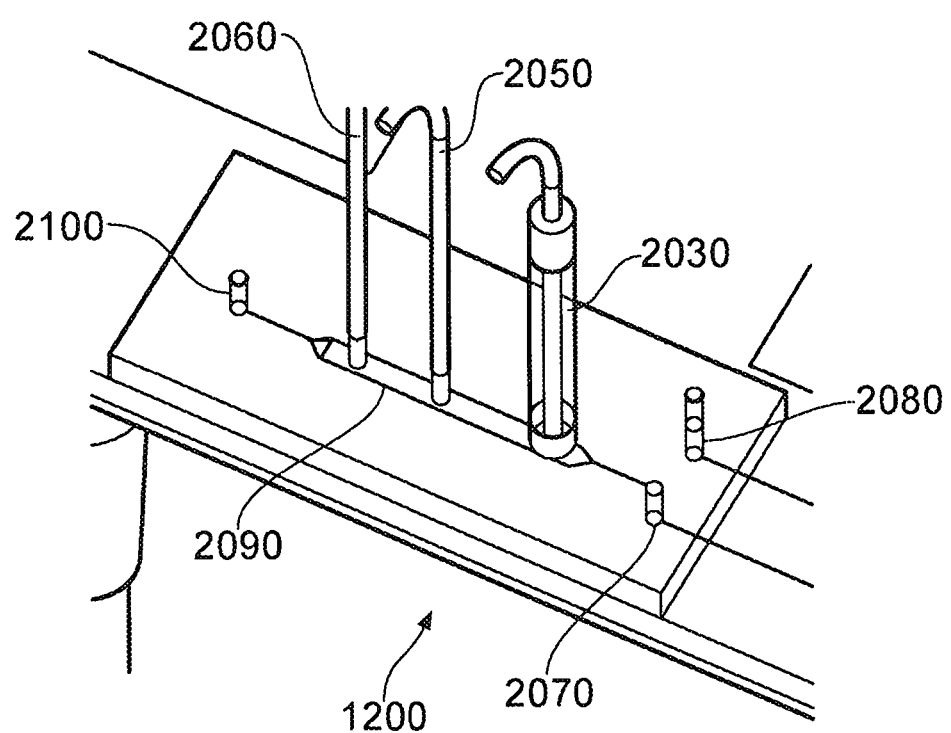
Figure 17A:
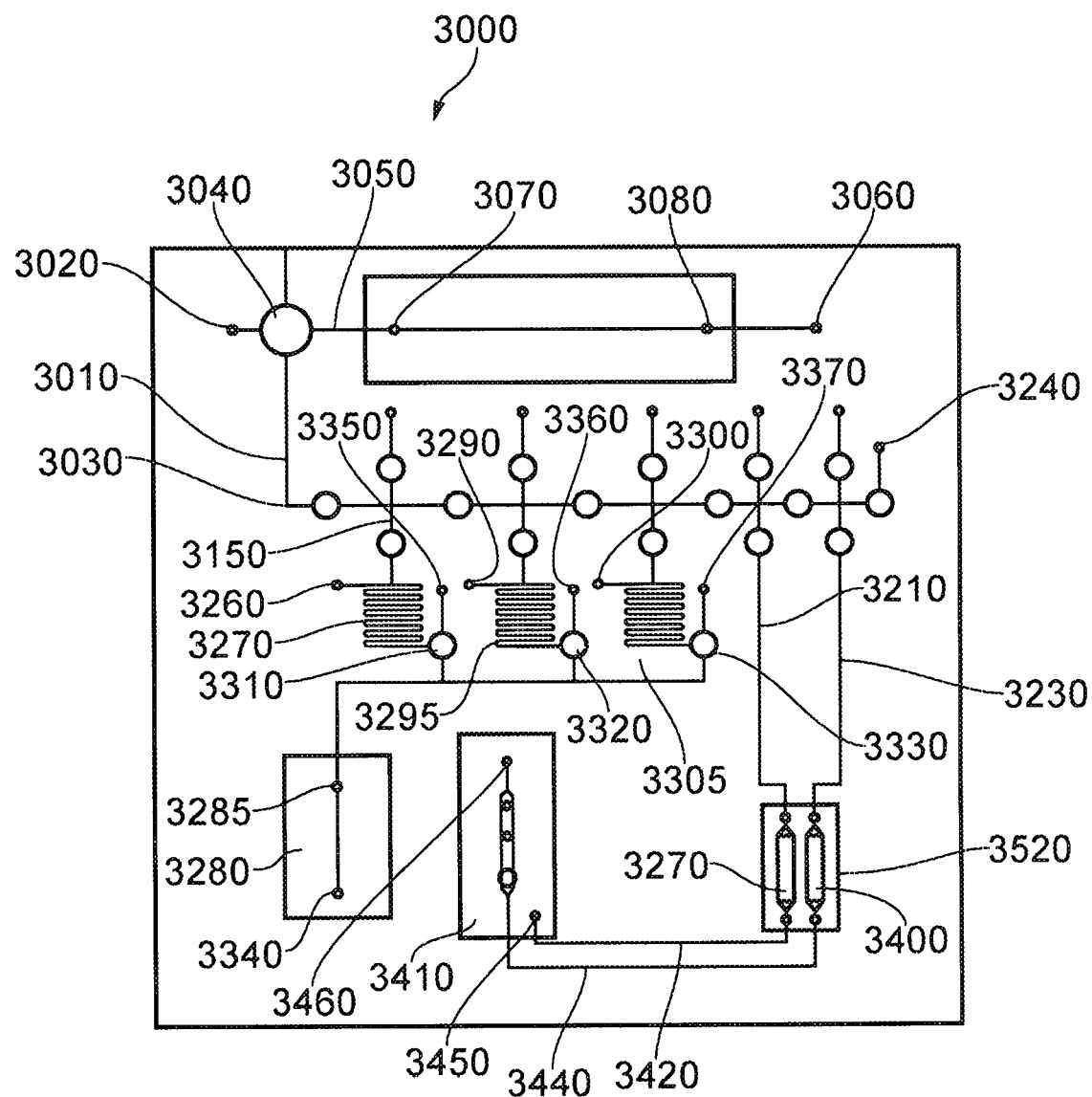
Figure 17B:
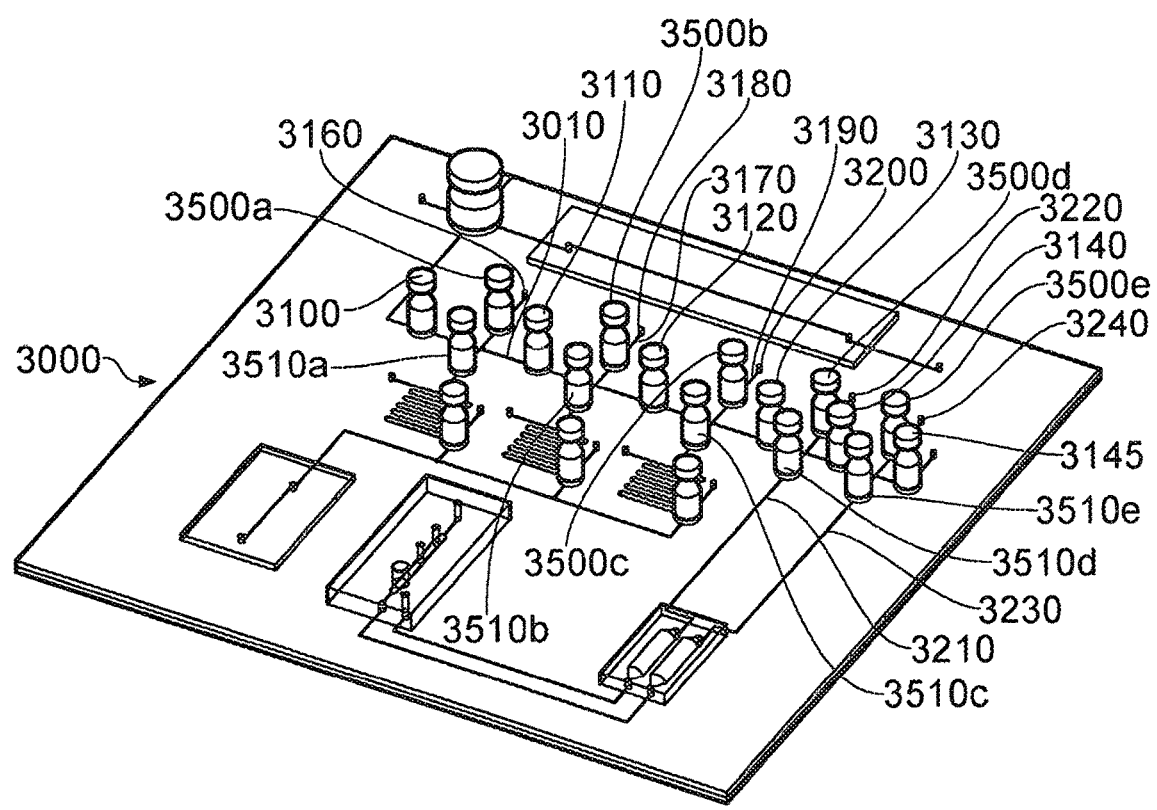
Figure 18:
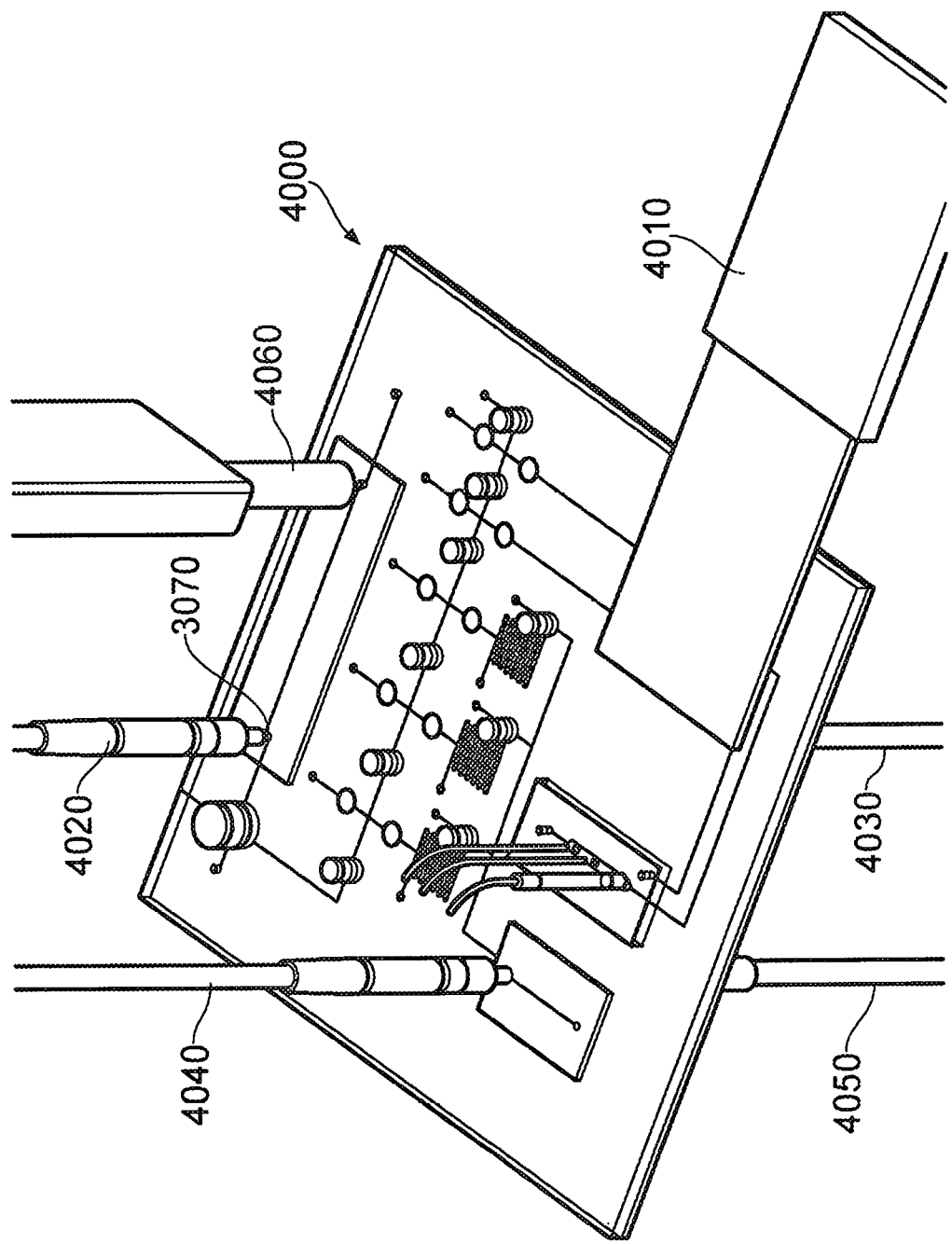
Figure 19:
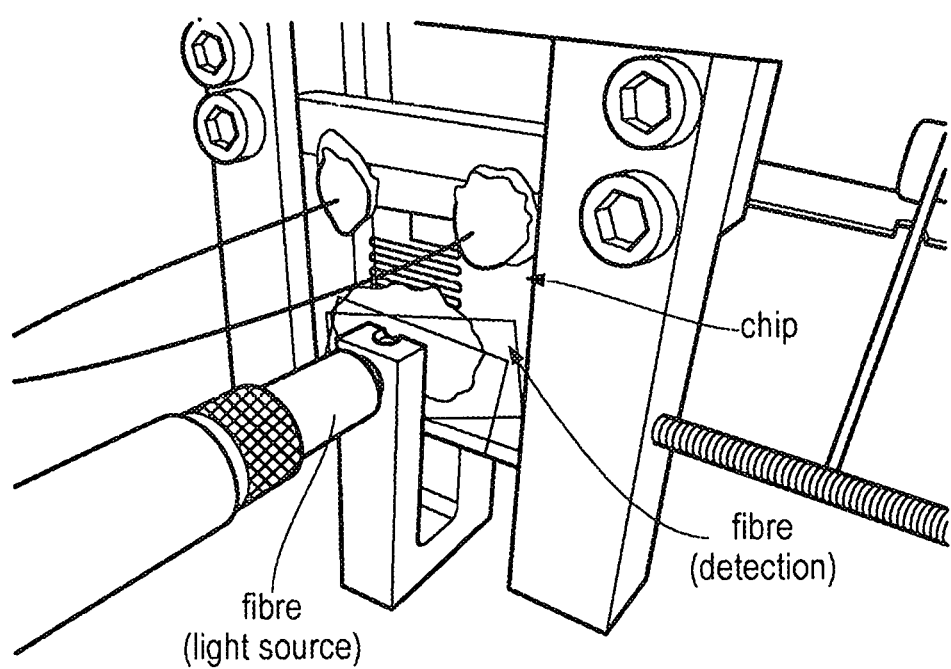
Figure 20:
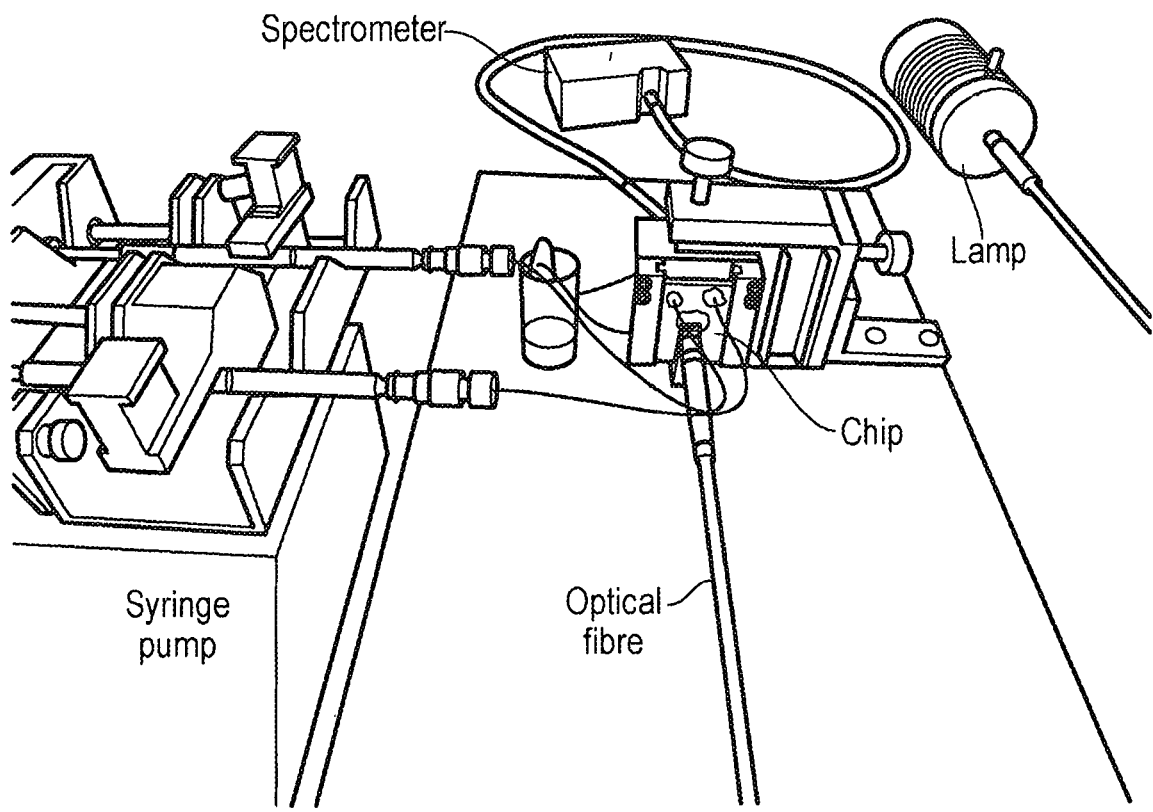
Figure 21:
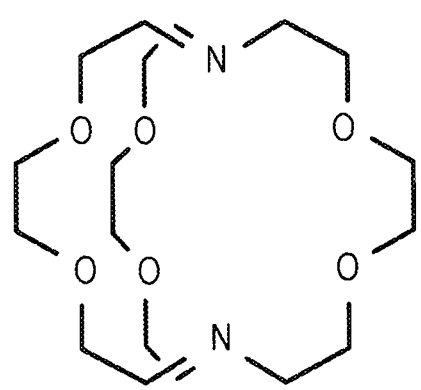
Figure 23:
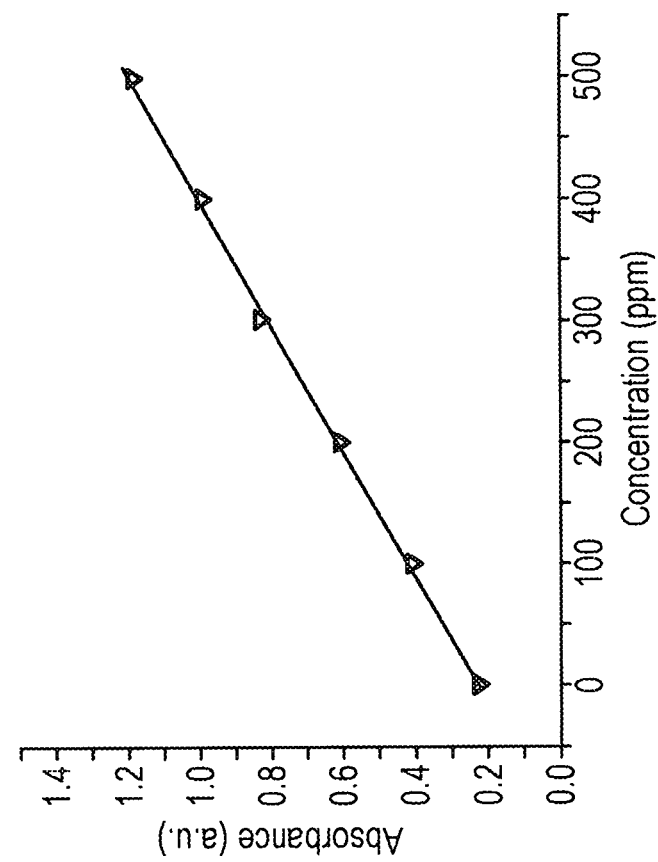
Figure 22:
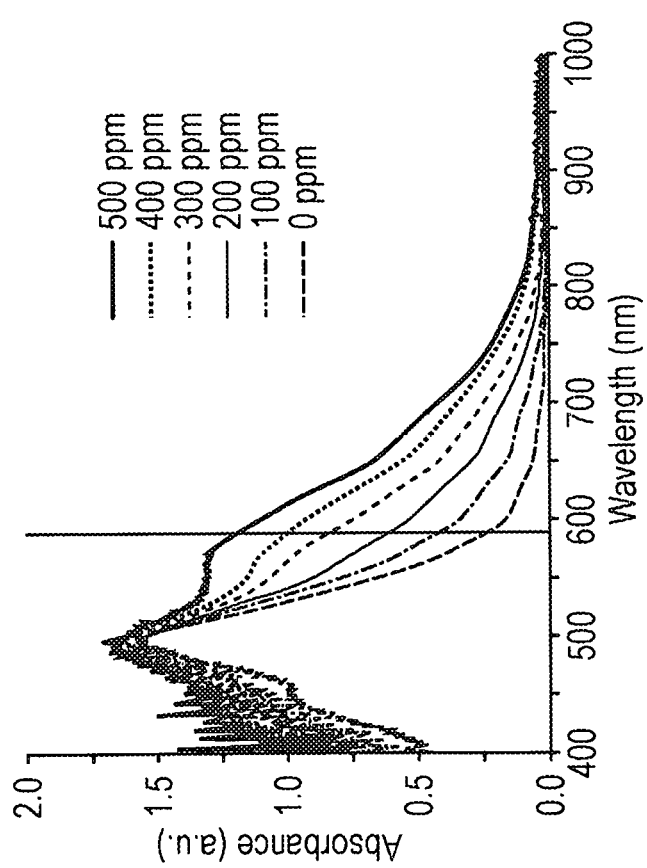
Figure 24:
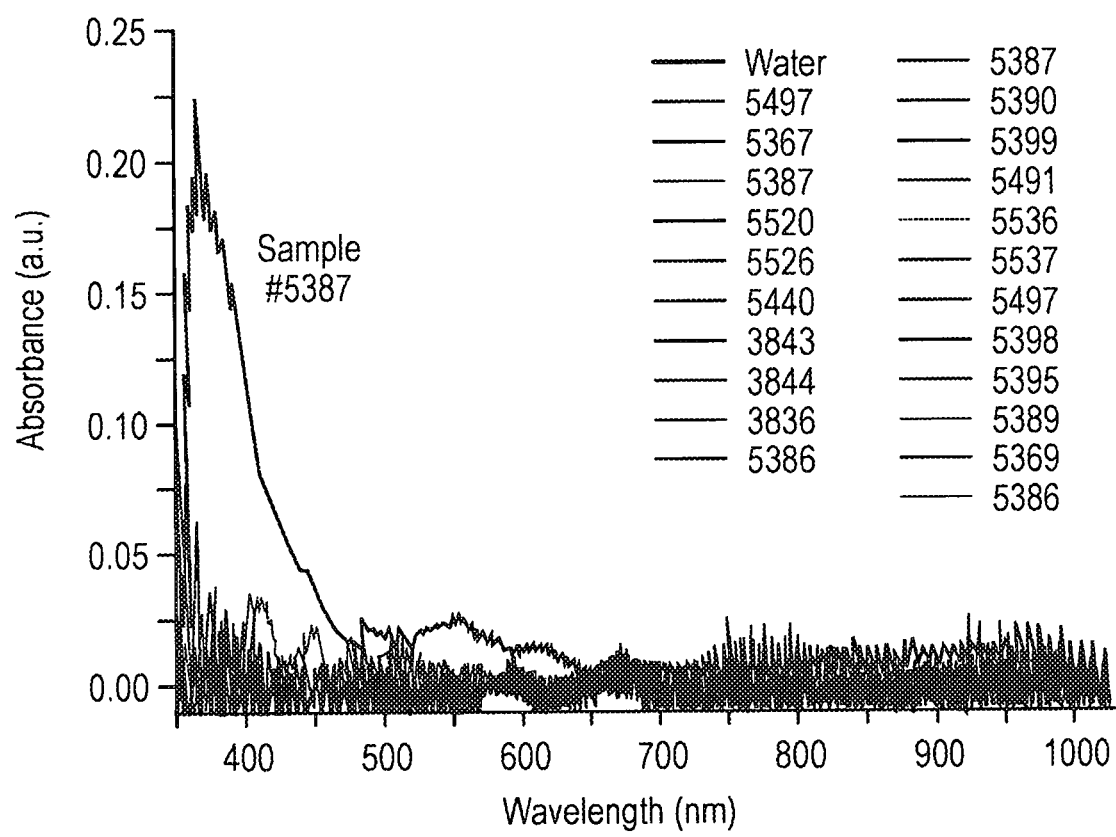
Figure 25:
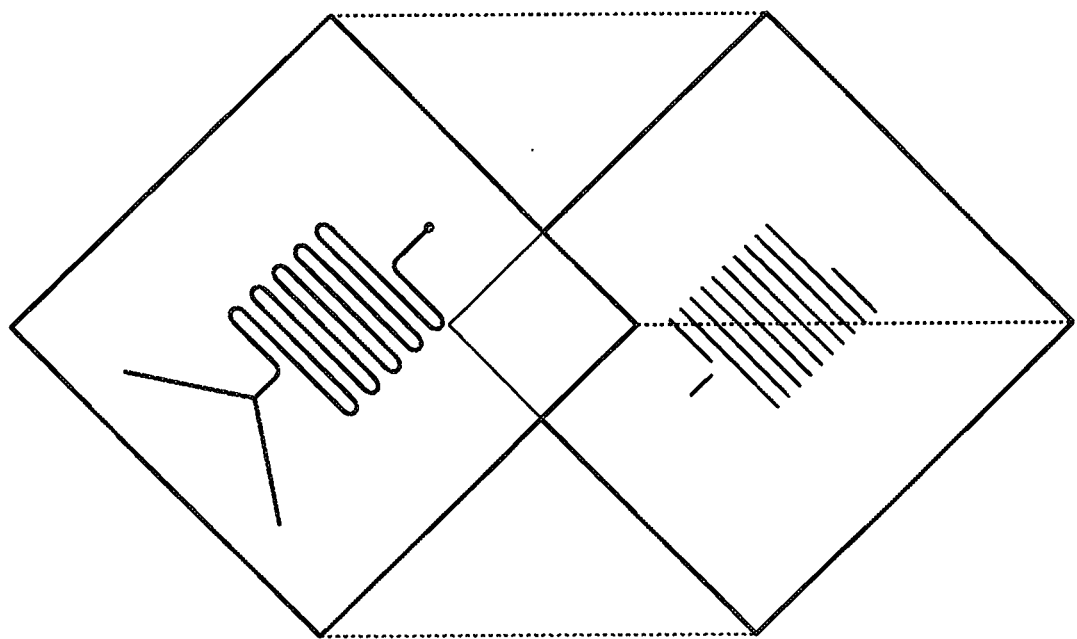
Figure 29:
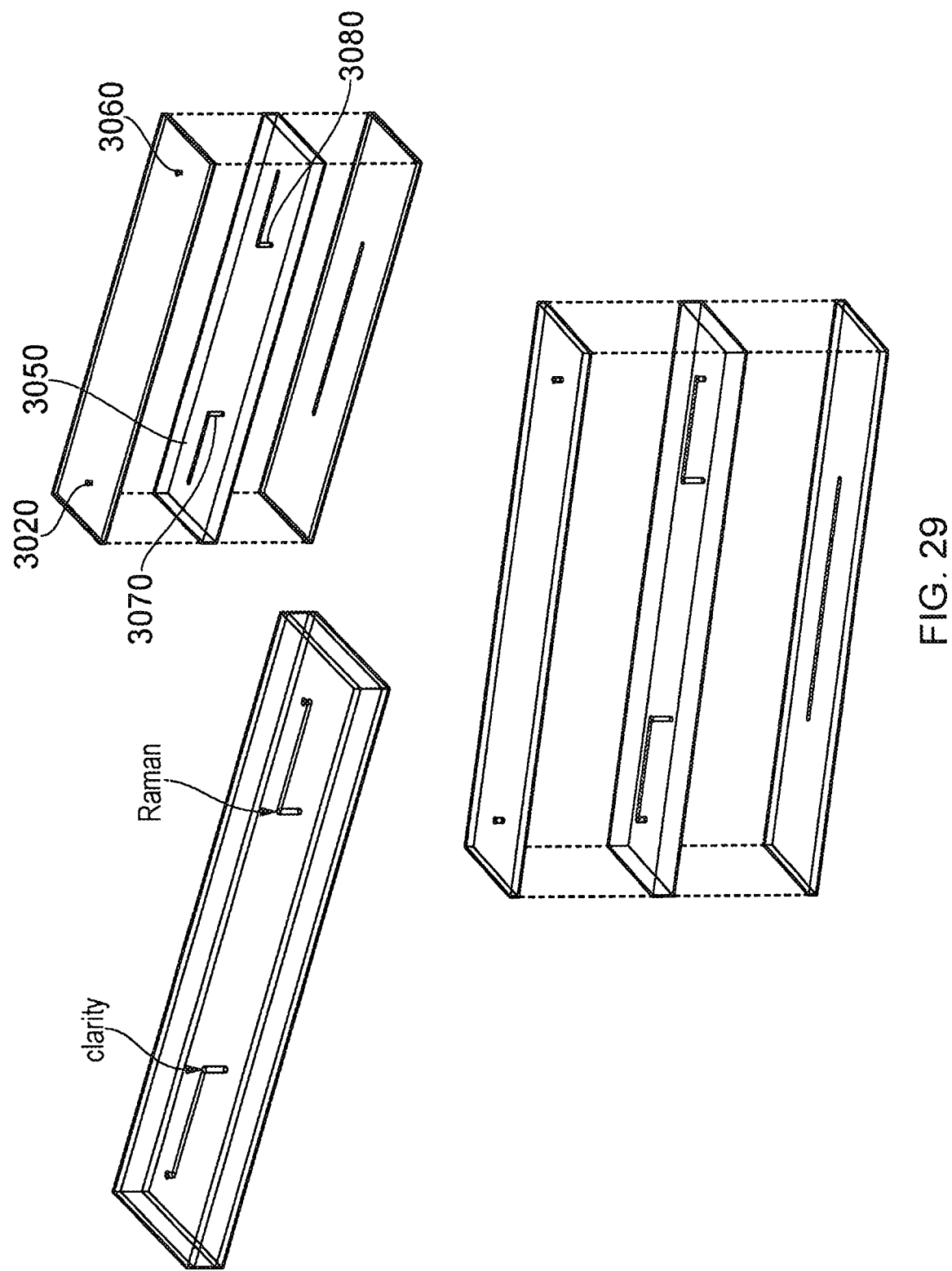
Figure 30:
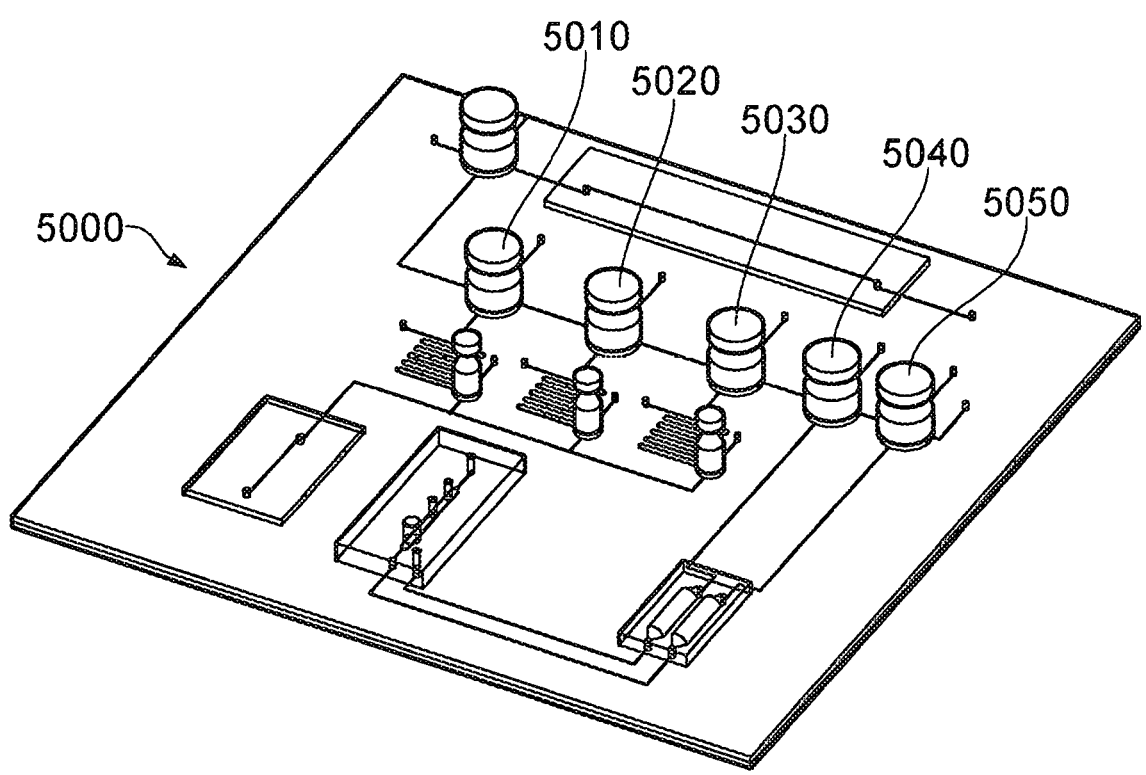
Figure 31:
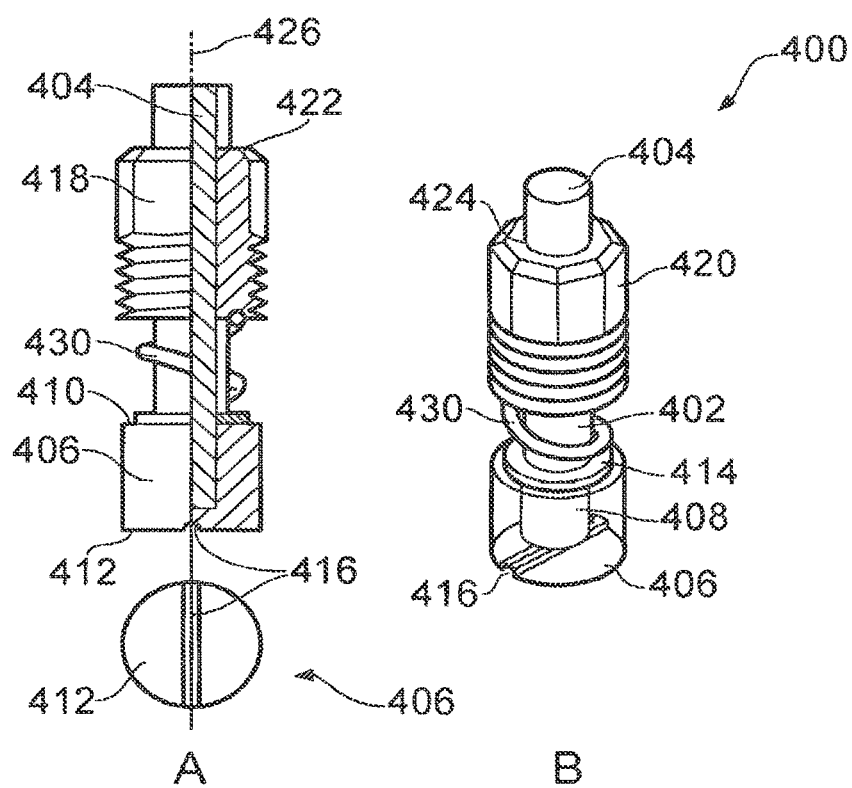
Figure 32:
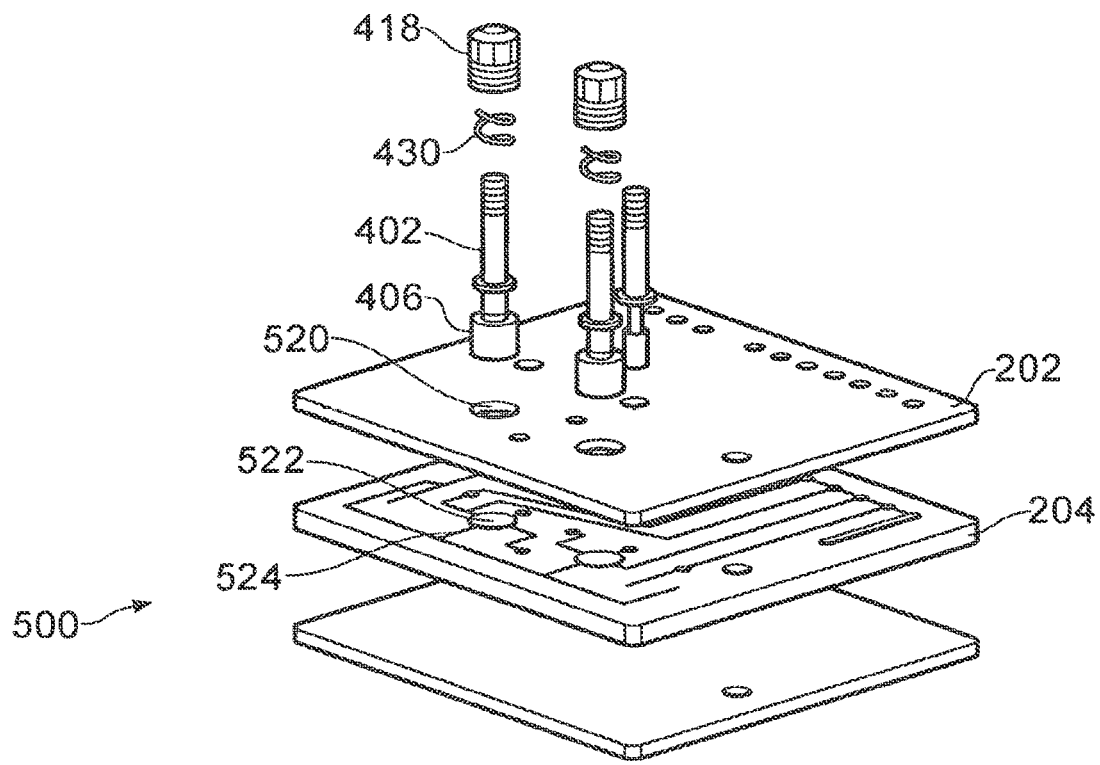
Figure 33:
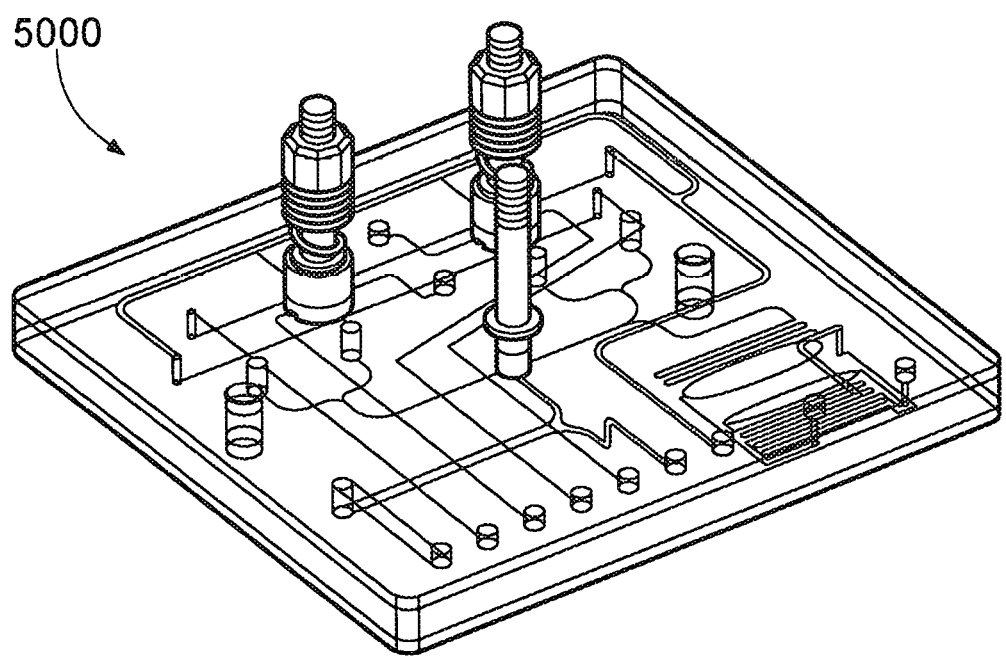
Figure 35:
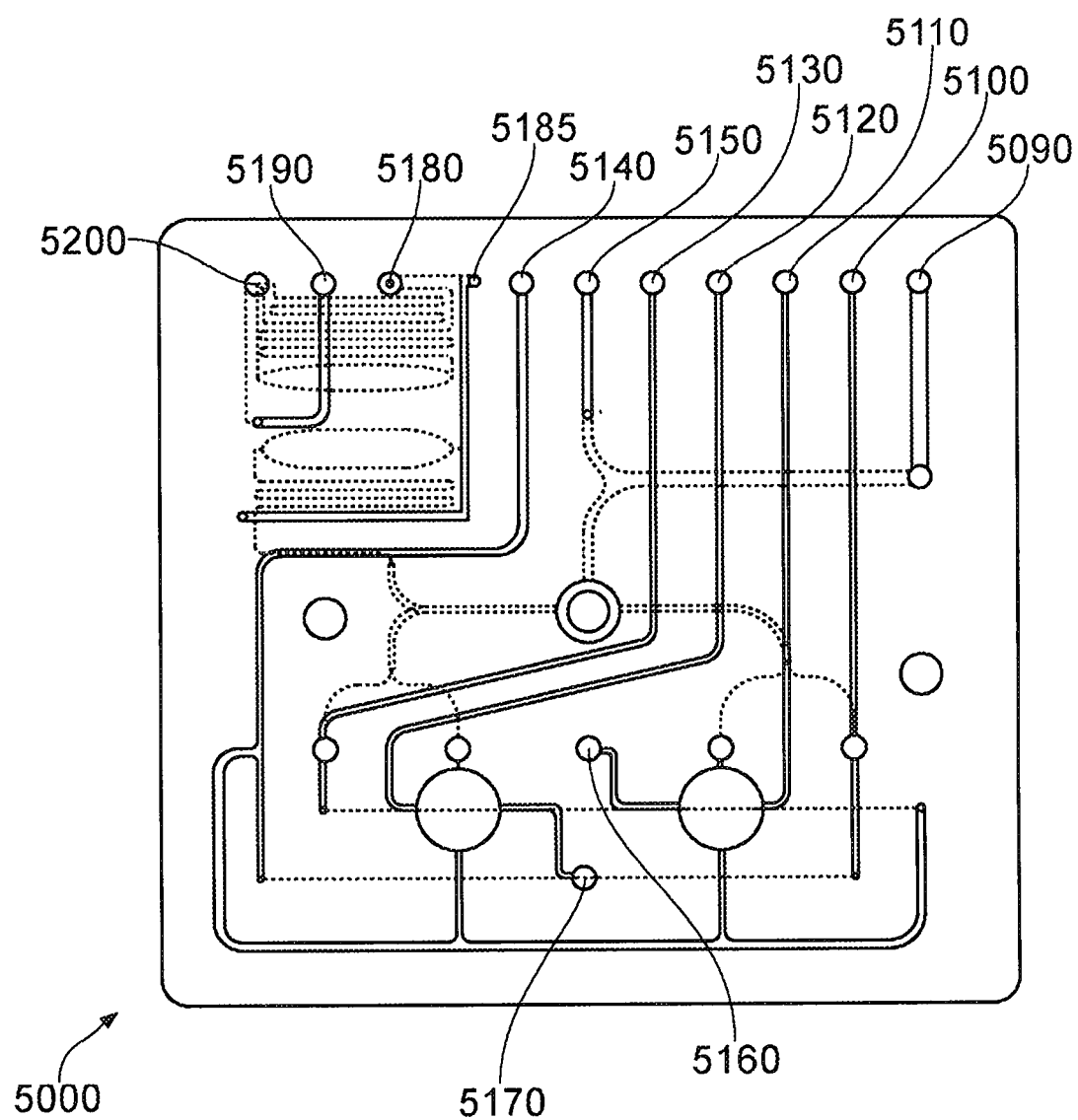
Figure 36:
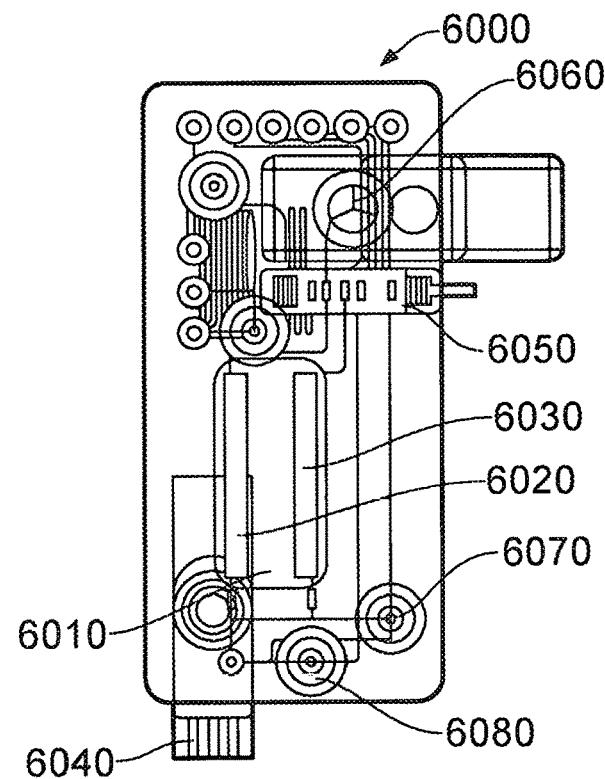
Figure 37:
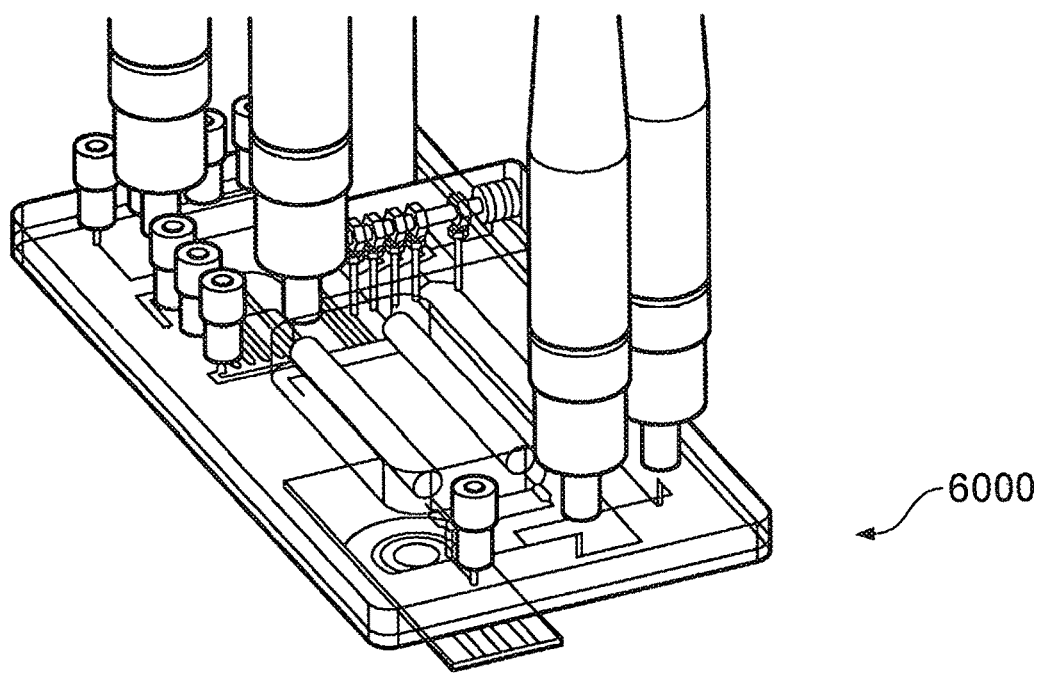

FIG. 10 is a radar plot of the absorbance values which are prepared at wavelengths of 520, 540, 560, 580, 600, 620 and 640 nm for each pH standard (pH 1-13). Plots of different shapes and sizes to which radar plots from samples can be compared to determine the pH, giving a more accurate reading of the pH compared to the V-shaped plot method;

FIG. 11 illustrates radar plots of each pH standard solution after reaction with a universal pH indicator solution;

FIG. 12 illustrates a microfluidic chip according to certain embodiments of the present invention;

FIG. 13 illustrates a system according to certain embodiments of the present invention;

FIG. 14 illustrates a module comprising a pair of monolithic bodies according to certain embodiments of the present invention;

FIG. 15 illustrates an alternative module comprising a pair of monolithic bodies according to certain embodiments of the present invention;

FIG. 16 illustrates a view of an electrochemical cell provided in the microfluidic chip according to certain embodiments of the present invention;

FIG. 17a illustrates a microfluidic chip according to certain embodiments of the present invention;

FIG. 17b illustrates an alternative view of the microfluidic chip of FIG. 17a;

FIG. 18 illustrates a system according to certain embodiments of the present invention;

FIG. 19 is a photo of a system according to certain embodiments of the present invention;

FIG. 20 is a photo of a system according to certain embodiments of the present invention;

FIG. 21 illustrates the chemical structure of Kryptofix 2.2.2;

FIG. 22 is a graph showing absorbance spectra of various Kryptofix 2.2.2 concentrations reacted with an iodoplatinate reagent;

FIG. 23 is a calibration graph based on the absorbance spectra illustrated in FIG. 22 at 590 nm wavelength;

FIG. 24 is a graph showing absorbance spectra of a number of sample solutions illustrating the optical clarity of each sample. Absorbance detection is used to determine pass/fail of the compound based on the optical clarity. A peak in absorbance corresponds to a failed dose ([$^{18}$F]FDG sample #5387) which exhibited a yellow-green colour to the eye;

FIG. 25 illustrates a pair of planar structures which form part of a chip according to certain embodiments of the present invention;

FIGS. 26a and b illustrate a pair of planar structures which are aligned such that herringbone structures of a lower planar structure are lined up with a serpentine channel of an upper planar structure;

FIGS. 27a and 27b are scanning electron micrographs of a herringbone mixing structure according to certain embodiments of the present invention;

FIGS. 28a and 28b are schematic representations of valve elements provided by certain embodiments of the present invention (channels not to scale). FIG. 28a illustrates a valve element according to certain embodiments of the present invention which acts to direct flow of a sample from an input into a sample channel or into a microchannel ("manifold") as described herein; and FIG. 28b illustrates an alternative valve element according to certain embodiments of the present invention which acts to direct flow of a sample from an input into a sample channel or into a microchannel ("manifold") as described herein;

FIG. 29 illustrates a detection zone according to certain embodiments of the present invention;

FIG. 30 illustrates an alternative embodiment of the microfluidic chip in which a single valve system is utilised;

FIG. 31 illustrates a valve assembly according to certain embodiments of the present invention;

FIG. 32 is an exploded view of a microfluidic chip according to certain embodiments of the present invention comprising a plurality of valve assemblies;

FIG. 33 is an isometric view of a microfluidic chip according to certain embodiments of the present invention;

FIG. 34a is a top view of the microfluidic chip shown in FIG. 33;

FIG. 34b is a cross sectional side view of the microfluidic chip shown in FIG. 33;

FIG. 35 is a schematic top view of the microfluidic chip of FIG. 33;

FIG. 36 is a schematic top view of a microfluidic chip according to certain embodiments of the present invention; and FIG. 37 is an isometric view of the microfluidic chip according to certain embodiments of the present invention.

In the drawings like reference numerals refer to like parts.

Aptly, the following definitions are used herein.

In certain embodiments of the present invention there is provided methods, microfluidic chips and systems for determining at least one characteristic of a sample comprising a compound for in vivo use. In one embodiment, the sample is formulated for in vivo use prior to testing on the chip and system of embodiments of the present invention. Aptly, the sample is an isotonic saline solution. In an alternative embodiment, the sample is formulated subsequent to testing on the chip and collection from the chip. As used herein, the term "sample" refers to a material to be investigated or analysed on a microfluidic chip. The sample may comprise a single component or a mixture of components. The sample comprises the compound for in vivo use and optionally other substances. Aptly, the sample may for administration to a patient without further formulation following its analysis using certain embodiments of the present invention.

As used herein, the term "compound for in vivo use" refers to any compound which is for administration to a patient in need thereof. The patient may be human or animal. The compound may be a pharmaceutical for prophylactic and/or therapeutic use.

In one embodiment, the compound for in vivo use is a radiopharmaceutical. In one embodiment the compound is a radiotracer. A "radiotracer" is a radiopharmaceutical having a largely unaltered metabolic pathway compared to the unlabelled analogue. It is therefore possible to follow and quantify processes on a particular metabolic pathway by detecting the radioactive decay of the labelling radioisotope.

It will be appreciated that the terms "radiotracer", "radiopharmaceutical", "PET tracer" and "SPECT tracer" as used herein are interchangeable and are exemplary and non-limiting. The mention of one term does not exclude substitution of the other terms in the described embodiment.

Aptly, the radiopharmeutical comprises a radioisotope selected from $^{89}$Zr, $^{64}$Cu, $^{18}$F, $^{99m}$Tc, $^{11}$C and $^{68}$Ga.

Radiotracers are used for diagnostic purposes. Examples of radiotracers include, but are not limited to, $^{18}$F-FLT ([$^{18}$F]fluoro thymidine), $^{18}$F-FDDNP (2-(I-{6-[(2-[$^{18}$F]fluoroethyl)(methyl)amino]2-naphthyl}ethylidene)malonitrile), $^{18}$F-FHBG (9-[4-[$^{18}$F]fluoro-3-(hydroxymethyl)butyl]guanine or [$^{18}$F]-penciclovir), $^{18}$F-FESP ([$^{18}$F]-fluoroethylspiperone), $^{18}$F-p-MPPF (4-(2-methoxyphenyl)-1-[2-(N-2-pyridinyl)-p-[$^{18}$F]fluorobenzamido]ethylpiperazine), $^{18}$F-FDG ([$^{18}$F]-2-deoxy-2-fluoro-D-glucose), $^{18}$F-FMISO ($^{18}$F-fluoromisonidazole) and $^{18}$F-sodium fluoride.

$^{18}$F-FDG is a radiolabelled sugar molecule. When used with PET imaging, images are produced that show the metabolic activity of tissues. In FDG-PET scanning, the high consumption of the sugar by tumour cells, as compared to the lower consumption by normal surrounding tissues, identifies these cells as cancer cells. FDG is also used to study tumour response to treatment.

Sodium fluoride is an imaging agent for PET imaging of new bone formation. It can assess changes both in normal bone as well as bone tumours. As a result, it can be used to measure response to treatment.

$^{18}$F-FLT is a radiolabeled imaging agent that is being investigated in PET imaging for its ability to detect growth in a primary tumor. Studies may also measure the ability of FLT with PET to detect tumor response to treatment.

$^{18}$F-FMISO is an imaging agent used with PET imaging that can identify hypoxia (low oxygen) in tissues. Tumours with low oxygen have been shown to be resistant to radiation and chemotherapy.

Alternatively, the radiotracer is a radiopharmaceutical which incorporates a radioisotope selected from the group consisting of $^{11}$C, $^{68}$Ga and $^{64}$Cu.

In one embodiment, the radiotracer is for example $^{68}$Ga-NOTA-bis (phosphonate), which can be used as a PET radiotracer for bone imaging, $^{68}$Ga-DOTATOC which can be used in PET imaging in patients with meningiomas and/or $^{68}$Ga-DOTATATE which can be used in PET imaging in malignant phaeochromocytomas.

A "radiopharmaceutical composition" comprises a radiopharmaceutical, or a pharmaceutically acceptable salt thereof, in association with a pharmaceutically acceptable adjuvant, diluent or carrier. In one embodiment, a radiopharmaceutical composition may comprise the radiopharmaceutical and a saline buffer.

The preparation of a radiopharmaceutical may comprise the following steps:

i) separation of a radioisotope from a sample;
ii) activation of the radioisotope, for example by solvent exchange;
iii) synthesis of the radiopharmaceutical, for example a radiotracer;
iv) separation of the radiopharmaceutical, for example a radiotracer, from a reaction mixture;
v) formulation of radiopharmaceutical into a radiopharmaceutical composition, for example a radiotracer formulated with a saline buffer;
vi) analysis of the radiopharmaceutical composition (quality control).

As used herein, the term "eluent" refers to the solvent that carries the analyte and any substances that the analyte is to be separated from. The eluent carries the sample.

An "eluate" is a mobile phase flowing out of a separation element as described herein, in particular, after the analyte has been separated from the sample.

The "mobile phase" comprises the phase flowing through the separation element. The mobile phase comprises the sample dissolved in the eluent flowing into a separation element e.g. a chromatographic body.

A "micropore" is a pore having a pore diameter of less than 2 nm, in particular between 0.1 nm and 2 nm. A "mesopore" is a pore having a pore diameter of between 2 nm and 50 nm. A "macropore" is a pore having a pore diameter greater than 50 nm, in particular between 50 nm and 1 μm.

Certain embodiments of the present invention relate to a microfluidic chip and system comprising such a chip. A fluid flow can be described as "microfluidic" (i.e. "microfluidic fluid flow") if a fluid passes through a channel having at least one dimension of less than 1 mm, in particular a channel having a dimension of less than 1 mm, e.g. less than 500 μm, less than 250 μm, less than 200 μm, or less than 150 μm. This creates laminar flow characteristics (generally having a Reynolds number of less than 100) where diffusion is the dominant cross stream chemical interaction. Consequently, microfluidic fluid flow occurs during the manipulation of small volumes, for example from 1 nl to 100 μl, within microstructured devices that features dimensions of the order of 10's to 100's micrometers.

A "microfluidic flow system" comprises a system having at least one channel for fluid flow, the channel having at least one dimension of less than one 1 mm, for example less than 500 μm, e.g. 300 μm, 200 μm, 150 μm, 100 μm, 50 μm or less. The microfluidic flow system comprises a microfluidic device but may also comprise other components that are in fluid communication with the microfluidic device.

In one embodiment, the system comprises one or more channels having a width of, for example, between about 100 μm to about 200 μm e.g. about 150 μm and a depth of for example about 50 μm deep.

A "microfluidic chip" can be identified by the fact that it has one or more channels with at least one dimension less than 1 mm, for example, less than 500 μm, e.g. 300 μm, 200 μm, 150 μm, 100 μm, 50 μm or less, in particular a channel having a dimension of less than 1 mm, e.g. for example, between about 100 μm to about 200 μm e.g. about 150 μm and a depth of for example about 50 μm deep. The microfluidic chip may be part of a microfluidic flow system. The one or more channels may form a fluid flow path in the chip.

As used herein, the term "microfluidic chip" refers to a device which can be used for synthetic or analytical purposes for samples having a volume of from about 10 nl and 10 ml. In one embodiment, the microfluidic chip is used to process, synthesize and/or analyze samples having a volume of between about 1 μl and 2000 μl e.g. about 1000 μl or less e.g. 500 μl or less. In one embodiment, the microfluidic chip is a microfluidic device and/or comprised within a microfluidic device. In certain embodiments, the microfluidic chip may comprise one or more separable modular components e.g. components comprising an electrochemical cell and the like. Aptly, the modular component may comprise a detection zone as described herein.

As used herein, the term "pathlength" refers to a distance travelled by light through a fluid e.g. a sample. Aptly, the microfluidic chip comprises a detection channel which is of a length suitable to provide a pathlength for a spectroscopic technique.

Aptly, the detection channel is at least 2 mm in length, e.g. 2.5 mm, 3 mm, 3.5 mm or greater.

The Reynolds number which is used to characterise microfluidic flow (i.e. the flow of a fluid through a microfluidic channel is calculated according to equation 1:

$$\mathrm{Re} = \frac{LV_{avg}\rho}{\mu} \qquad \text{equation 1}$$

wherein:
L is the most relevant length scale;
μ is the viscosity;
ρ is the fluid density; and
$V_{avg}$ is the average velocity of the flow.

For many microchannels:

$$L = 4A/P \text{ wherein:} \qquad \text{equation 2}$$

A is the cross sectional area of the channel; and
P is the wetted perimeter of the channel.

Due to the small dimensions of the channels in a microfluidic device, $R_e$ is usually less than 100, in particular less than 1.0. Fluid flow with a Reynolds number of this magnitude is completely laminar with very little or no turbulence such that molecular transport is relatively predictable.

As described herein, certain embodiments of the present invention relate to the analysis of compounds which are for in vivo administration. One embodiment, the compound is a radiopharmaceutical such as for example [$^{18}$F]FDG.

FIG. 1 comprises a table which lists some of the criteria specified by the British Pharmacopoeia 2012 that must be satisfied for an exemplary radiotracer ([$^{18}$F]FDG). It will be understood by the person skilled in the art that embodiments of the present invention are not limited to the testing of [$^{18}$F]FDG. For example, certain embodiments of the present invention relate to devices, systems and methods which perform quality control testing of other radiotracers and/or other compounds which are for in vivo administration. In certain embodiments of the present invention, the devices, systems and methods are for use to determine at least one characteristic of a pharmaceutical compound.

In one embodiment, following purification, QC tests are performed on a sample of [$^{18}$F]FDG in order to ensure that all impurities have been removed and that the properties of the dose are suitable for injection. As used herein, the terms "[$^{18}$F]FDG" and "FDG" are interchangeable and relate to the compound 2-[$^{18}$F]fluoro-2-deoxy-D-glucose. A summary of the process for preparing [$^{18}$F]FDG is as follows:

[$^{18}$F]FDG is usually synthesized by way of nucleophilic substitution (Hamacher et al.) and aptly, the procedure follows the steps of:

1. [$^{18}$F]fluoride generation by proton bombardment of $^{18}$O-enriched cyclotron via a cyclotron;

2. Pre-concentration of aqueous [$^{18}$F]fluoride, e.g. an ion exchange column, or electrode trapping.
3. Release of [$^{18}$F]fluoride in acetonitrile containing addition of phase transfer catalyst (typically Kryptofix 2.2.2) and potassium carbonate.
4. Radiolabelling reaction of mannose triflate with [$^{18}$F] fluoride via $S_N2$ nucleophilic substitution, producing the acetylated form of [$^{18}$F]FDG (i.e. unhydrolysed [$^{18}$F]FDG, also referred to as acetylated-[$^{18}$F]FDG (ACY-[$^{18}$F]FDG) or 2-[$^{18}$F]fluoro-1,3,4,6-tetra-O-acetyl-D-glucose ([$^{18}$F]TAG)).
5. Solvent exchange from acetonitrile to water.
6. Hydrolysis of acetylated-[$^{18}$F]FDG to [$^{18}$F]FDG, either by acid hydrolysis (HCl) or base hydrolysis (NaOH).
7. Purification of the crude [$^{18}$F]FDG mixture, e.g. via solid-phase extraction (SPE) cartridge(s).
8. Formulation of the [$^{18}$F]FDG dose as an isotonic saline (sodium chloride) solution.

Prior to administration to a patient, the batch of [$^{18}$F]FDG has to undergo a number of quality control tests to ensure it meets the necessary safety requirements. Aptly, certain embodiments of the present invention provide a microfluidic system which can be used to perform the quality control tests of microfluidic quantities of a compound, e.g. [$^{18}$F]FDG. Certain embodiments of the present invention provide a measurement value which can be used to determine the characteristic of the sample. The measurement value can then be compared to a predetermined corresponding criterion value to determine whether the sample is suitable for administration to a patient. The predetermined corresponding criterion value can be identified using known literature such as for example although not limited to the current British Pharmacopoeia, US Pharmacopeia, European Pharmacopoeia, International Pharmacopoeia, and the like.

Aptly, certain embodiments of the present invention test the "appearance" and/or clarity of a sample comprising [$^{18}$F]FDG. In the BP, it is stated that the appearance of an [$^{18}$F]FDG should be a "clear, colourless or slightly yellow solution". However, it is generally considered that a slightly yellow solution is likely to contain impurities. Furthermore, other pharmacopoeias state that [$^{18}$F]FDG should be "colourless and free from particulate matter". Thus, it is often proposed that an [$^{18}$F]FDG solution should be clear, colourless, and free from particulate matter. Certain embodiments of the present invention determine the appearance of a compound for in vivo use e.g. a radiopharmaceutical and aptly determine if the compound is suitable for administration to a patient.

In addition, the sample of the compound e.g. a fluorine containing compound such as [$^{18}$F]FDG should be tested for the presence and amount of chemical impurities. In terms of chemical purity testing, CIDG refers to 2-chloro-2-deoxy-D-glucose, an impurity that can be present particularly when using acid hydrolysis in which a chloride atom takes the place of the [$^{18}$F]fluoride label. A further source of chloride may be an anion exchange cartridge used to pre-concentrate the [$^{18}$F]fluoride label in many systems, depending on the counter ion present on the cartridge resin.

Aptly, ACY-[$^{18}$F]FDG or alternatively ACY-FDG refers to the acetylated/unhydrolysed form of [$^{18}$F]FDG, which is 2-[$^{18}$F]fluoro-1,3,4,6-tetra-O-acetyl-D-glucose (also referred to as [$^{18}$F]TAG), while partially hydrolysed ACY-[$^{18}$F]FDG can also be present.

[$^{18}$F]FDM is 2-[$^{18}$F]fluoro-2-deoxy-D-mannose, a byproduct that can be produced during the [$^{18}$F]FDG synthesis process, and which can also be present in fully or partially hydrolysed form (ACY-[$^{18}$F]FDM).

Aptly, certain embodiments of the present invention determine the presence and/or quantity of impurities in the sample. In one embodiment, the chip, system and/or method may be used to determine the presence and/or quantity of residual solvents in a sample comprising the compound.

In one embodiment, the sample may comprise acetonitrile and/or ethanol. Aptly, the apparatus, systems and methods described herein may be used to determine the presence and/or quantity of acetonitrile and/or ethanol in the sample.

Acetonitrile is used as the solvent during [$^{18}$F]fluoride labelling. Ethanol is often used for cleaning systems and for conditioning of purification columns. Acetonitrile and ethanol concentrations must be <410 ppm and <5000 ppm respectively according to the British Pharmacopoeia (BP) and European Pharmacopoeia (EP).

In one embodiment, other impurities may be determined by the chip, system and/or method. Aptly, the impurity is a solvent. Aptly, the impurity is selected from diethyl ether, acetone and methanol. The method may also detect the presence and/or concentration of [$^{18}$F]fluoride and/or D-glucose.

pH

According to the BP, the pH of a dose of a compound for in vivo use, e.g. a [$^{18}$F]FDG dose should be in the range of 4.5 to 8.5, although this range can vary in other pharmacopoeias (e.g. pH 4.5 to 7.5 in the USP).

Kryptofix 2.2.2

The aminopolyether, Kryptofix 2.2.2 (4,7,13,16,21,24-hexaoxa-1,10-diazabicyclo[8.8.8]hexacosane), also known as cryptand 2.2.2, is a phase transfer catalyst used during [$^{18}$F]FDG synthesis. It incorporates a potassium ion into its cage-like structure, preventing the formation of potassium [$^{18}$F]fluoride in acetonitrile and thus leaving the [$^{18}$F]fluoride ion to react with the mannose triflate molecule by nucleophilic substitution. However, while an important aspect of the synthesis, Kryptofix 2.2.2, hereafter referred to as K222, is also very toxic, causing apnoea, ptosis and convulsions in patients, while the intravenous $LD_{50}$ in rats is 35 mg/kg. Thus, its removal from [$^{18}$F]FDG is important and its concentration in a dose must be determined.

The limit of K222 that can be present in [$^{18}$F]FDG depends varies between pharmacopoeias, with the EP and BP stating a limit of 2.2 mg per volume of dose (e.g. the maximum amount of K222 that could be in a 10 mL dose would be 2.2 mg, which would be equivalent to 220 µg mL$^{-1}$), while in the USP the limit is set at 50 µg mL$^{-1}$. K222 is essential for many radiolabelling processes involving [$^{18}$F]fluoride, and so is not limited to only [$^{18}$F]FDG.

While Kryptofix 2.2.2, referred to as "aminopolyether" in the BP, is usually the phase transfer catalyst of choice in the synthesis of [$^{18}$F]FDG by nucleophilic substitution, other catalysts such as tetrabutylammonium and 4-(4-methylpiperidin-1-yl)pyridine can also be employed instead, hence their inclusion in the BP. However, it is worth noting that the BP states that specific tests do not need to be performed if there is no source of the potential impurity (e.g. the test for tetrabutylammonium is not required if Kryptofix 2.2.2 is used as the phase transfer catalyst).

Bacterial Endotoxin

In the case of [$^{18}$F]FDG and other radiopharmaceuticals, the presence and/or quantity of bacterial endotoxin must be determined prior to the radiopharmaceutical being deemed safe for administration to a patient. Bacterial endotoxins can be introduced into the radiopharmaceutical manufacturing process by way of for example non sterile tubing, containers, chemicals and/or water.

Each of the above mentioned characteristics can be determined using certain embodiments of the present invention. Once the characteristics of the sample have been determined, a decision can be made as to whether or not the compound is suitable for in vivo use. In certain embodiments of the present invention, the sample has a volume which is only a small percentage greater than a single unit dose of the compound. Thus, a single unit dose of the sample comprising the compound exits the chip and is suitable for administration to a patient, providing all of the sample's characteristics meet the stated requirements for in vivo use.

Figure 2:
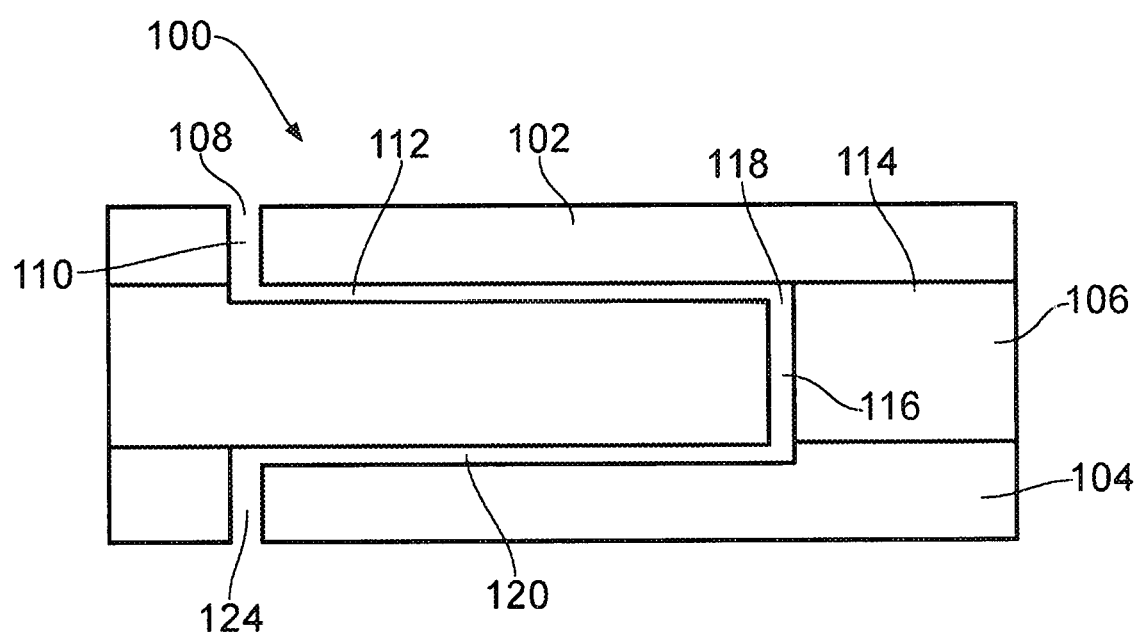
FIG. 2 is a side view of a microfluidic chip in accordance with certain embodiments of the present invention.

Turning now to the embodiments illustrated in the Figures:

FIG. 2 is a side view of a microfluidic chip 100 according to certain embodiments of the present invention. The chip 100 illustrated in FIG. 2 comprises an upper planar structure 102, a lower planar structure 104 and an intermediate planar structure 106. The chip may comprise a fluid flow path which is composed of one or more microchannels as described below. The upper, lower and intermediate planar structures can be fabricated individually and subsequently adhered or otherwise secured together.

Aptly, the chip of certain embodiments of the present invention is prepared using photolithography and wet etching procedures. Aptly, glass wafers featuring a chromium layer and a photoresist layer are exposed to UV light through a photomask featuring a channel design. The region of photoresist exposed to light becomes soluble in photodeveloper solution, which is then used to strip away the exposed region, revealing the channel design on the chromium layer. The exposed chromium is then etched away, leaving the channel design visible on the glass. A solution of 1% hydrofluoric acid can then be used to etch the channel design into the glass, after which access holes can be drilled into the glass. The remaining photoresist and chromium layers are then removed. The plate is then thoroughly cleaned and has an upper planar structure aligned with it. Both plates are placed in a furnace with a steel weight on top, and left for 4 hours at approximately 585° C. to allow the plates to thermally bond.

In certain embodiments the microfluidic device comprises three layers fabricated in glass (B270 coated with chromium and photoresist layers, Telic, USA) using the standard photolithography and wet etching procedures described above.

In certain embodiments which comprise a detection channel as described herein, the detection channel is formed by way of a hole being drilled into a middle (intermediate) planar structure. Once the photoresist and chromium layers are removed, the three plates are washed thoroughly and then carefully aligned to match up (i) any inlet holes with any serpentine channel inlets, (ii) herringbone structures (if present) with the serpentine channel and (iii) the one or more detection channel (in the middle plate) with an outlet channel on the lower planar structure. They are then taped together and placed in the furnace at a temperature of approximately 585° C. for 4 h to thermally bond all three plates together.

In one embodiment, the upper and the lower planar structures are 1 mm thick and approximately 30 mm by 30 mm. Other dimensions are encompassed by embodiments of the present invention. In one embodiment, the intermediate planar structure 106 has a thickness of between approximately 2 mm to 5 mm. Aptly, the intermediate planar structure has a thickness of between 2 mm to 4.5 mm. Aptly, the intermediate planar structure has a thickness of between 3 mm to 4 mm.

Microfluidic chips of other dimensions are also envisaged and encompassed by embodiments of the present invention.

The total volume capacity of the chip may vary depending on its use. Aptly, the chip has a total fluid volume capacity of no more than about 100 µl. Aptly, the chip has a total fluid volume capacity of 85 µl or less. In one embodiment, the chip has a total fluid volume capacity of 75 µl or less, e.g. 70 µl or less, 60 µl or less or 50 µl or less. In certain embodiments of the present invention, the chip may have a total volume of 10 µl or less e.g. 5 µl or less. In certain embodiments, the chip has a total fluid volume capacity of less than 2 µl.

Each of the planar structures is made from a material through which light may be transmitted. For example, each planar structure may be formed from glass, plastic, quartz or a combination of these materials. In one embodiment, one or more planar structure is formed from glass.

The upper planar structure comprises an inlet port 108. The inlet port is connected to a short microchannel 110 which extends through the thickness of the upper planar structure. The short microchannel 110 is connected to a horizontal microchannel 112 which is provided on an upper surface 114 of the intermediate planar structure planar structure. The microchannel 112 may have dimensions of for example a depth of approximately 50 µM, a width of approximately 150 µM and a length of approximately 15 mm. In alternative embodiments, the microchannel may comprise different dimensions.

In an alternative embodiment, the microchannel 112 may be provided on a lower surface of the upper planar structure.

The microchannel 112 of the upper planar structure meets a detection channel 116 at a junction 118. The detection channel 116 is a microchannel which extends at least partially or wholly through the thickness of the intermediate planar structure 106 and which is provided at generally 90 degrees to the microchannel 112. In the embodiment illustrated in FIG. 2, the detection channel extends from an upper surface of the intermediate planar structure to a lower surface of the intermediate planar structure. The detection channel illustrated in FIG. 2 may be fabricated by way of drilling a hole of suitable dimensions through a planar structure prior to the intermediate planar structure being sandwiched between the upper and lower planar surfaces and secured to form the microfluidic chip.

The detection channel 116 acts as a path length between a source e.g. a light source and a detector. Further details of the path length, the source and the detector are provided below.

A bottom-most end of the detection channel is connected to a further microchannel 120 at a junction. The microchannel 120 is generally horizontal and provided at a surface between an upper surface of the lower planar structure 104 and the lower surface of the intermediate planar structure 106.

The microchannel 120 may be connected to an outlet 124 for exiting the sample from the chip. The microchannels 110, 112, 120 and the detection channel together form a fluid flow path.

Figure 3:
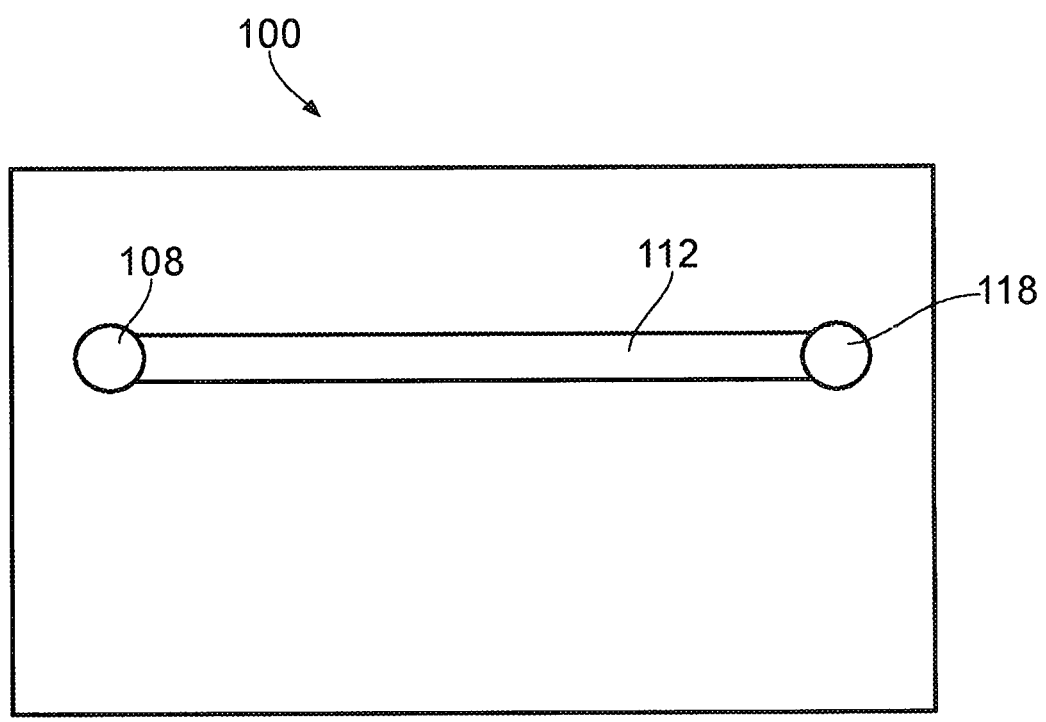
FIG. 3 is a top view of a microfluidic chip in accordance with certain embodiments of the present invention.

FIG. 3 illustrates a top view of the chip 100 of FIG. 2.

Figure 4:
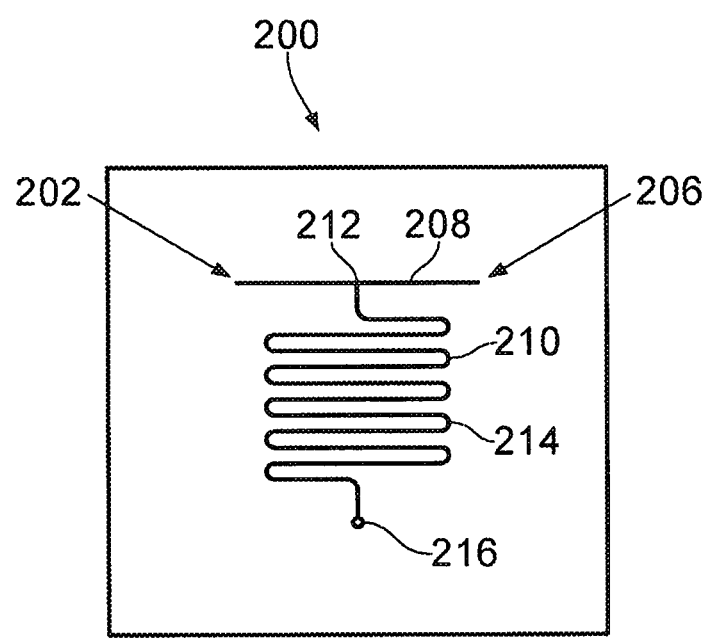
FIG. 4 is a top view of a microfluidic chip in accordance with certain embodiments of the present invention.

FIG. 4 illustrates an alternative embodiment of a microfluidic chip 200. The microfluidic chip 200 comprises an inlet port 202 for introduction of a sample to be supplied to the chip. The inlet port 202 is provided on an upper surface of the chip. The upper surface may be provided by an upper planar structure in a layered chip as described above. In alternative embodiments, the chip may be formed from a single component and therefore only has a single layer. Such chips may be formed by techniques known in the art such as, for example, laser ablation, stereolithography and 3D printing.

The microfluidic chip 200 also comprises a second inlet port 206. The second inlet port can be used to introduce one or more reagents to the chip. The second inlet port 206 is in fluid communication with the first inlet port via a first microchannel 208. The microchannel 208 is connected to a further microchannel 210. In the illustrated embodiment the further microchannel 210 is connected to the first microchannel at a junction 212 which is generally at a midpoint of the first microchannel between the first inlet port and the second inlet port.

The further microchannel 210 comprises a serpentine pathway portion 214 in which the reagent and the sample mix prior to detection taking place. Thus, the further microchannel may be referred to as a mixing microchannel.

The mixing channel is connected to a detection channel 216 which is provided at approximately right angles to the mixing channel and extending at least partially through the thickness of the chip.

Figure 6A:
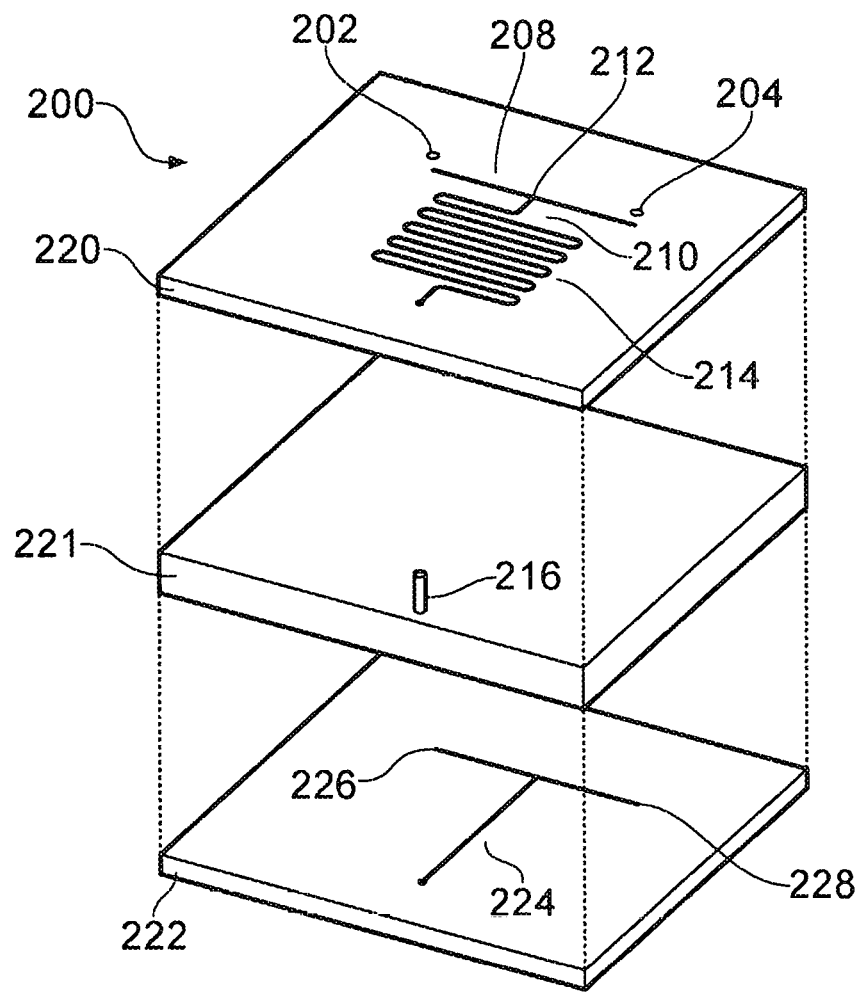
FIG. 6a is an exploded side view of a microfluidic chip in accordance with certain embodiments of the present invention.

FIG. 6a illustrates the microfluidic chip of FIG. 4 in an exploded view. As shown in FIG. 6a, the detection channel is provided as a bore in an intermediate planar structure 221 positioned between an upper plate 220 and a lower plate 222.

The lower plate 222 is provided with a T-shaped microchannel 224 which is in fluid communication with an outlet 226 for the sample/reagent mixture to be removed from the chip. In the illustrated embodiment, the chip comprises two outlets (226, 228). In alternative embodiments, the chip may comprise a single outlet and the microchannel 224 may be linear or L-shaped accordingly.

The chip, or a system comprising the chip, may also comprise one or more driving elements (not shown) such as for example syringe pumps to move the reagent and the sample from the respective inlet ports into the first microchannel. The driving elements may then be used to force the reagent and the sample into the mixing channel. In one embodiment, the sample and the reagent move along the first microchannel at substantially the same speed such that the fluids meet at the junction 212.

In one embodiment, the driving elements force the mixture of the sample and the analyte along the detection channel 216 and subsequently along the microchannel 224 before exiting the chip via the outlet 226 or the outlet 228.

Figure 5:
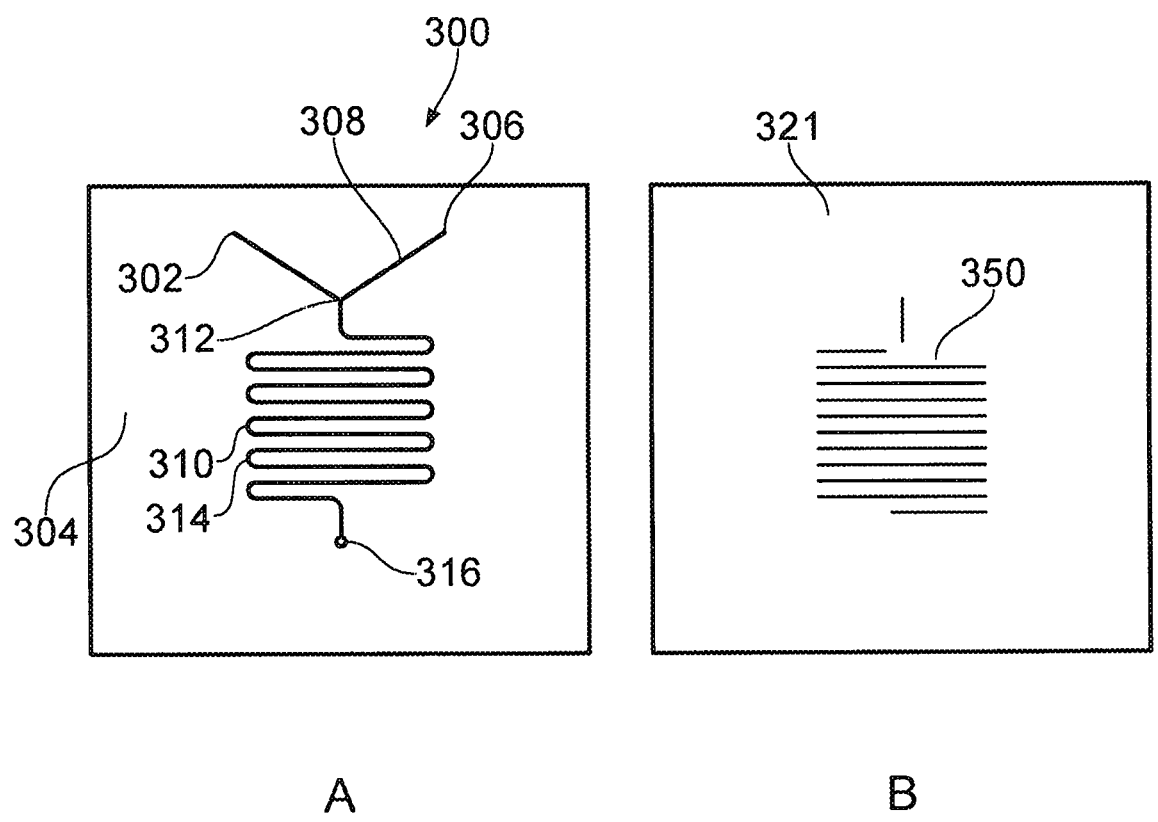
FIG. 5a is a top view of a microfluidic chip in accordance with certain embodiments of the present invention which comprises a plate with the serpentine mixing channel.
FIG. 5b illustrates a plate of a microfluidic chip of certain embodiments, which comprises herringbone structures as a passive mixing element. The plate of FIG. 5a and the plate illustrated in FIG. 5b are aligned such that the herringbones line up with the serpentine channel.

FIGS. 5a and 5b illustrate an alternative embodiment of the microfluidic chip 300. The microfluidic chip 300 comprises an inlet port 302 for a sample to be supplied to the chip. The inlet port 302 is provided on an upper surface 304 of the chip. The upper surface may be provided by an upper planar structure in a layered chip as described above.

The microfluidic chip 300 also comprises a second inlet port 306. The second inlet port can be used to introduce one or more reagents to the chip. The second inlet port 306 is in fluid communication with the first inlet port via a first microchannel 308. The microchannel 308 is connected to a further microchannel 310. In the illustrated embodiment the further microchannel 310 is connected to the first microchannel at a junction 312 which is generally at a midpoint of the first microchannel between the first inlet port and the second inlet port.

The further microchannel 310 comprises a serpentine pathway portion 314 in which the reagent and the sample mix prior to detection taking place. Thus, the further microchannel may be referred to as a mixing microchannel. The mixing channel is connected to a detection channel 316 which is provided at approximately right angles to the mixing channel at least partially through the thickness of the chip.

Figure 26:
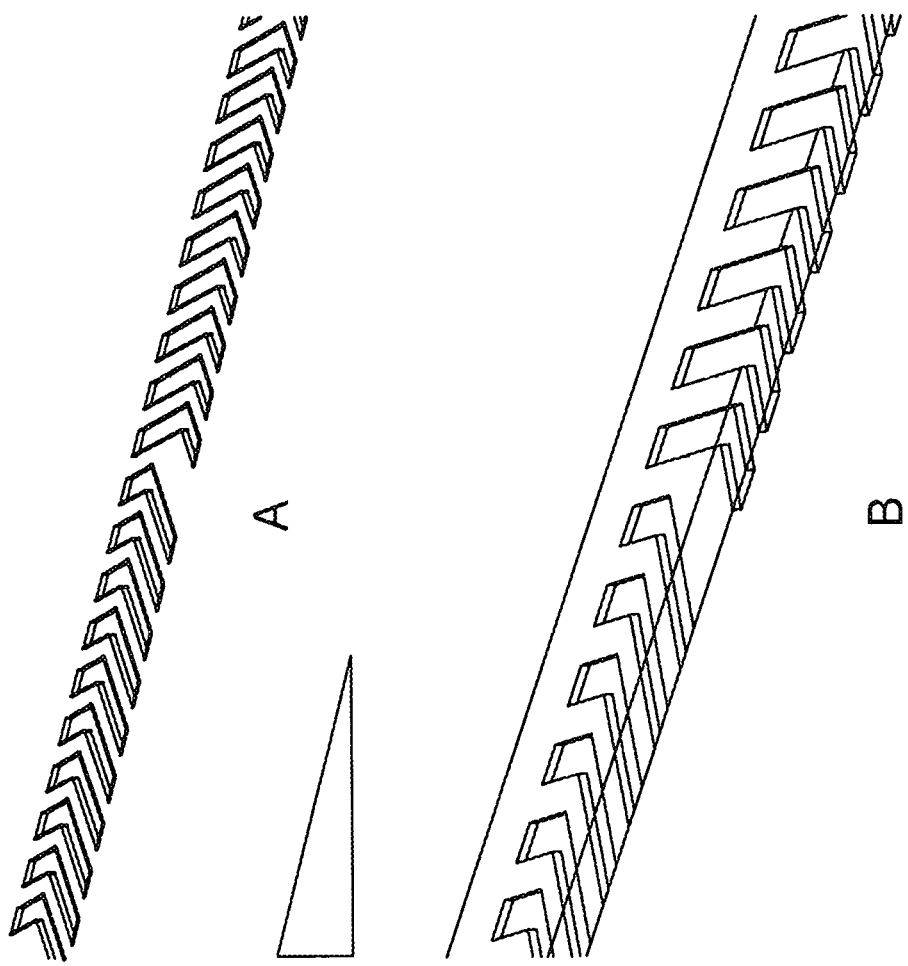
Figure 27:
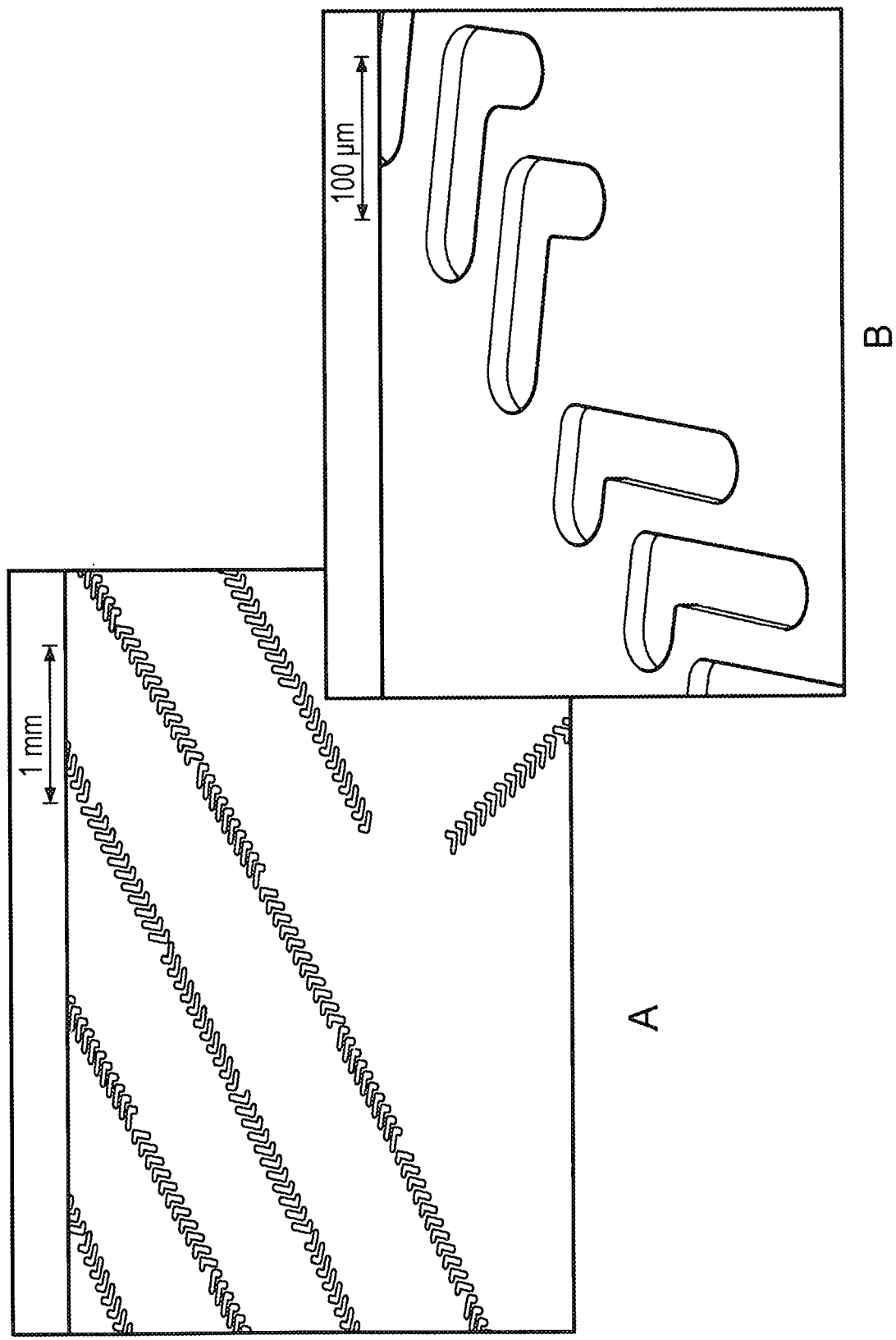

As shown in FIG. 5B, an intermediate planar structure 321 may provide a lower surface of the microchannel 310. The intermediate planar structure 321 may be patterned to provide a passive mixing structure such as a herringbone structure 350 in the microchannel. In alternative embodiment, herringbone structures are formed by etching on a lower surface of the upper planar structure. The lower surface of the upper planar structure may be etched to a depth of about 10 μm. Details of such herringbone structures are shown in FIGS. 26 and 27. In one embodiment, the herringbone structures are as described in Strook et al., (Science, 2002, 295, pp 647-651).

FIG. 6b illustrates an alternative embodiment in which the first microchannel and the mixing microchannel are provided in the upper surface of the intermediate planar structure. The upper planar structure is provided with two inlet ports, each of which is connected to an end of the first microchannel. The lower planar structure is provided with a further microchannel in fluid communication with the detection channel and an outlet.

In use, the detection channel 216, 316 provides a path length between a source, e.g. a light source and a detector. The source may be positioned adjacent to or in contact with a first surface e.g. the upper surface of the chip in a position which is aligned with a long axis of the detection channel i.e. in a direction through the thickness of the chip.

The source may be a light source. The light source may be connected to e.g. a fibre optic cable which is connected or is adjacent to a surface of the microfluidic chip.

The detector or a connecting element, e.g. a fibre optic cable, may be connected to or positioned adjacent to an opposing surface of the microfluidic chip to the light source. The detector or connecting element is aligned with the long axis of the detection channel and is therefore aligned with the light source. In some embodiments, the detector is provided at the same side of the chip as the source.

In use, an analyte e.g. a sample or a mixture comprising the sample or portion thereof provided in the path length may absorb some of the light provided by the source, thus meaning that the signal that reaches the detector e.g. a spectrometer will differ.

Each end of the detection channel is enclosed within the chip and therefore the upper surface and the lower surface of the chip which is provided immediately above and below the ends of the detection channel are composed of a material which permits transmission from the source to the detector. In one embodiment, the material is capable of transmitting UV-visible light from a light source to the detector e.g. a UV-visible spectrometer or a visible-near infrared spectrometer. Thus, in one embodiment, the chip is formed at least in part from an optically transparent material.

A chip which comprises a detection channel as described herein can be used to determine one or more characteristics of a compound. As described above, the detection channel provides a pathlength between a source and a detector and therefore characteristics which can be detected and/or measured by way of measuring e.g. absorbance. In certain embodiments, determining the characteristic of the compound involves analysing values of the characteristic at a particular wavelength.

A characteristic of the sample which can be determined using the microfluidic chip according to certain embodiments of the present invention is pH. pH can be detected using for example UV-visible spectroscopy. In one embodiment, the detector detects visible light.

Figure 7:
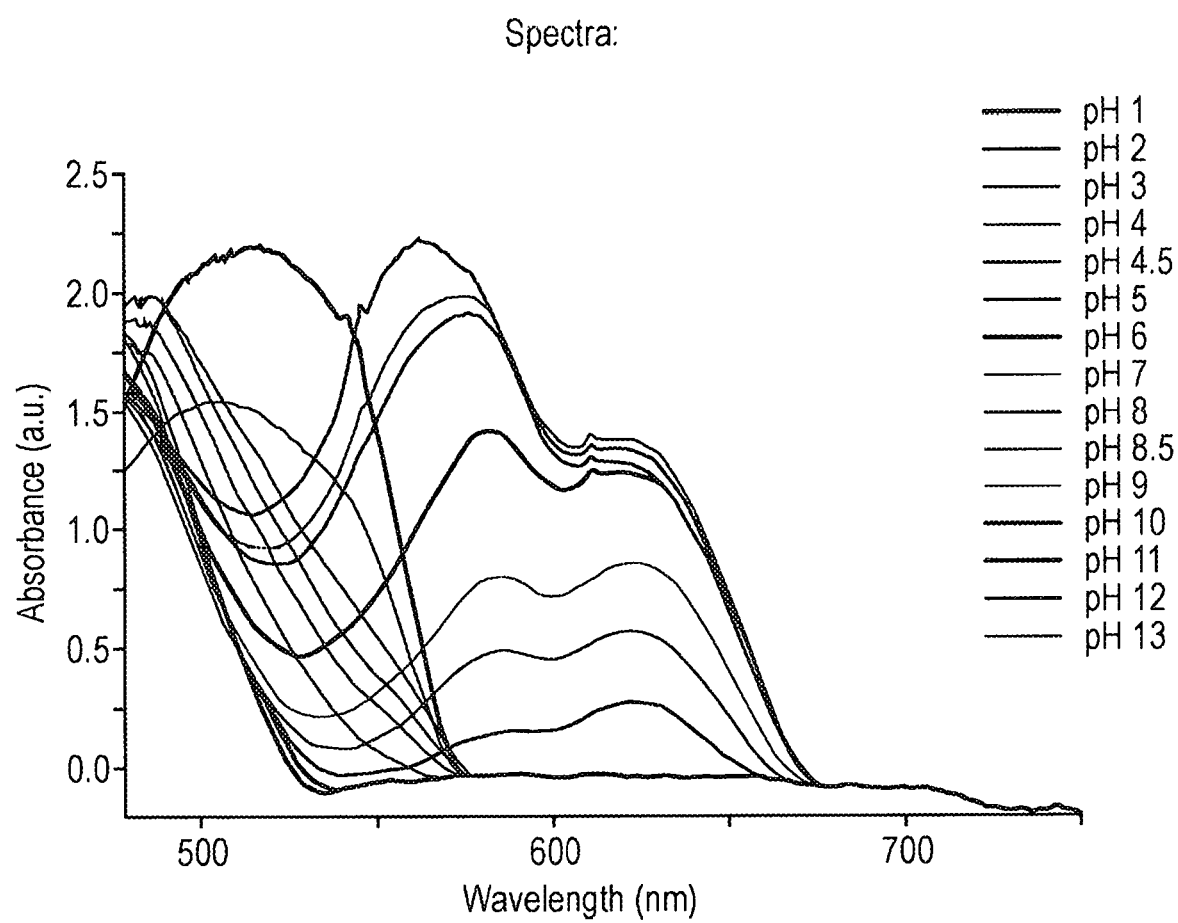
FIG. 7 is a graph illustrating the absorbance of pH standard solutions of different pH at different wavelengths following mixing of the standard solutions with a universal pH indicator.

FIG. 7 is a spectra illustrating the absorbance of solutions of different pH at different wavelengths. In some embodiments, the method of determining pH may further comprises preparing a V-shaped plot as shown in FIG. 8 and as described above.

Alternatively, in one embodiment, the method comprises preparing one or more radar plots of the absorbance values prepared at different wavelengths for each pH standard. Comparative analysis of the standard and the absorbance values of the sample can then be carried out to determine the pH of the sample. Exemplary radar plots are shown in FIG. 9 to 11.

FIG. 12 illustrates a microfluidic chip 1000 according to an embodiment of the present invention. The microfluidic chip 1000 is configured to be used to determine a plurality of sample characteristics. The microfluidic chip 1000 has a number of reaction e.g. detection zones at which one or more characteristics can be analysed.

The microfluidic chip may comprise a layered structure as described above. That is to say, the chip may include three layers formed from an upper planar structure 1020, a lower planar structure (not shown) and an intermediate planar structure (not shown) which is positioned between the upper and the lower planar structures. The layers may be adhered to each other in a fluid sealing way as described above.

An inlet port 1040 is provided in the upper planar structure for introducing a sample to the chip.

The inlet port 1040 is in fluid communication with a first microchannel 1050 which extends substantially across the length of the chip. The first microchannel may be connected to the inlet port by a sample inlet channel 1045. In addition, the first microchannel 1050 is in fluid communication with an outlet 1070. The first microchannel may be in fluid communication with the outlet via an outlet channel 1075. In embodiments in which the microfluidic chip is formed from three layers, the microchannels may be provided at an interface between the middle and lower layers.

The chip is also provided with one or more valve elements.

In certain embodiments, the valve element is a valve assembly as shown in FIG. 31 and FIG. 32 and described below.

The valve elements are provided in the first microchannel to direct and control flow of a fluid e.g. the sample and/or one or more reagents and/or other fluids located in the first microchannel.

Thus, the microfluidic chip comprises a first valve element 1060 which is provided at a sample introduction region of the first microchannel adjacent the inlet port region. The first valve element may be an "open/close" type valve which can control flow of the sample from the inlet port into the first microchannel. That is to say, the first valve element in its open position may allow the sample, when introduced into the chip via the inlet port, to flow into the first microchannel. The valve may then be placed in a closed position to prevent flow of the sample from the sample inlet channel into the first microchannel.

Figure 28:
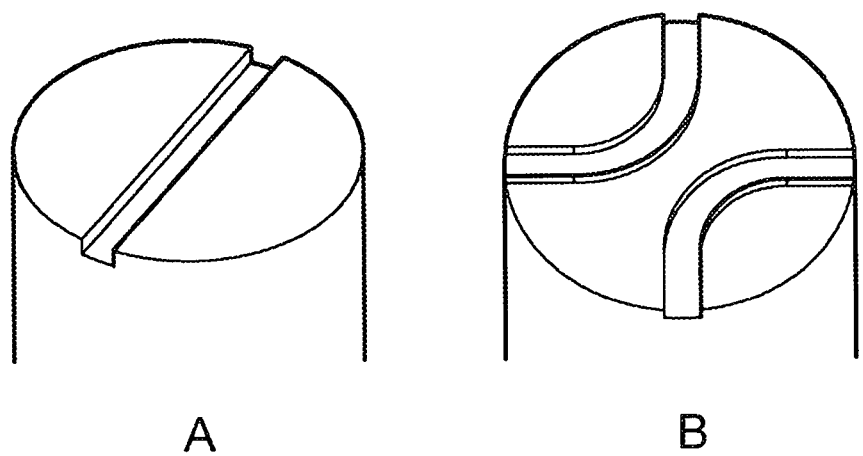

Aptly, the chip also includes a plurality of further valve elements. In addition, the chip comprises a number of further microchannels which intersect the first microchannel. The intersecting channels aptly intersect the first microchannel at a position between a pair of valve elements. Exemplary valve elements are shown in FIG. 28 and FIG. 31. The valve elements may comprise one or more channels for fluid flow. In order to avoid contamination of the first microchannel from reagents loaded in the detection zones when the first microchannel is being filled with the sample, each intersecting channel may also be provided with a pair of valve elements which can be in the "off" or closed position when the first microchannel is being filled with the sample, thus preventing ingress of fluid from the detection zone. These valve elements are indicated by 1420a, 1420b, 1420c and 1420d and 1422a, 1422b, 1422c and 1422d.

Each pair of valve elements can be used to isolate a portion of a fluid within the first microchannel between the pair of valve elements, and subsequently direct the portion of fluid towards one or more reaction zones as described in more detail below.

Aptly, the chip includes a first intersecting microchannel 1110. The first intersecting channel is provided with a second inlet port 1120 at an upstream region thereof. The first microchannel and the first intersecting channel meet at a junction which may be at a point which is equidistant between a pair of valve elements 1090, 1230. Alternatively, the junction point may be at an offset point between a pair of valve elements. The valve elements may be "on/off" i.e. "open/close" valves which, when both in the "closed" position, can isolate a portion of fluid e.g. a portion of the sample therebetween.

The first intersecting channel 1110 is in fluid communication with a first reaction zone 1140. The first reaction zone 1140 includes a first separation element 1150. The first separation element 1150 may be a monolithic chromatographic body.

The first intersecting channel is connected to an upstream portion of the first separation element 1150 such that fluid, e.g. the sample, in the first intersecting channel can flow through the first separation element. In the exemplified embodiment, the first separation element is a strong anionic exchange (SAX) monolithic body. In one embodiment, the first reaction zone is comprised in a modular component 1155 which is secured to the upper surface of the upper planar structure such that the first intersecting channel is in fluid communication with the first separation element. Thus, the modular component comprises an inlet 1165 and a flow channel which are in fluid communication with the first intersection channel and the first separation element. The modular component also comprises an outlet 1175 downstream from the first separation element which is in fluid communication with the channel 1180 in use to allow the sample to flow from the first separation element to the channel 1180.

The first separation element may comprise a monolithic body. The monolithic body may be formed as described below;

A mould is designed using SolidWorks software which was also used to program the CNC machine. The CNC machine was then used to mill the mould out of PTFE.

0.282 g polyethylene oxide (PEO) was added to a 50 ml centrifuge tube and cooled with ice. 2.58 ml nitric acid (1 N) 0.29 ml water was then added and the mixture stirred for 60 to 90 minutes. The mixture was then left for 1 hour maintaining cooling. After 1 hour, 2.26 ml tetraethyl orthosilicate (TEOS) was added and stirring and cooling continued.

The PTFE mould in two halves was put together in a holder and heated at 40° C. for 1 hour, after which the holder was tightened to ensure no leakage. After 1 hour of stirring, the PEO/TEOS mixture was injected into the mould ensuring the mould was filled and all air escaped. A clamp with a parafilm layer was placed against the mould inlets and tightened to seal the mould and the whole apparatus heated to 40° C. for 72 hours. After this time, the clamp was removed and the two halves of the mould carefully separated.

The monolithic body formed in the mould was removed from the mould, rinsed with water and then soaked in water for 24 hours with regular replacement of the water to ensure the monolithic body was well washed.

The monolithic body was added to a mixture of 40 ml water and 10 ml ammonium hydroxide (5 M) and the mixture heated for 16 hours at 90° C. under reflux. After this time, the monolithic body was removed from the mixture and placed in water. The water was replaced regularly for the next 8 hours, after which the monolithic body was dried at 40° C. Finally the monolithic body was heated to 550° C. in a furnace for 3 hours. When cool the monolithic body was ready for use. For further details on the preparation of silica monoliths please see P. D. I. Fletcher, S. J. Haswell, P. He, S. M. Kelly, A. Mansfield, J Porous Mater. 2011, 18, 501.

Aptly, the monolithic body is functionalized as follows:

To prepare a cation-exchange monolithic, the desired amount of 3-mercaptopropyltrimethoxysilane is added to a solution containing 10 ml ethanol and 10 ml water, followed by the addition of a silica monolith. The mixture is refluxed overnight. The monolith supported thiols is recovered and washed with water to remove unreacted reagents. The obtained silica monolith is oxidized by reaction with 10 ml hydrogen peroxide (30%) in 10 ml water and 10 ml methanol overnight at 60° C. The monolith is recovered and washed with water, and treated with 10 ml of 1 M $H_2SO_4$. The sulfonic acid modified monolith is washed with water and dried at 60° C. overnight. This cation-exchange monolith shows a CEC (cation exchange capacity) of 181 µeq/g.

To prepare an anion-exchange monolithic body, the desired amount of silica monolith is added to anhydrous toluene. To this is added a solution containing 0.12 ml methyltrichlorosilane and 0.3 ml 3-chloropropyltrichlorosilane in anhydrous toluene. The reaction is conducted at 80° C. under nitrogen atmosphere for 24 hours. After this, the monolith is recovered and washed with dichloromethane, methanol, water and methanol to remove unreacted reagents and then dried at 80° C. overnight. Following this, the monolith is treated with N,N-dimethylethanamine in DMF at 80° C. for 24 hours to form positively charged groups on the surface of the silica monolith.

To prepare a reverse phase silica monolith, the desired amount of silica monolith is added to a solution of 1.57 mmol octadecyltrimethoxysilane in toluene. The reaction is conducted at 80° C. overnight. The monolith is recovered and washed with toluene and dried at 60° C. overnight. For further details on the functionalization of silica monoliths please see C. S. Gill, B. A. Price, C. W. Jones, J Catal. 2007, 251, 145 or C. R. Silva, C. Airoldi, K. E. Collins, C. H. Collins, LCGL North America 2004, 22, 632.

Once functionalised, the monolithic body must be hermetically sealed to ensure that, when administered, fluid flows through the monolithic body and not around the monolithic body, for example at the interface between the monolithic body and housing. This can be achieved by forming a monolithic module according to an aspect of the invention. In particular, the monolithic body may be placed in the first of two moulds with half of the monolithic body held in a recess. The monolithic body is secured in place by a protrusion at each end of the monolithic body which extends to the centre of the primary axis of the monolithic body and remains in contact during a first moulding step. Molten polymer is injected into the first mould and allowed to set forming a first module part over the monolithic body. This resulting first module part with integrated monolithic body is placed in a second mould with the module surface opposite the monolithic body and module sides held within a recess. Molten polymer is injected into this second mould over the exposed monolithic body surface and bonds to the surface of the first module part. After setting, the complete monolithic module is annealed in a furnace. Inlet and outlet holes can be moulded into the monolithic unit during the moulding process or may be machined into the monolithic module. A monolithic module prepared by this process comprises a monolithic body which is hermetically sealed except for the inlet and outlet.

FIG. 14 shows a monolithic module comprising a first and second separation elements. The first separation element 1150 is connected at a downstream end region thereof to a further microchannel 1180. The further microchannel fluidly connects the first separation element to a first detection zone 1190. The first detection zone 1190 contains an electrochemical cell 1200. The electrochemical cell 1200 may be comprised in a separable modular component which is positioned adjacent to the upper surface of the upper planar structure in use such that the channel 1180 is in fluid communication with the electrochemical cell and a sample flows from the microchannel 1180 into the electrochemical cell 1200.

An embodiment of the monolithic module is shown in FIG. 15. Aptly, the separation module may be injection moulded as described herein.

The electrochemical cell 1200 comprises a working electrode, a counter electrode and a reference electrode. Further details of the electrodes are provided below.

The chip comprises a second intersecting channel 1160 which has an inlet port, referred to as a third inlet port 1080, provided at an upstream region thereof. The second intersecting channel 1160 intersects the first microchannel between a pair of valve elements 1230, 1240. The valve elements 1230, 1240 may be "open/close" valves which would be used to isolate a portion of fluid in the first microchannel between the two valves when both valves are in the closed position.

The second intersecting channel is in fluid communication with a second separation element 1170 provided in the first reaction zone 1140. The second separation element 1170 is connected at a downstream end region thereof to a further microchannel 1210 which is in turn fluidly connected to an outlet 1225. The module may comprise an inlet port 1185 which is in fluid communication with the second separation element. The module may also comprise an outlet port 1195 which is in fluid communication with a microchannel 1210.

The chip may also comprise a third intersecting channel 1250 which comprises an inlet port, referred to as a fourth inlet port 1100 at an upstream end region thereof. The third intersecting channel intersects the first microchannel between a pair of valve elements 1240, 1260. The pair of valve elements 1240, 1260 may act to isolate a portion of fluid in the first microchannel in a similar manner to that described above.

The third intersecting channel 1250 meets the first microchannel at a junction 1280 which may be equidistance between the valves 1240, 1260 or may be off-set. The third intersecting channel 1250 comprises a serpentine mixing portion 1270 which is provided downstream from the junction 1280. The third intersecting channel is in fluid communication with a first reagent introduction inlet 1370 at a location upstream from the serpentine mixing portion. A portion of the sample located in the third intersecting channel may be mixed with the reagent in the serpentine mixing portion 1270.

A valve element 1300 which is a bidirectional or multi-directional valve is associated with the third intersecting channel 1250. The third intersecting channel in fluid communication with a second detection zone 1310 which comprises a first detection channel 1320. The detection channel extends at least partially through the thickness of the chip, as described in detail above. The detection channel provides a pathlength between a source and a detector. The second detection zone may also comprise an outlet in fluid communication with the detection channel 1320 for the sample to exit the chip.

Aptly, the chip also includes a fourth intersecting channel 1340 which comprises an inlet port, referred to as a fifth inlet port 1350, at an upstream end portion thereof. The fourth intersecting channel meets the first microchannel at a junction 1360 which may be equidistance between the valves 1260, 1370 or may be off-set. Aptly, the fourth intersecting channel 1340 comprises a serpentine mixing portion 1380 which is located downstream from the junction 1360. The fourth intersecting channel is in fluid communication with a second reagent introduction inlet port 1390 provided at a location upstream from the serpentine mixing portion and downstream from the junction 1360. A portion of the sample in the fourth intersecting channel may be mixed with the reagent in the serpentine mixing portion 1380.

The fourth intersecting channel extends to the third intersecting channel and contacts the third intersecting channel at the valve element 1300. The fourth intersecting channel merges with the third intersecting channel downstream of the valve element 1300 and extends to the second detection zone 1310. Thus, fluid from the fourth intersecting channel may flow into the first detection channel 1320. The valve element 1300 acts to direct flow from either the third intersecting channel or the fourth intersecting channel or both channels into the second detection zone depending on which characteristic of the sample is to be determined. The detection channel may be in fluid communication with an outlet 1325 provided on an upper surface of the chip. Thus, fluid may flow through the detection channel and subsequently exit the chip via the outlet 1325.

The chip may additionally comprise a third detection zone 1400 in the first microchannel.

The chip may further comprise an additional valve element 1410 which controls flow of a fluid e.g. the sample in the first microchannel to the outlet 1070.

FIG. 13 illustrates a system 2000 of certain embodiments of the present invention. The system 2000 comprises the microfluidic chip of FIG. 12. As shown in FIG. 13, the first reaction zone may also include a radiation detection element 1220. The radiation detection element is for example a positron detector and is positioned over and adjacent to the first reaction zone. In embodiments in which the system comprises the radiation detector element, the first reaction zone may be referred to a fourth detection zone.

In addition, the system comprises a fibre optic cable 2010 which is connected to a source e.g. a light source (not shown). The cable 2010 is positioned adjacent to the first detection channel 1320 and at least a portion thereof is aligned with the long axis of the detection channel. A second fibre optic cable 2020 is provided adjacent to the detection channel at the opposing surface of the chip and is connected to a detector (not shown). At least a portion of the second fibre optic cable is also aligned with the long axis of the detection channel such that light for example may be transmitted from the first fibre optic cable along the detection channel to the second fibre optic cable and to the detector.

The system illustrated in FIG. 13 may additionally comprise a further source and detector. For example, as shown in FIG. 13, a cable 2040 suitable for Raman spectroscopy is positioned adjacent to the second detection channel in the third detection zone.

FIG. 19 and FIG. 20 illustrate an embodiment of the system in which a detection fibre and a source fibre are provided on opposing surfaces of the chip and are aligned at a portion adjacent to the chip with the long axis of a detection channel.

As shown in FIGS. 12 to 16, the first detection zone comprises an electrochemical cell 1200. In certain embodiments, the electrochemical cell comprises a chamber approximately 50 µm deep, 150 µm wide and 20 mm long. A working electrode 2030 is comprised in the cell. In one embodiment, the working electrode is a platinum wire (0.25 mm diameter) encased in a glass tube (3 mm diameter). The electrochemical cell also comprises a counter electrode 2050 and a reference electrode 2060. In one embodiment, the counter electrode comprises a platinum wire having a diameter of approximately 1 mm in diameter. In one embodiment, the reference electrode comprises a silver/silver chloride wire having a diameter of approximately 1 mm. Each of the electrodes is placed by way of holes in the cell. In an alternative embodiment, the working electrode is gold, the counter electrode is platinum wire and the reference electrode is palladium wire.

In an alternative embodiment, the electrochemical cell comprises a screen-printed electrode. The screen-printed electrode may be adapted from commercially available electrodes such as those available from DropSens, Spain. In one embodiment, a seal is formed between the electrode and the channels by an O-ring.

In certain embodiments, the chip layers may be glued together. Alternatively, the layers may be secured together using one or more magnets or screwed or clamped together.

Aptly, the first and the second separation elements are provided in a component which is separable from the chip and which can be positioned adjacent to the upper planar surface in use. The component is shown in FIG. 16. The component comprises a first inlet 2070 which is in fluid communication with the microchannel 1180 when the module is positioned in its correct orientation on the upper surface of the upper planar structure. The module may also include an outlet 2080 in fluid communication with the microchannel 1210 and which permits a fluid which has been flowed through the second separation element to exit the chip. Radiation detection may take place on the second separation element.

The module may also comprise a flow channel 2090 which flows from the inlet to an outlet 2100 and past the electrodes.

An alternative embodiment of the chip and system is shown in FIGS. 17 and 18. The microfluidic chip 3000 of FIG. 17 comprises many of the features of the microfluidic chip 2000. The microfluidic chip 3000 includes a first microchannel 3010 which is in fluid communication with an inlet port 3020. A sample fluid can be introduced into the microfluidic chip through the inlet port 3020.

The first microchannel 3010 comprises a first valve element 3040 which can control movement of a fluid e.g. the sample into the first microchannel.

The chip illustrated in FIG. 17 comprises an additional microchannel 3050, referred to as a sample channel. The sample channel is in fluid communication with the sample inlet port. The sample channel intersects the first microchannel. The first valve element may be a multidirectional valve which controls movement of the sample either to the sample channel or the first microchannel depending on the requirement of the user. A schematic representation of the first valve element is shown in FIG. 28a.

An alternative valve element arrangement is shown in FIG. 28b in which the sample is pumped through the first valve element into the sample channel. Subsequently, the valve element is turned and negative pressure can be applied to draw the sample in the sample channel into the first microchannel for subsequent direction to the detection zones.

With reference to FIGS. 17a and 17b, the sample channel is in fluid communication with an outlet 3060. Aptly, the sample channel is not connected to any further inlets. As such, no reagents are added to the sample in the sample channel and the sample may be suitable for administration to a patient in need thereof. Whether the sample is administered will be dependent on the outcome of the one or more tests carried out by the system of certain embodiments and determination of the sample characteristics.

The sample channel may be in fluid communication with one or more detection channels as described herein. A first detection channel 3070 is provided which can be used to determine a characteristic such as for example clarity and/or appearance of the sample. A second detection channel 3080 may be provided downstream from the first detection channel.

As shown in FIG. 29, the first detection channel and the second detection channel may be in fluid communication via a portion of the sample channel which is provided in the lower planar structure. Thus, in use, a sample or portion thereof is flowed along the sample channel, down the first detection channel, along the sample channel in the lower planar structure and then upwardly along the second detection channel. The sample then exits via the outlet 3060.

Aptly, the first microchannel comprises a plurality of valve elements which can be used to direct flow of the sample and/or reagents and/or solutions from the first microchannel to other areas of the microfluidic chip. In addition the valve elements can be used to isolate portions of a fluid in the first microchannel from other areas of the first microchannel. Aptly, the valve elements are provided in series. FIG. 28 and FIG. 31 illustrate exemplary valve elements.

Thus, as shown in FIGS. 17a and 17b, the first microchannel 3010 may comprise a second valve element 3100, a third valve element 3110, a fourth valve element 3120, a fifth valve element 3130, a sixth valve element 3140 and a seventh valve element 3145. Ultimately, the number of valve elements may depend on how many tests are to be provided on the chip and thus how many detection zones portions of the sample are to be directed to.

The first microchannel may comprise an approximately 90 degree change in direction (3030) between the first valve element and the second valve element.

A first intersecting channel 3150 may be provided on the chip. The first intersecting channel 3150 is in fluid communication with a further inlet, referred to herein as the second inlet port 3160. The first intersecting channel intersects the first microchannel at a junction between the second valve element 3100 and the third valve element 3110.

As described herein, each intersecting channel may be provided with a pair of valve elements which prevent flow of fluid from the detection zones during filling of the first microchannel with the sample. Aptly, one of the pair of valve elements is provided in the intersecting channel upstream of the junction between the intersecting channel and one of the pair is provided downstream from the junction. The valve elements, indicated by 3500a, 3500b, 3500c, 3500d and 3500e and 3510a, 3510b, 3510c, 3510d and 3510e are placed in a closed position when the first microchannel is filled with the sample. Once flow of the sample or portion thereof to a detection zone is desired, the valves of the intersecting channel can be opened to provide a fluid flow path to the detection zone.

It will be appreciated that in certain embodiments, the first microchannel may be provided with an alternative valve element arrangement. For example, in one embodiment, the first microchannel can be provided with a series of single valve elements, each of which is provided at the intersect with an intersecting channel, in place of a pair of valve elements positioned adjacent to a junction between the first microchannel and an intersecting channel. Each single valve element may comprise a through channel which is sized to accommodate a volume of the sample. This volume of sample can be isolated by turning the valve element. The isolated sample portion can then be flowed from the valve channel by way of positive pressure supplied by a driving mobile phase. This embodiment is shown in FIG. 30. The chip 5000 shown in FIG. 30 comprises a single valve element positioned at a junction between the first microchannel and an intersecting channel in place of the four valve element system shown in FIG. 17 for example. Thus, the chip of FIG. 30 comprises five valve elements 5010, 5020, 5030, 5040 and 5050. The valve element provided in the embodiment of FIG. 30 may be as illustrated in FIG. 28A.

Downstream from the junction, the first intersecting channel is in fluid communication with a reagent inlet port 3260. Further downstream from the reagent inlet port 3260, the first intersecting channel comprises a serpentine mixing portion 3270. The first intersecting channel is in fluid communication with a detection zone 3280. The detection zone aptly comprises a third detection channel 3285 which extends at least partially through the thickness of the chip and provides a pathlength between a source and a detector.

A second intersecting channel 3170 is provided on the chip. The second intersecting channel is in fluid communication with an inlet port 3180, referred to as a third inlet port. The second intersecting channel intersects the first microchannel 3010 at a junction between the third valve element 3110 and the fourth valve element 3120. In the illustrated embodiment, the second intersecting channel has a similar structure to the first intersecting channel. The second intersecting channel is in fluid communication with a second reagent inlet port 3290 at a position downstream from the junction. The second intersecting channel comprises a serpentine mixing zone 3295 in which a portion of the sample and a reagent introduced via the second reagent inlet port can be mixed together prior to entering the detection zone.

The chip may also comprise a third intersecting channel 3190. The third intersecting channel is in fluid communication with an inlet port 3200, referred to as a fourth inlet port. The third intersecting channel intersects the first microchannel at a junction between the fourth valve element 3120 and the fifth valve element 3130. The third intersecting channel is in fluid communication with a third reagent inlet port 3300 at a position downstream from the junction. The second intersecting channel comprises a serpentine mixing zone 3305 in which a portion of the sample and a reagent introduced via the second reagent inlet port can be mixed together prior to entering the detection zone.

One or more valve elements 3310, 3320, 3330 may be provided to control flow of a fluid in the first, second and/or third intersecting channels to the detection zone. Thus, the valve elements can be used to selectively move fluid e.g. a mixture of a portion of the sample and a reagent from one but not the other intersecting channels. Thus, only one mixture of sample and reagent is directed to the detection zone and into the detection channel at a time.

The microfluidic chip may additionally comprise one or more inlet ports for introducing a solution e.g. a washing solution or a standard solution through the detection zone. These inlet ports 3350, 3360 and 3370 are aptly provided upstream to the valve elements thus enabling flow of a fluid introduced through these inlet ports to the detection zone be controlled.

The detection zone may comprise an outlet 3340 for removing fluid which has travelled along the detection channel.

In alternative embodiments, each of the first, second and third intersecting channels may be in fluid communication with a detection channel. That is to say in place of the third detection channel depicted in FIG. 17, a plurality of detection channels, each connected to a single intersecting channel, may be provided. In such embodiments, determination of a plurality of characteristics using the detection channels may take place simultaneously.

The chip may also comprise a fourth intersecting channel 3210 which intersects the first microchannel at a junction between the fifth 3130 and sixth valve elements 3140. The fourth intersecting channel 3210 is aptly in fluid communication with an inlet port 3220, referred to as a fifth inlet port, provided upstream from the junction. The fourth intersecting channel is in fluid communication with a further detection zone 3520 which comprises a second separation element 3270. The second separation element is as described above. The second separation element may be comprised in a separate module which is provided on the upper surface of the upper planar surface in use. The first separation element is in fluid communication with a microchannel 3420 which flows to a detection zone which also comprises an electrochemical cell 3410. The electrochemical cell is as described herein. The second separation element is in fluid communication with an outlet 3450.

The chip also comprises a fifth intersecting channel 3230 which intersects the first microchannel at a junction between the sixth valve element 3140 and the seventh valve element 3145. An inlet port 3240 referred to as a sixth inlet port, is provided in fluid communication with the fifth intersecting channel upstream from the junction.

The fifth intersecting channel 3230 is in flow communication with a first separation element 3400 provided in the further detection zone 3520. The first separation element is as described above.

The first separation element 3400 is in fluid communication with a further microchannel 3420 which flows into an electrochemical cell 3410. The electrochemical comprises a working electrode, a reference electrode and a counter electrode as described above. The chip may further comprise an outlet 3460 downstream from the electrodes of the electrochemical cell.

FIG. 18 illustrates a system 4000 which incorporates the microfluidic chip illustrated in FIG. 17. The chip may also be provided with a radiation detector 4010. The radiation detector may be for example a positron detector or a gamma detector.

FIG. 18 also illustrates a fibre optic cable 4020 which is positioned generally aligned with the first detection channel 3070. The fibre optic cable may be connected to a source e.g. a light source (not shown). The system further comprises a cable 4030 which is generally aligned with the first detection channel on an opposite surface to the cable 4020. The cable 4030 is connected to a detector e.g. a miniaturised UV-visible spectrometer or a vis-NIR spectrometer.

Similarly, a pair of cables 4040, 4050 are positioned adjacent to the third detection channel and are connected to a source and a detector respectively. A further cable 4060 is positioned adjacent to and generally aligned with the second detection channel. The further cable 4060 may be a Raman spectrometry cable. The Raman spectrometry cable may act as a connector to a Raman probe which acts as both the source and the detector.

FIGS. 19 and 20 represent a system according to certain embodiments of the present invention.

As described herein, the chip may comprise one or more valve elements. FIG. 31 illustrates an embodiment of a valve element for use in directing fluid flow within chips described herein. Thus, FIG. 31 shows a valve assembly 400 according to certain embodiments of the present invention for a microfluidic chip includes a valve shaft 402 having a splined upper end region 404 and a valve head 406 attached to a lower end region 408. The valve head 406 has a substantially flat upper surface 410 and a substantially flat lower surface 412. The lower end region 408 of the valve shaft 402 is located in a central bore that extends downwardly into the valve head 406 from the upper surface 410 of the valve head 406. The upper surface 410 of the valve head abuts with a lower surface of an annular shoulder 414 of the valve shaft 402. The valve head 406 may be attached to the valve shaft 402 by adhesive, a mechanical fastener, friction fit, or corresponding screw threads, or the like.

A through conduit 416 in the form of a channel is disposed in the lower surface 412 of the valve head 406. Alternatively, the through conduit 416 may not be disposed in the lower surface 412 of the valve head 406 and may be a through hole disposed between the upper and lower surfaces 410,412 of the valve head 406.

The valve assembly 400 includes a cap-like valve housing 418 having an annular wall portion 420 and an upper portion 422. The upper portion 422 has a centrally located aperture 424 for slidably receiving the valve shaft 402 such that the valve housing 418 can be slid on to the upper end region 404 and along a portion of the valve shaft 402. The central aperture 424 is substantially circular and the valve shaft 402 is substantially cylindrical such that it is rotatable about a valve axis 426 when located in a microfluidic chip whilst also being translatable in a direction along the valve axis 426 with respect to the valve housing 418.

The annular wall portion 420 of the valve housing 418 includes a screw thread 428 that corresponds to a screw thread in an upper layer of the microfluidic chip (as described hereinbelow). The annular wall portion 420 further includes a plurality of flat surfaces for engagement with a tool for driving the valve housing 418 and securing the same in the upper layer of the microfluidic chip. One end of a compression spring 430 sits on an upper surface of the annular shoulder 414 of the valve shaft 402 and the other end of the compression spring 430 abuts an inner surface of the upper portion 422 of the valve housing 418. The compression spring 430 biases the valve head 406 away from the valve housing 418. Aptly, the spring may sit directly on the shoulder which is formed from silicone or it could sit indirectly using washers between. Alternatively, the main shaft may comprise a shoulder To install the valve assembly 400 (e.g. a plug type valve assembly) in a microfluidic chip 500 according to certain embodiments of the present invention, as illustrated for example in FIG. 32, the valve head 406 is located through a correspondingly shaped and sized aperture 520 in an upper layer 502 of the microfluidic chip 500 to engage with a recessed valve seat surface 522 disposed in an intermediate layer 504 of the microfluidic chip 500. The compression spring 430 is placed over the upper end region 404 of the valve shaft 402 to sit on the annular shoulder 414 thereof. The valve housing 418 is then placed over the upper end region 404 of the valve shaft 402 and the screw thread 428 thereof is brought into engagement with a corresponding screw thread (not shown) surrounding the aperture 520 in the upper layer 502 of the microfluidic chip 500. A suitable tool, such as a hex spanner, is used to drive and securely attach the valve housing 418 to the upper layer 502 of the microfluidic chip 500. In turn, the compression spring 430 is compressed between the annular shoulder 414 and the valve housing 418 such that the spring 430 biases the valve head 406 against the valve seat surface 522. In certain embodiments, the valve could be fully assembled separately and later be inserted to the microfluidic device assembled layers.

In use, a suitable actuator, such as a stepper motor (not shown), is coupled to the upper splined end region 404 of the valve shaft 402 to selectively rotate the valve head 406, and in particular the through conduit 416, between an open position and a closed position relative to one or more fluid flow channels 524 disposed in the intermediate layer 504 of the microfluidic chip 500. This provides for selective delivery of at least a portion of a fluid sample from an input region of the microfluidic chip 500 towards a detection zone of the microfluidic chip 500.

The splined upper end region 404 of the valve shaft 402 further allows the valve shaft 402 to translate in a direction along the valve axis 426 with respect to the actuator that selectively rotates the valve shaft 402. The compression spring 430 is selected such that a spring force thereof corresponds to a maximum threshold pressure of fluid in at least an upstream portion of the fluid flow channels 524 relative to the valve assembly 400. When the fluid pressure exceeds the maximum threshold pressure, and thus a fluid force acting on the valve head 406 exceeds the spring force of the compression spring 430, the valve head 406 and valve shaft 402 are forced upwardly to place the valve in an open configuration and to allow upstream fluid to flow past the valve and towards an outlet channel for the excessive pressure to be safely relieved and damage to the microfluidic chip 500 to be minimised if not prevented. Aptly, the valve assembly 400 may include an adjuster (not shown) to allow a length of the compression spring 430 to be adjusted and thus in turn allow the spring force to be set as desired in accordance with a predetermined maximum threshold fluid pressure.

The valve head 406 is made of a substantially resilient material such as a biomedical grade elastomer. Aptly, the biomedical grade elastomer may be a silicone rubber e.g. medical grade silicone. Such a material improves the sealing engagement between the valve head 406 and the valve seat surface 522 and is suitable for use with fluids for medical applications. Furthermore, it is easily moulded, making it suitable for fabricating a variety of shapes and being medical-grade, there should be very little in the way of contamination of a dose caused by impurities leaching out of the material. The valve shaft 402 and valve housing 418 are made of a metal material, such as brass or aluminium or the like, or alternatively may be made from a relatively hard polymer material, such as nylon or PTFE or the like.

In certain embodiments, the channel in the lower surface of the valve head enables an amount of a sample to be collected. Rotation of the valve may then cause the valve to be disconnected from the microchannel e.g. a sample input channel and connected to a further channel e.g. a channel which is connected to an inlet for a mobile phase. Consequently, a plug of the sample will be injected out from the head of valve having mobile phase liquid behind it. In other words, the dimensions of the channel in the valve can determine the volume of sample contained in the valve, which could be filled with sample and then be isolate by turning the valve, allowing the known volume to be directed into a new channel.

FIGS. 33 to 35 illustrate a further embodiment of the microfluidic chip. The microfluidic chip 5000 comprises a plurality of microchannels. In addition, the chip 5000 comprises a first detection channel 5010 which extends at least partially through the thickness of the chip and which is used for measuring clarity of a sample. A second detection channel 5020 which extends at least partially through the thickness of the chip is also provided. Third and fourth detection channels 5060 and 5070 are also provided in the chip.

The chip 5000 also comprises a first valve assembly 5040 and a second valve assembly 5050 as shown in FIG. 31. A third valve element 5080, which is a plunger-type valve is also provided. The plunger valve may be manipulated by a solenoid head or bolt and nut screw type head. In embodiments in which a solenoid is used, where the amount of voltage create a magnetic field around the central valve shaft push by certain amount of force, the shaft may be moved up and down which causes a blockage in the channel. In certain embodiments, a screw type valve where step motor or physical turn could turn the central shaft up/down which causes shut on or off of the channel.

As shown in FIG. 35, the chip 5000 comprises a first inlet 5090 which is used to introduce the sample into the chip. A second inlet 5100 is provided to allow the introduction of universal pH indicator solution which is used for the determination of pH of the sample as described herein. Third and fourth inlets 5110 and 5120 are used for the introduction of mobile phases for performing chromatographic separations. A fifth inlet 5130 is provided into which iodoplatinate reagent solution may be added. Each of the inlets is connected to a microchannel to provide a fluid flow path.

Aptly, the chip comprises an outlet 5140 for removing waste solution. The chip is provided with an outlet 5150 for the sample e.g. FDG to be removed from the chip. The sample may then be administered to a patient if it is considered of a sufficient quality following analysis of the sample on the chip.

The chip also comprises outlets 5160, 5170 which are provided at the end of fluid flow paths which flow through separation elements which may be positioned on top of the chip.

Further inlets 5180, 5185 and 5200 may be provided to introduce reagents e.g. a chromogenic substrate, a LAL reagent and a stop reagent (e.g. dilute acetic acid) for analysing the presence of endotoxin, as described herein. The inlets may be connected to a serpentine mixing channel which is connected to the detection channel 5020. The detection channel 5020 is in turn connected to an outlet 5190 provided through which a mixture of a portion of the sample, and the reagents used to detect endotoxin may exit the chip.

FIGS. 36 and 37 illustrate a chip 6000 according to certain embodiments of the invention. The chip comprises a separable component 6010 which comprises two monolithic bodies 6020 and 6030 as described herein. The chip also incorporates an electrochemical cell 6040 which in the illustrated embodiment is a screen printed electrode. The electrode may be slid into a recess in the chip.

The chip also comprises a Raman chamber 6060. A pin valve membrane 6050 is provided to control flow of a sample to the Raman chamber. The chip comprises a plurality of inlets and outlets as described herein. Furthermore, the chip is provided with a plurality of detection channels. Fibres, for example, the fibres 6070 and 6080 are positioned adjacent to an end of a respective detection channel for spectroscopic analysis of a solution, e.g. a portion of a sample, which is provided in the detection channel.

The system of certain embodiments of the present invention comprise a chip holder (e.g. as shown in FIG. 21 for holding the chip in place to allow alignment of the light source and the detector with the long axis of the detection channel. In one embodiment, the light source is a fibre optic cable and is in alignment with a fibre optic cable which is connected to a detector. In one embodiment, the holder is configured to support the chip in a vertical orientation in use.

In certain embodiments of the present invention, one or more of the microchannels provided in the chip have a passive mixing structure. In one embodiment, one or more channels comprise a herringbone pattern on one or more surfaces thereof. The herringbone structure of certain embodiments is shown in FIGS. 25 to 27. The herringbone structure of the microchannels can cause chaotic flow e.g. "swirling" of a fluid which is flowing through the channel, thus aiding mixing of constituents in the fluid. FIG. 25 is a schematic representation of a herringbone structure which has been etched or otherwise provided in a lower planar structure. In this instance, the lower planar structure may be an intermediate planar structure as described herein. The etched herringbone pattern provides a surface for a microchannel when the lower and the upper plate are adhered together.

FIG. 26 shows a channel comprising a herringbone structure in more detail. FIG. 26A illustrates a herringbone pattern in a first surface whilst FIG. 26B illustrates a channel which comprises a surface having the herringbone pattern and a transparent plate provided on top of the first surface to form a channel.

Certain embodiments of the present invention are described below with reference to FDG (or [$^{18}$F]FDG) as an exemplary compound for in vivo use. It will be understood by the skilled person that the chip, system and method of embodiments of certain embodiments can be used to determine one or more characteristics of a variety of other compounds. Thus the example below makes reference to specific tests which are used to determine certain characteristics of a sample comprising FDG. In alternative embodiments, the tests may differ depending on the quality control requirements associated with the compound in question. Furthermore, the method of analysing certain characteristics is described with reference to a microfluidic chip according to certain embodiments of the present invention. It will be understood that in certain embodiments, if the layout of components of the chip are different, the method may be adapted accordingly e.g. to alter the sequence of method steps.

In use, a sample comprising a compound is introduced into a microfluidic chip e.g. via the sample inlet port 3020. The sample can be introduced by means known in the art e.g. a syringe pump or the like. The sample is typically in a quantity which is equivalent to or slightly greater than a single unit dose.

In use, a sample of a compound for in vivo use e.g. a radiopharmaceutical is provided to the microfluidic chip. The sample may be provided using a number of methods including for example via a syringe, or a dropper. The sample may be pumped into the microfluidic chip. Fluid, e.g. the sample, can be flowed through microchannels e.g. by applying negative pressure to an outlet connected to the microchannels or by way of a syringe connected to a syringe pump (e.g. Pump 11 Elite, Harvard Apparatus, UK). Other methods of directing flow of a fluid in a microfluidic are known to the person skilled in the art.

The sample input may be carried out automatically or manually. The sample may be provided to the chip in a microfluidic quantity. In one embodiment, the sample is provided in a quantity which is generally equivalent to a unit dose for use in a patient. In one embodiment the sample is supplied in a quantity which is equivalent to a single unit dose once the amount of sample required to perform the quality control analytical techniques have been removed.

The sample or a portion thereof may then be directed to the first microchannel and/or the sample channel. The first valve element 3040 may be provided in a first direction to direct a portion of the sample into the sample channel for example. When the desired quantity of the sample has been directed into the sample channel, the valve direction may be changed to prevent any more of the sample from entering the sample channel.

The portion of the sample in the sample channel 3050 may then flow along the sample channel. Negative pressure applied at an outlet 3060 can be used to flow the portion of the sample along the sample channel and along the first 3070 and the second detection channels 3080. The source e.g. light via a fibre optic cable may be transmitted along the long axis of the detection channel at the same time as the sample or portion thereof is accommodated in the detection channel.

A light source such as a halogen light source (HL-2000-FHSA (Ocean Optics)) is provided in the system according to certain embodiments. A detector such as a visible-near infrared light spectrometer (USB2000+VIS-NIR-ES (Ocean Optics)) is provided as detailed above. Optical fibres (QP400-1-UV-VIS (Ocean Optics)) can be used to connect the light source and the detector to the chip at a position which is generally aligned to the long axis of the first detection channel. In alternative embodiments, the detector may be for example an infra-red detector or a fluorescence detector.

In order to determine appearance and/or clarity, absorbance values of the samples are recorded. The presence of unexpected peaks in the spectra indicates contamination of the sample. FIG. 24 illustrates a peak in the spectra which corresponds to a sample having a yellow-green colour to the eye.

Raman spectroscopy can be performed on a portion of the sample which flows in to the second detection channel 3080 to determine the presence and optionally the quantity of impurities e.g. ethanol and/or acetonitrile in the sample. Aptly, the Raman spectroscopy setup comprises a 785 nm continuous wave laser (Laser-785-IP-LAB, Ocean Optics, UK) coupled into a fibre optic Raman probe (RPB, InPhotonics, Ocean Optics). The probe may have a working distance of 7.5 mm and yield a laser spot size of 160 µm, with a depth of field of 1.5 mm. Scattered light from the sample can be collected via the same probe and directed by the bifurcated optical fibre into a miniaturised spectrometer (QE65000, Ocean Optics).

The Raman probe may be fixed into a custom built holder that allows the laser to be focussed by moving the probe back and forth, before turning a screw to lock it into its final position. Raman spectra and other absorption spectroscopy results may be recorded using SpectraSuite software (Ocean Optics).

Aptly, the microfluidic chip is placed into an aluminium holder, orientated vertically, and was positioned via an x-y translation stage such that the Raman laser was aligned with the 368 μm diameter detection channel in the chip. The probe was then focussed into the 3 mm long channel using the holder described above.

In one embodiment, for the sample (e.g. a sample comprising [$^{18}$F]FDG) to be considered suitable for in vivo use, it must contain no more than 5000 ppm in water of ethanol and no more than 410 ppm in water of acetonitrile. Aptly, the method of certain embodiments comprises calibrating the Raman spectrometer by recording the spectra of the ethanol and acetonitrile standards and comparing the peak intensities to those of the sample. Aptly, peak intensities will be taken at approximately 882 cm$^{-1}$ for ethanol and approximately 925 cm$^{-1}$ for acetonitrile.

No reagents are added to the portion of the sample directed into the sample channel. Therefore, this portion of the sample can be collected from the outlet 3060 and administered to a patient, provided the sample meets all of the quality control requirements. Thus, in certain embodiments, the portion of the sample which is directed into the sample channel is equivalent to a unit dose of the compound.

The remainder of the sample may be directed into the first microchannel. This may occur prior to or subsequent to the portion of the sample flowing into the sample channel. The portion of the sample may be flowed into the first microchannel using application of negative pressure applied to the outlet 3060. During this stage, all of the second to seventh valves are open to allow flow of the portion of the sample along the length of the first microchannel. During the filling of the first microchannel, the valve elements of the intersecting channels are closed to avoid contamination of the sample with reagents from the detection zones.

Once the portion of the sample is situated along the first microchannel, application of negative pressure is ceased. Aptly, each of the second to seventh valves are closed so as to isolate portions of the sample between pairs of valve elements. It is then possible to carry out a different analytical technique on each isolated sample portion so as to determine multiple characteristics of the sample.

Thus, aptly, the portion of the sample isolated between the second and the third valve elements can be analysed to determine pH of the sample. A driving solution is introduced into the inlet port and thus into the first intersecting channel 3150. Introduction of the driving solution forces the portion of the sample isolated between the closed valve elements into the first intersecting channel to form a plug of sample. The driving solution causes entraining of the isolated sample such that substantially all of the sample isolated between the valves enters the first intersecting channel. The sample plug is then forced along the first intersecting channel downstream from the junction of this channel and the first microchannel. It will be appreciated that the valves of the intersecting channel must be open to allow movement of the sample and solution.

A reagent is introduced via reagent inlet port 3260. If pH is being measured, a universal pH indicator is introduced. The universal pH indicator is then mixed with the sample plug in the mixing zone of the first intersecting channel. Aptly, the universal pH indicator solution (pH 3-10) is supplied by e.g. Fluke (code: 31282), diluted with ethanol in a 1:2 ratio of indicator/ethanol. A colourimetric reaction between the sample and the universal indicator takes place which can then be analysed using UV-visible or vis-NIR spectrometry. Aptly, the reaction and detection of pH of the sample is carried out at room temperature or in a temperature controlled environment.

A light source such as a halogen light source (HL-2000-FHSA (Ocean Optics)) can be provided in the system according to certain embodiments. A detector (USB2000+ VIS-NIR-ES (Ocean Optics)) is provided as detailed above. Optical fibres (QP400-1-UV-VIS (Ocean Optics)) can be used to connect the light source and the detector to the chip at the third detection channel 3340.

The system may be calibrated by mixing the universal indicator with a range of pH standards or alternatively pH standards at the allowed pH values only (e.g. 4.5 and 8.5 for FDG). The pH of the sample can be detected by analysing the spectra recorded. Further determination of the pH can be carried out by plotting either a V-shaped plot which is generated from absorbance values at a wavelength taken in the 545-550 nm range to provide a pass/fail criteria or alternatively plotting a radar plot from wavelengths of 520, 540, 560, 600, 620 and 640 nm to allow pH determination based on shape recognition.

Once the portion of the sample has flowed down the third detection channel it may be collected from the outlet and discarded.

The third detection channel can be used as a container to carry out a number of absorbance based tests e.g. determination of pH. Other characteristics which can be determined using the absorbance based set up include for example the presence and/or quantity of bacterial endotoxin in the sample. In certain embodiments, e.g. when the sample is a radiopharmaceutical such as FDG, the characteristic may be the presence and/or quantity of Kryptofix 2.2.2.

Aptly, a driving solution is introduced into the second intersecting channel via the third inlet port when the third and fourth valves are closed. The driving solution forces the portion of the sample isolated between the third and the fourth valves to form a plug and flow along the second intersecting channel. A reagent which undergoes a colourimetric reaction with the sample e.g. an iodoplatinate reagent if the characteristic to be determined is the presence/quantity of Kryptofix 2.2.2 is introduced into the second reagent inlet port 3290. and mixing of the iodoplatinate reagent and the sample plug takes place in the serpentine mixing zone of the second intersecting channel.

In one embodiment, the iodoplatinate reagent comprises 5% w/v chloroplatinic acid, 10% w/v potassium iodide and water in a ratio of 5:45:100.

In order to calibrate the system, a standard Kryptofix 2.2.2 solution can be added to the inlet 3290 and mixed with the iodoplatinate reagent in the mixing zone and subsequently detected in the detection channel. The Kryptofix 2.2.2 standard solution may comprise Kryptofix 2.2.2 dissolved in water to a concentration which is equivalent to a standard regulations e.g. 2.2 mg/V, wherein V is the maximum recommended injectable volume of a radiotracer volume in a patient or alternatively, 50 ppm.

Aptly, the analysis is performed at either 574 nm or 590 nm wavelength. The spectra values of the mixture of the iodoplatinate reagent and the sample can then be compared against those obtained for the standard and the amount of Kryptofix 2.2.2 in the sample determined.

Aptly, the chip and system is used to determine the presence and/or quantity of bacterial endotoxin in a sample. Aptly, a driving solution is introduced into the third intersecting channel at the fourth inlet port. A plug of the sample isolated between the fourth and fifth valve elements is formed and driven into the third intersecting channel. A LAL (limulus amebocyte lysate) reagent is introduced into the reagent port 3300 and mixed with the sample. Subsequently, a chromogenic substrate may be introduced via a further reagent port (not shown). Following further incubation (see below), a "stop" reagent comprising dilute acetic acid may be added via a further inlet port (not shown) to quench the reaction. The mixture can then be analysed using the spectrometric set up described above. The absorbance readings are aptly taken at a wavelength of between 405-410 nm. Aptly, the reaction between the LAL reagent and the sample or standard is carried out at 37° C.+/−1° C. Thus, in certain embodiments, the chip and system comprise one or more heating elements (not shown) to heat at least a portion e.g. the mixing zone of the third intersecting channel.

An exemplary protocol for performing the bacterial endotoxin test is as follows:
1. Mix the LAL reagent and the sample e.g. in the serpentine portion of the third intersecting channel and incubate for 10 min at 37° C.;
2. A chromogenic substrate is added to the channel and incubated for 6 min at 37° C.;
3. A "stop" reagent e.g. dilute acetic acid can then be added to quench the reaction;
4. The mixture is flowed along a detection channel;
5. Measurement at 405-410 nm is taken on a spectrometer.

Prior to sample analysis, the chip and system can be calibrated by introduced a standard into the third intersecting channel and mixed with the LAL reagent. The standard may have a concentration of 175 IU/V (where IU is international units and V is the maximum recommended injectable volume of the compound e.g. a radiopharmaceutical for a patient as per the European Pharmacopoeia).

It will be appreciated that the valves 3295, 3320, 3330 are positioned to allow flow of a fluid from a single intersecting channel to the detection zone only and thus prevents flow of the fluid in the other intersecting channels to the detection zone.

In an embodiment, the chip and the system may be used to determine the chemical purity of the sample. In embodiments in which the sample comprises a radiopharmaceutical e.g. FDG, the chip and system may be used to determine the presence and/or quantity of impurities such as for example FDM and CIDG. These impurities may be detected following separation of components in the sample using a strong anion exchange (SAX) stationary phase column which may be a monolithic body or a packed particle bed.

A mobile phase is provided to the fourth intersecting channel 3210 via inlet port 3220. A plug of a portion of the sample isolated in the first microchannel between the fifth and sixth valve elements is formed and forced into the fourth intersecting channel in a direction towards the separation element.

A radiation detector can then be used to determine the presence and/or quantity of these impurities. The radiation detector may be a gamma detector or a positron detector.

The SAX column can be used to separate the components of the sample. In embodiments in which the compound is FDG, impurities such as FDM, D-mannose, D-glucose and CIDG are separated on the column. The sample is then flowed through the electrochemical cell. Pulsed amperometric detection (PAD) can then be carried out. In alternative embodiments, spectrometric or refractive index detection could be used in place of PAD detection.

PAD uses a triple-step potential waveform to combine amperometric detection followed by alternating anodic and cathodic polarizations to clean and reactivate the working electrode surface. Thus, a three-potential waveform is used. The waveform consists of a pulse containing three different voltages applied to the working electrode. The first voltage is used for measuring, the second voltage is for cleaning the working electrode after the measurement and the third voltage is for regenerating the working electrode. The waveform is continuously repeated to achieve detection of the impurities. A potentiostat such as PalmSens3 available from PalmSens, the Netherlands can be used to control the electrodes and voltages and measure the detection signals.

The fifth intersecting channel 3230 can be provided with a mobile phase introduced via the sixth inlet port 3240. Providing the sixth and seventh valves are in a closed position, the driving solution forces a plug of sample isolated between the valves to form and flow along the fifth intersecting channel towards a second separation element. The mobile phase may be for example a solution composed of acetonitrile:water in a ratio 90:10 or 95:10. In certain embodiments, e.g. if the separation element comprised C18-functionalised silica, the mobile phase may be a solution composed of acetonitrile:water in a ratio of between about 40:60 to about 60:40 e.g. 50:50.

The second separation element e.g. a silica monolithic column or a C18-functionalised monolithic column can be used to separate components of the sample. In the exemplified embodiment in which the compound is FDG, the second separation element can be used to separate components such as fluoride-18, FDG and acetylated-FDG within the sample. A radiation detector can then be used to determine the presence and/or quantity of these components in the sample.

It will be understood that analysis of the sample in the first, second and third detection channels may be carried out simultaneously or sequentially.

In certain embodiments, the microfluidic chip does not comprise a detection channel as described herein. For example, in embodiments in which the chip is for use to carry out non-spectrometric techniques, the chip does not need to comprise the detection channel. Thus, in certain embodiments of the present invention, the microfluidic chip may comprise for example a plurality of valve elements as described herein which can be used to isolate portions of a fluid e.g. a sample or mixture comprising a sample, wherein the isolated portions of fluid are directed to a zone on the microfluidic chip where a non-spectrometric analytical technique is performed. An example of a non-spectrometric analytical technique comprises the use of the electrochemical detection cell as described herein. A further example of a non-spectrometric analytical technique is radiation detection using the radiation detector and separation elements described herein.

The system of certain embodiments of the present invention may further comprise computer hardware and software. The computer hardware and software may be used to determine the one or more characteristics or parameters measured on the microfluidic chip. In addition, the computer system may report results of tests carried out on the microfluidic chip. Such results may be reported as for example a simple "Pass/Fail". Alternatively, the results may be reported as a total numeric score which if it falls under or over a certain value can be considered as a "Fail" and therefore unsuitable for administration to a patient.

In certain embodiments, the system may further comprise one or more elements to calibrate and control the components of the system.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any foregoing embodiments. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of determining at least one characteristic of a sample comprising a compound, the method comprising:
    supplying the sample to a supply component of a microfluidic chip, wherein the sample has a volume of 10 ml or less;
    directing the sample or a portion thereof from the supply component via a microchannel which is in fluid communication with the supply component to a detection zone on the microfluidic chip, wherein the detection zone comprises a monolithic body and a positron detector; and
    performing at least one analytical technique on the sample or the portion thereof at the detection zone;
    wherein the supply component, the microchannel, and the detection zone comprising the monolithic body and the positron detector, are all integrated onto the microfluidic chip and the positron detector is positioned over and adjacent to the monolithic body.

2. The method of claim 1, wherein the monolithic body comprises functionalised silica.

3. The method of claim 1, comprising obtaining a measurement value from the at least one analytical technique and determining the at least one characteristic.

4. The method of claim 3, comprising comparing the measurement value to a predetermined corresponding criterion value to determine if the sample is suitable for administration to a patient.

5. The method of claim 4, wherein if the sample is determined to be suitable for administration to a patient, administering the sample to a patient.

6. The method of claim 1, wherein the compound is a radiopharmaceutical.

7. The method of claim 6, wherein:
    the radiopharmaceutical comprises a radioisotope selected from 18F, 99mTc, 11C, 89Zr, 64Cu and 68Ga.

8. The method of claim 6, wherein the radiopharmaceutical is selected from $^{18}$F-FLT ([$^{18}$F]fluoro thymidine), $^{18}$F-FDDNP (2-(1-{6-[(2-[$^{18}$F]fluoroethyl) (methyl)amino]2-naphthyl}ethylidene)malonitrile), $^{18}$F-FHBG (9-[4-[18F]fluoro-3(hydroxymethyl)butyl]guanine or [$^{18}$F]-penciclovir), $^{18}$F-FESP ([$^{18}$F]fluoroethylspiperone), $^{18}$F-p-MPPF (4-(2-methoxyphenyl)-1-[2-(N-2-pyridinyl)-p[$^{18}$F]fluorobenzamido]ethylpiperazine), $^{18}$F-FDG ([$^{18}$F]-2-deoxy-2-fluoro-Dglucose), $^{18}$F-FMISO ($^{18}$F-fluoromisonidazole) and $^{18}$F-sodium fluoride.

9. The method of claim 1, further comprising directing a portion of the sample from an inlet port to an outlet port for collection via the microchannel or a further microchannel.

10. The method of claim 9, comprising directing at least 70% of the sample to the outlet port for collection, wherein optionally the sample directed to the outlet port for collection is a single unit dose of the compound.

11. The method of claim 1, wherein the at least one characteristic is pH and the at least one analytical technique comprises determining pH of the sample.

12. The method of claim 1, wherein performing the analytical technique comprises determining the presence and/or a concentration of an impurity in the sample.

13. The method of claim 1, wherein the at least one characteristic is a concentration of bacterial endotoxin in the sample and the at least one analytical technique comprises:
    supplying a limulus amebocyte lysate (LAL) reagent solution to an inlet port of the microfluidic chip;
    mixing the LAL reagent with the sample or a portion thereof;
    supplying a chromogenic substrate to the inlet port of the microfluidic chip;
    mixing the chromogenic substrate with the mixture of the LAL reagent and the sample or the portion thereof; and
    performing a spectroscopic technique on the mixture and obtaining a measurement value.

14. The method of claim 1, wherein the at least one characteristic is the clarity and/or appearance of the sample or a portion thereof and the at least one analytical technique comprises performing visible/near-infrared spectroscopy, UV-visible spectroscopy or Raman spectroscopy on the sample or a portion thereof.

15. The method of claim 14, further comprising positioning a light source and a detector at opposing surfaces of the microfluidic chip such that a detection zone is provided between the light source and the detector that provides a path length for light emitted by the light source to be transmitted to the detector.

16. The method of claim 1, wherein the at least one characteristic is determining a concentration of one or more solvents in the sample and the at least one analytical technique comprises directing a flow of the sample or a portion thereof to the detection zone and performing Raman spectroscopy thereon to obtain a measurement value.

17. The method of claim 1, wherein the at least one characteristic is a concentration of an impurity in the sample and the at least one analytical technique comprises delivering the sample or a portion thereof to the detection zone, and directing a flow of the sample or portion thereof through the monolithic body, thereby separating the sample or portion thereof into one or more molecularly distinct constituents.

18. The method of claim 1, wherein the at least one characteristic comprises a radiation level of the sample.

19. The method of claim 1, which comprises controlling the direction and/or timing of the flow of the sample or portion(s) thereof through the microfluidic chip by way of one or more valve elements.

20. The method of claim 1, which comprises determining at least four characteristics of the sample.

21. The method of claim 1, wherein the monolithic body is a double coated monolithic body.

22. The method of claim 1, wherein the monolithic body is in a hermetically sealed unit comprising at least one inlet and at least one outlet.

* * * * *